US007445897B2

(12) United States Patent
Ho et al.

(10) Patent No.: US 7,445,897 B2
(45) Date of Patent: Nov. 4, 2008

(54) SEQUENCE VARIANTS OF MULTI-DRUG RESISTANCE GENES, MDR1 AND MRP1, AND METHODS FOR ASSESSMENT OF DRUG PENETRATION AND DISPOSITION

(75) Inventors: Rodney J. Y. Ho, Seattle, WA (US); Ziping Yang, Shoreline, WA (US); Danny D. Shen, Edmonds, WA (US); Daniel Wu, Bellevue, WA (US)

(73) Assignee: University of Washington, Seattle, WA (US)

( * ) Notice: Subject to any disclaimer, the term of this patent is extended or adjusted under 35 U.S.C. 154(b) by 109 days.

(21) Appl. No.: 11/045,578

(22) Filed: Jan. 26, 2005

(65) Prior Publication Data

US 2006/0024685 A1 Feb. 2, 2006

Related U.S. Application Data

(60) Provisional application No. 60/539,362, filed on Jan. 26, 2004.

(51) Int. Cl.
*C12Q 1/68* (2006.01)
*G01N 1/30* (2006.01)
*G01N 33/48* (2006.01)

(52) U.S. Cl. ........................................ 435/6; 435/40.5

(58) Field of Classification Search .................... 435/6; 935/77, 78

See application file for complete search history.

(56) References Cited

U.S. PATENT DOCUMENTS

| | | | | |
|---|---|---|---|---|
| 5,837,536 | A | 11/1998 | McDonagh et al. | |
| 6,607,879 | B1 * | 8/2003 | Cocks et al. | 435/6 |
| 6,790,621 | B2 | 9/2004 | Mealey et al. | |
| 2004/0265896 | A1 | 12/2004 | Mealey et al. | |

OTHER PUBLICATIONS

Hoffmeyer et al. Functional polymorphisms of the human multidrugresistance gene: Multiple sequence variations and correlation of one allele with P-glycoprotein expression and activity in vivo. Proceedings of the National Academy of Sciences of the United States of America (Washington, DC) Mar. 28, 2000, vol. 97, No. 7, p. 3473-3478.*

Chen et al. Prevalence of Multidrug Resistance Related to Activation of the mdrl Gene in Human Sarcoma Mutants Derived by Single-Step Doxorubicin Selection. Cancer Research Sep. 15, 1999, vol. 54, p. 4980-4987.*

Adachi et al., "Comparative studies on in vitro methods for evaluating in vivo function of MDR1 P-glycoprotein," *Pharm. Res.* 18:1660-1668 (2001).

Adachi et al., "Quantitative evaluation of the function of small intestinal P-glycoprotein: comparative studies between in Situ and in Vitro," *Pharm Res.* 20:1163-1169 (2003).

Allen et al., "Extensive contribution of the multidrug transporters P-glycoprotein and Mrp1 to basal drug resistance," *Cancer Res.* 60:5760-5766 (2000).

Allen et al., "Potent and specific inhibition of the breast cancer resistance protein multidrug transporter in vitro and in mouse intestine by a novel analogue of fumitremorgin C," *Mol. Cancer Ther.* 1:417-425 (2002).

Allen et al., "Mouse breast cancer resistance protein (Bcrp1/Abcg2) mediates etoposide resistance and transport, but etoposide oral availability is limited primarily by P-glycoprotein," *Cancer Res.* 63:1339-1344 (2003).

Ambudkar, "Purification and reconstitution of functional human P-glycoprotein," *J. Bioenerg. Biomembr.* 27:23-29 (1995). (abstract).

Andreana et al., "Abnormal expression of a 170-kilodalton P-glycoprotein encoded by *MDR1* gene, a metabolically active efflux pump, in $CD4^+$ and $CD8^+$ T cells from patients with human immunodeficiency virus type 1 infection," *AIDS Res. Hum. Retroviruses* 12:1457-1462 (1996).

Arima et al., "Contribution of P-glycoprotein to the enhancing effects of dimethyl-β-cyclodextrin on oral bioavailability of tacrolimus," *J. Pharmacol. Exp. Ther.* 297:547-555 (2001).

Bakos et al., "Functional multidrug resistance protein (MRP1) lacking the N-terminal transmembrane domain," *J. Biol. Chem.* 273:32167-32175 (1998).

Balimane, "Utility of 96 well Caco-2 cell system for increased throughput of P-gp screening in drug discovery," *Eur. J. Pharm. Biopharm.* 58:99-105 (2004).

Bardelmeijer et al., "The oral route for the administration of cytotoxic drugs: strategies to increase the efficiency and consistency of drug delivery," *Invest. New Drugs* 18:231-241 (2000). (abstract).

Bardelmeijer et al. , "Low systemic exposure of oral docetaxel in mice resulting from extensive first-pass metabolism is boosted by ritonavir," *Cancer Res.* 62:6158-6154 (2002).

Bodo et al., "The role of multidrug transporters in drug availability, metabolism and toxicity," *Toxicol. Lett.* 140-141:133-143 (2003).

Brimer et al., "Creation of polarized cells coexpressing CYP3A4, NADPH cytochrome P450 reductase and MDR1/P-glycoprotein," *Pharm. Res.* 17:803-810 (2000). (abstract).

Brinkmann and Eichelbaum, "Polymorphisms in the ABC drug transporter gene MDR1," *Pharmacogenomics* 1:59-64 (2001). (abstract).

(Continued)

*Primary Examiner*—Bruce Campbell
*Assistant Examiner*—Louise Humphrey
(74) *Attorney, Agent, or Firm*—Christensen O'Connor Johnson Kindness PLLC

(57) ABSTRACT

Provided are compositions relating to novel MDR1 polymorphisms, including nucleic acids, polypeptides, and recombinant cells, as well as methods for detection of MDR1 polymorphisms in biological samples and elucidation of the influence of MDR1 polymorphisms on MDR1 protein function. Also provided are a rat MRP1 cDNA and protein, stable cell lines expressing the rat MRP1 protein, and methods of assessing drug penetration or disposition in a cell line expressing a recombinant mammalian MRP1 or MDR1 protein, or a homolog thereof.

6 Claims, 22 Drawing Sheets

OTHER PUBLICATIONS

Brinkmann et al., "Pharmacogenetics of the human drug-transporter gene MDR1: impact of polymorphisms on pharmacotherapy," *Drug Discov. Today* 6:835-839 (2001). (abstract).
Brumme et al., "Influence of polymorphisms within the $CX_3CR1$ and MDR-1 genes on initial antiretroviral therapy response," *AIDS* 17:201-208 (2003).
Cascorbi et al., "Frequency of single nucleotide polymorphisms in the P-glycoprotein drug transporter *MDR1* gene in white subjects," *Clin.Pharmacol. Ther*. 69(3):169-174 (2001).
Chan et al., "The ABCs of drug transport in intestine and liver:efflux proteins limiting drug absorption and bioavailability," *Eur. J. Pharm. Sci*. 21:25-51 (2004). (abstract).
Cherrington et al., "Organ distribution of multidrug resistance proteins 1, 2, and 3 (Mrp1, 2, and 3) mRNA and hepatic induction of Mrp3 by constitutive androstane receptor activators in rats," *J. Pharmacol. Exp. Ther*. 300: 97-104 (2002).
Choudri et al., "Constitutive expression of various xenobiotic and endobiotic transporter mRNAs in the Choroid plexus of rats," *Drug Metabol. Dispos*. 31:1337-1345 (2003).
Cole et al., "Pharmacological characterization of multidrug resistant MRP-transfected human tumor cells," *Cancer Res*. 54:5902-5910 (1994).
Dey et al., "Pharmacokinetics of erythromycin in rabbit corneas after single-dose infusion: role of P-glycoprotein as a barrier to in vivo ocular drug absorption," *J Pharmacol. Exp. Ther*. 311:246-255 (2004).
Dietrich et al., "ABC of oral bioavailability: transporters as gatekeepers in the gut," *Gut*. 52:1788-1795 (2003).
Donahue et al., "Effects of nelfinavir and its M8 metabolite on lymphocyte P-glycoprotein activity during antiretroviral therapy," *Clin. Pharmacol. Ther*. 73:78-86 (2003).
Dupuis et al., "Saquinavir induces stable and functional expression of the multidrug transporter P-glycoprotein in human CD4 T-lymphoblastoid $CEM^{rev}$ cells," *HIV Med*. 4:338-345 (2003).
Durr et al., "St John's Wort induces intestinal P-glycoprotein/MDR1 and intestinal and hepatic CYP3A4," *Clin. Pharmacol. Ther*. 68:598-604 (2000). (abstract).
Dyszlewski et al., "Characterization of a novel 99mTc-carbonyl complex as a functional probe of MDR1 P-glycoprotein transport activity," *Mol. Imaging* 1:24-35 (2002). (abstract).
Evers et al., "Transport of glutathione prostaglandin A conjugates by the multidrug resistance protein 1," *FEBS Lett*. 419:112-116 (1997).
Evers et al., "Drug export activity of the human canalicular multispecific organic anion transporter in polarized kidney MDCK cells expressing *cMOAT* (*MRP2*) cDNA," *J. Clin. Invest*. 101:1310-1319 (1998).
Evers et al., "Vinblastine and sulfinpyrazone export by the multidrug resistance protein MRP2 is associated with glutathione export," *Br. J. Cancer* 83:375-383 (2000).
Fellay et al., "Response to antiretroviral treatment in HIV-1-infected individuals with allelic variants of the multidrug resistance transporter 1: a pharmacogenetics study," *Lancet* 359:30-36 (2002).
Ford et al., "Effect of protease inhibitor-containing regimens on lymphocyte multidrug resistance transporter expression," *J. Antimicrob. Chemother*. 52:354-358 (2003).
Genne et al., "Cinchonine per os: efficient circumvention of P-glycoprotein-mediated multidrug resistance," *Anticancer Drug. Des*. 10:103-118 (1995). (abstract).
Ghersi-Egea and Strazielle, "Brain drug delivery, drug metabolism, and multidrug resistance at the choroid plexus," *Microsc. Res. Tech*. 52:83-88 (2001). (abstract).
Gottesman and Pastan, "Biochemistry of multidrug resistance mediated by the multidrug transporter," *Annu. Rev. Biochem*. 62:385-427 (1993).
Greiner et al., "The role of intestinal P-glycoprotein in the interaction of digoxin and rifampin," *J. Clin. Invest*. 104:147-153 (1999).
Hennessy, "Intracellular accumulation of nelfinavir and its relationship to P-glycoprotein expression and function in HIV-infected patients," *Antivir. Ther*. 9:115-122 (2004).
Higgins et al., "ABC transporters: from microorganisms to man," *Annu. Rev. Cell Biol*. 8:67-113 (1992).
Hoffmeyer et al., "Functional polymorphisms of the human multidrug-resistance gene: multiple sequence variations and correlation of one allele with P-glycoprotein expression and activity in vivo," *Proc. Natl. Acad. Sci. USA* 97:3473-3478 (2000).
Huisman et al., "Multidrug resistance protein 2 (MRP2) transports HIV protease inhibitors, and transport can be enhanced by other drugs," *AIDS* 16:2295-2301 (2002).
Johne et al., "Modulation of steady-state kinetics of digoxin by haplotypes of the P-glycoprotein *MDR1* gene," *Clin. Pharmacol. Ther*. 72:584-594 (2002).
Jones, "P-Glycoprotein and transporter MRP1 reduce HIV protease inhibitor uptake in CD4 cells: potential for accelerated viral drug resistance?," *AIDS* 15:1353-1358 (2001).
Jonker et al., "Role of blood-brain barrier P-glycoprotein in limiting brain accumulation and sedative side-effects of asimadoline, a peripherally acting analgaesic drug," *Br. J. Pharmacol*. 127:43-50 (1999).
Jonker et al., "Role of breast cancer resistance protein in the bioavailability and fetal penetration of tototecan," *J. Natl. Cancer Instit*. 92:1651-1656 (2000).
Kafka et al., "Polymorphism C3435T of the MDR-1 gene predicts response to preoperative chemotherapy in locally advanced breast cancer," *Int. J. Oncol*. 22:1117-1121 (2003). (abstract).
Kan et al., "Effect of hydroxyzine on the transport of etoposide in rat small intestine," *Anticancer Drugs* 12:267-273 (2001). (abstract).
Kerb et al., "ABC drug transporters: hereditary polymorphisms and pharmacological impact in MDR1, MRP1 and MRP2," *Pharmacogenomics* 2:51-64 (2001). (abstract).
Ketabi-Kiyanvash et al., "P-glycoprotein modulation by the designer drugs methylenedioxymethamphetamine, methylenedioxyethylamphetamine and paramethoxyamphetamine," *Addict. Biol*. 8:413-418 (2003).
Kim et al., "Identification of functionally variant MDR1 alleles among European Americans and African Americans," *Clin. Pharmacol. Ther*. 70:189-199 (2001).
Kim, "Drug transporters in HIV therapy," *Top HIV Med*. 11:136-139 (2003). (abstract).
Kim and Benet, "P-glycoprotein (P-gp/MDR1)-mediated efflux of sex-steroid hormones and modulation of P-gp expression in vitro," *Pharm. Res*. 21:1284-1293 (2004). (abstract).
Kimchi-Sarfaty et al., "Functional characterization of coding polymorphisms in the human *MDR1* gene using a vaccinia virus expression system," *Mol. Pharmacol*. 62:1-6 (2002).
Kool et al., "MRP3, an organic anion transporter able to transport anti-cancer drugs," *Proc. Natl. Acad. Sci. USA* 96:6914-6919 (1999).
Kroetz et al., "Sequence diversity and haplotype structure in the human *ABCB1* (*MDR1*, multidrug resistance transporter) gene," *Pharmacogenetics* 13:481-494 (2003).
Kruh et al., "MRP subfamily transporters and resistance to anticancer agents," *J. Bioenerg. Biomembr*. 33:493-501 (2001).
Kunta and Sinko, "Intestinal drug transporters: in vivo function and clinical importance," *Curr. Drug Metab*. 5:109-124 (2004).
Kurata et al., "Role of human MDR1 gene polymorphism in bioavailability and interaction of digoxin, a substrate of P-glycoprotein," *Clin. Pharmacol. Ther*. 72:209-219 (2002). (abstract).
Lan et al., "Mdr1 limits CYP3A metabolism in vivo," *Mol. Pharmacol*. 58:863-869 (2000). (abstract).
Landowski et al., "Gene expression in the human intestine and correlation with oral valacyclovir pharmacokinetic parameters," *J. Pharmacol. Exp. Ther*. 306:778-786 (2003).
Laupeze et al., "Differential expression of the efflux pumps P-glycoprotein and multidrug resistance-associated protein in human monocyte-derived dendritic cells," *Hum. Immunol*. 62:1073-1080 (2001).
Lee et al., "HIV-1 protease inhibitors are substrates for the *MDR1* multidrug transporter," *Biochemistry* 37:3594-3601 (1998).
Liang et al., "Selective myelo-protection by MDR1 and MnSOD genes regulated by a specific promoter," *Zhonghua Zhong Liu Za Zhi* 25:17-20 (2003). (abstract).
Lin, "Drug-drug interaction mediated by inhibition and induction of P-glycoprotein," *Adv. Drug. Deliv. Rev*. 55:53-81 (2003).

Liu and Hu, "P-glycoprotein and bioavailability-implication of polymorphism," *Clin. Chem. Lab Med.* 38:877-881 (2000). (abstract).
Loo and Clarke, "Functional consequences of phenylalanine mutations in the predicted transmembrane domain of P-glycoprotein," *J. Biol. Chem.* 268:19965-19972 (1993).
Loo and Clarke, "Functional consequences of proline mutations in the predicted transmembrane domain of P-glycoprotein," *J. Biol. Chem.* 268:3143-3149 (1993).
Loo and Clarke, "Functional consequences of glycine mutations in the predicted cytoplasmic loops of P-glycoprotein," *J. Biol. Chem.* 269:7243-7248 (1994).
Loo and Clarke, "Mutations to amino acids located in predicted transmembrane segment 6 (TM6) modulate the activity and substrate specificity of human P-glycoprotein," *Biochem.* 33:14049-14057 (1994).
Lown et al., "Role of intestinal P-glycoprotein (mdr1) in interpatient variation in the oral bioavailability of cyclosporine," *Clin. Pharmacol. Ther.* 62:248-260 (1997). (abstract).
Luo et al., "Intestinal transport of irinotecan in CACO-2 cells and MDCK II cells overexpressing efflux transporters PGP, CMOAT, and MRP1," *Drug. Metab. Dispos.* 30:763-770 (2002).
Martin et al., "Communication between multiple drug binding sites on P-glycoprotein," *Mol. Pharmacol.* 58:624-632 (2000).
Meaden et al., "Determination of P-gp and MRP1 expression and function in peripheral blood mononuclear cells in vivo," *J. Immunol. Methods* 262:159-165 (2002).
Morita et al., "Human MDR1 polymorphism: G2677T/A and C3435T have no effect on MDR1 transport activities," *Biochem. Pharmacol.* 65:1843-1852 (2003).
Muredda et al., "Cloning and characterization of the murine and rat mrp1 promoter regions," *Mol. Pharmacol.* 64:1259-1269 (2003).
Nasi et al., "MDR1 C3435T genetic polymorphism does not influence the response to antiretroviral therapy in drug-naive HIV-positive patients," *AIDS* 17:1696-1698 (2003).
Nunoya et al., "Molecular cloning and pharmacological characterization of Rat Multidrug Resistance Protein 1 (MRP1)," *Drug Metabol. Dispos.* 31:1016-1026 (2003).
Paietta, "Classical multidrug resistance in acute myeloid leukaemia," *Med. Oncol.* 14:53-60 (1997). (abstract).
Parasrampuria et al., "A human lymphocyte based ex vivo assay to study the effect of drugs on P-glycoprotein (P-gp) function," *Pharm. Res.* 18:39-44 (2001).
Parker et al., "Effects of grapefruit juice on intestinal P-glycoprotein: evaluation using digoxin in humans," *Pharmacotherapy* 23:979-987 (2003). (abstract).
Patel and Mitra, "Strategies to overcome simultaneous P-glycoprotein mediated efflux and CYP3A4 mediated metabolism of drugs," *Pharmacogenomics* 2:401-415 (2001). (abstract).
Paul et al., "Structure and in vitro substrate specificity of the murine multidrug resistance-associated protein," *Biochem.* 35:13647-13655 (1996).
Pendse et al., "P-glycoprotein—a novel therapeutic target for immunomodulation in clinical transplantation and autoimmunity?," *Curr. Drug Targets* 4:469-476 (2003). (abstract).
Perloff et al., "Ritonavir induces P-glycoprotein expression, multidrug resistance-associated protein (MRP1) expression, and drug transporter-mediated activity in a human intestinal cell line," *J. Pharm Sci.* 90:1829-1837 (2001). (abstract).
Polli et al., "Rational use of in vitro P-glycoprotein assays in drug discovery," *J. Pharmacol. Exp. Ther.* 299:620-628 (2001).
Regina et al., "Mrp1 multidrug resistance-associated protein and P-glycoprotein expression in rat brain microvessel endothelial cells," *J. Neurochem.* 71:705-715 (1998).
Rengelshausen et al., "Contribution of increased oral bioavailability and reduced nonglomerular renal clearance of digoxin to the digoxin-clarithromycin interaction," *Br. J. Clin. Parmacol.* 56:32-38 (2003). (abstract).
Roots, "MDR-1 gene changes effectiveness of drugs. DNA analysis instead of does schedule F?. Interview by Petra Eiden," *MMW Fortschr. Med.* 142:16 (2000) (abstract).
Scher and Norton, "Chemotherapy for urothelial tract malignancies: breaking the deadlock." *Semin Surg. Oncol.* 8:316-341 (1992). (abstract).
Schinkel, "Absence of the mdr1a P-Glycoprotein in mice affects tissue distribution and pharmacokinetics of dexamethasone, digoxin, and cyclosporine A," *J. Clin. Invest.* 96:1698-1705 (1995).
Schinkel, "The physiological function of drug-transporting P-glycoproteins," *Semin. Cancer Biol.* 8:161-170 (1997).
Sharma et al., "Novel gallium(III) complexes transported by MDR1 P-glycoprotein: potential PET imaging agents for probing P-glycoprotein-mediated transport activity in vivo," *Chem. Biol.* 7:335-343 (2000). (abstract).
Smit et al., "Contribution of the murine mdr1a P-glycoprotein to hepatobiliary and intestinal elimination of cationic drugs as measured in mice with an *mdr1a* gene disruption," *Hepatology* 27:1056-1063 (1998).
Smit et al., Heterologous expression of various p-glycoproteins in polarized epithelial cells induces directional transport of small (Type 1) and bulky (Type 2) cationic drugs, *J. Pharmacol. Exper. Ther.* 286:321-327 (1998).
Smit et al., "Hepatobiliary and intestinal clearance of amphiphilic cationic drugs in mice in which both *mdr1a* and *mdr1b* genes have been disrupted," *Br. J. Pharmacol.* 124:416-424 (1998).
Smith et al., "Availability of PSC833, a substrate and inhibitor of P-glycoproteins, in various concentrations of serum," *J. Natl. Cancer Inst.* 90:1161-1166 (1998).
Soldner et al., "Grapefruit juice activates P-glycoprotein-mediated drug transport," *Pharm. Res.* 16:478-485 (1999). (abstract).
Srinivas et al., "Human immunodeficiency virus protease inhibitors serve as substrates for multidrug transporter proteins MDR1 and MRP1 but retain antiviral efficacy in cell lines expressing these transporters," *Antimicrob. Agents Chemother.* 42:3157-3162 (1998).
Stormer et al., "Methadone inhibits rhodamine123 transport in Caco-2 cells," *Drug. Metab. Dispos.* 29:954-956 (2001).
Stride et al., "Pharmacological characterization of the murine and human orthologs of multidrug-resistance protein in transfected human embryonic kidney cells," *Mol. Pharmacol.* 52:344-353 (1997).
Suzuki and Sugiyama, "Role of metabolic enzymes and efflux transporters in the absorption of drugs from the small intestine," *Eur. J. Pharm. Sci.* 12:3-12 (2000). (abstract).
Toffoli and Cecchin, "Pharmacogenetics of stomach cancer," *Suppl. Tumori* 2:S19-22 (2003). (abstract).
Troutman, "Novel experimental parameters to quantify the modulation of absorptive and secretory transport of compounds by P-glycoprotein in cell culture models of intestinal epithelium," *Pharm.Res.* 20:1210-1224 (2003).
Uhr and Grauer, "abcb1ab P-glycoprotein is involved in the uptake of citalopram and trimipramine into the brain of mice," *J. Psychiatr. Res.* 37:179-185 (2003). (abstract).
van Montfoort et al., "Drug uptake systems in liver and kidney," *Curr. Drug Metab.* 4:185-211 (2003).
Verstuyft et al., "Dipyridamole enhances digoxin bioavailability via P-glycoprotein inhibition," *Clin. Pharmacol. Ther.* 73:51-60 (2003).
Walle et al., "Transport of the flavonoid chrysin and its conjugated metabolites by the human intestinal cell line Caco-2," *Biochem. Parmacol.* 58:431-438 (1999). (abstract).
Wang et al., "Establishment of P-glycoprotein substrate screening model and its preliminary application," *World J. Gastroenterol* 10:1365-1368 (2004).
Washington et al., "Interaction of anti-HIV protease inhibitors with the multidrug transporter P-glycoprotein (P-gp) in human cultured cells," *J. Acquir. Immune Defic. Syndr. Hum. Retrovirol.* 19:203-209 (1998).
Wielandt et al., "Polymorphisms of the multiple drug resistance gene (MDR1) in Mapuche, Mestizo and Maori populations in Chile," *Rev. Med. Chil.* 132:1061-1068 (2004). (abstract).
Wijnholds et al., "Multidrug-resistance protein 5 is a multispecific organic anion transporter able to transport nucleotoide analogs," *PNAS* 97:7476-7481 (2000).
Wijnholds, "Drug resistance caused by multidrug resistance-associated proteins," *Novartis Found. Symp.* 243:69-79, discussion 80-2, 180-185 (2002).

Williams et al., "The effect of cell culture conditions on saquinavir transport through, and interactions with, MDCK11 cells overexpressing hMDR1," *J. Pharm. Sci.* 92:1957-1967 (2003).

Woodahl and Ho, "The role of MDR1 genetic polymorphisms in interindividual variability in P-glycoprotein expression and function," *Curr. Drug Metab.* 5:11-19 (2004).

Woodahl et al., "Multidrug resistance gene G1199A polymorphism alters efflux transport activity of P-glycoprotein," *J. Pharmacol. Exp. Ther.* 310:1199-1207 (2004).

Xu et al., "Adenovirus-mediated transfer of anti-MDR1 ribozyme in the treatment of multidrug-resistant human lymphoma in SCID mice," *Zhonghua Zhong Liu Za Zhi* 24:529-532 (2002). (abstract).

Yamaguchi et al., "Pharmacokinetic role of P-glycoprotein in oral bioavailability and intestinal secretion of grepafloxacin in vivo," *J. Pharmacol. Exp. Ther.* 300:1063-1069 (2002).

Yang et al., "Characteristics of P388/VMDRC.04, a simple, sensitive model for studying P-glycoprotein antagonists," *Cancer Res.* 54:730-737 (1994).

Zhang and Benet, "Characterization of P-glycoprotein mediated transport of K02, a novel vinylsulfone peptidomimetic cysteine protease inhibitor, across MDR1-MDCK and Caco-2 cell monolayers," *Pharm. Res.* 15:1520-1524 (1998).

Zhang et al., "Overlapping substrate specificities of cytochrome P450 3A and P-glycoprotein for a novel cysteine protease inhibitor," *Drug Metab. Dispos.* 26:360-366 (1998).

Zhang et al., "Identification of an amino acid residue in multidrug resistance protein 1 critical for conferring resistance to anthracyclines," *J. Biol. Chem.* 276(16): 13231-13239 (2001).

Zhou et al., "Herbal modulation of P-glycoprotein," *Drug Metab. Rev.* 36:57-104 (2004). (abstract).

* cited by examiner

Figure 1

```
rMRP1  ------------------------------------------------------------ 0
mMRP1  ------------------------------------------------------------ 0
hMRP1  CCAGGCGGCGTTGCGGCCCCGGCCCCGGCTCCCTGCGCCGCCGCCGCCGCCGCCGCCGCC 60

rMRP1  ------------------------------------------------------------ 0
mMRP1  ------------------------------------------------------------ 0
hMRP1  GCCGCCGCCGCCGCCGCCAGCGCTAGCGCCAGCAGCCGGGCCCGATCACCCGCCGCCCGG 120

rMRP1  ------------------------------------------------------------ 0
mMRP1  ------------------------------------------------------------ 0
hMRP1  TGCCCGCCGCCGCCCGCGCCAGCAACCGGGCCCGATCACCCGCCGCCCGGTGCCCGCCGC 180

rMRP1  ----------------ATGGCGCTCCGCAGCTTCTGCAGCTCTGATGGCTCCGATCCGCT 44
mMRP1  ----------------ATGGCGCTGCGCAGCTTCTGCAGCGCTGATGGCTCCGATCCACT 44
hMRP1  CGCCCGCGCCACCGGCATGGCGCTCCGCGGCTTCTGCAGCGCCGATGGCTCCGACCCGCT 240

rMRP1  CTGGGATTGGAATGTCACATGGCACACCAGCAACCCTGACTTTACCAAGTGCTTTCAGAA 104
mMRP1  CTGGGACTGGAATGTCACATGGCACACCAGCAACCCCGACTTTACCAAGTGCTTTCAGAA 104
hMRP1  CTGGGACTGGAATGTCACGTGGAATACCAGCAACCCCGACTTCACCAAGTGCTTTCAGAA 300

rMRP1  TACGGTCCTCACATGGGTGCCTTGTTTCTACCTCTGGTCCTGTTTCCCCCTCTACTTCCT 164
mMRP1  CACGGTCCTCACATGGGTGCCTTGTTTCTACCTCTGGTCCTGTTTCCCCCTCTACTTCTT 164
hMRP1  CACGGTCCTCGTGTGGGTGCCTTGTTTTTACCTCTGGGCCTGTTTCCCCTTCTACTTCCT 360

rMRP1  CTATCTCTCTCGACATGACCGGGGCTACATCCAGATGACACACCTCAACAAAGCCAAAAC 224
mMRP1  CTATCTCTCTCGCCATGACCGGGGCTACATCCAGATGACACACCTCAACAAAACCAAAAC 224
hMRP1  CTATCTCTCCCGACATGACCGAGGCTACATTCAGATGACACCTCTCAACAAAACCAAAAC 420

rMRP1  TGCCTTAGGATTCTTTCTGTGGATCATCTGCTGGGCAGACCTCTTCTACTCTTTCTGGGA 284
mMRP1  TGCCTTAGGATTCTTTCTGTGGATCATCTGCTGGGCAGACCTCTTCTACTCTTTCTGGGA 284
hMRP1  TGCCTTGGGATTTTTGCTGTGGATCGTCTGCTGGGCAGACCTCTTCTACTCTTTCTGGGA 480

rMRP1  AAGAAGTCAGGGAATGCTCCTAGCCCCGGTGCTACTGGTCAGCCCGACACTGCTAGGCAT 344
mMRP1  AAGAAGTCAGGGAGTGCTCCGAGCCCCGGTGTTACTGGTCAGCCCAACACTGCTGGGCAT 344
hMRP1  AAGAAGTCGGGGCATATTCCTGGCCCCAGTGTTTCTGGTCAGCCCAACTCTCTTGGGCAT 540

rMRP1  CACCATGCTGCTCGCCACCTTTTTAATTCAGTTTGAGCGAAGGAAAGGAGTCCAGTCCTC 404
mMRP1  CACCATGCTGCTCGCCACCTTTTTGATACAGCTTGAACGGAGGAAGGGAGTCCAATCCTC 404
hMRP1  CACCACGCTGCTTGCTACCTTTTTAATTCAGCTGGAGAGGAGGAAGGGAGTTCAGTCTTC 600

rMRP1  AGGGATAATGCTTACTTTCTGGCTTGTAGCCCTACTCTGCGCCCTTGCCATCTTGAGATC 464
mMRP1  GGGAATTATGCTTACTTTCTGGCTCGTAGCCCTACTCTGTGCCCTTGCCATCTTGAGATC 464
hMRP1  AGGGATCATGCTCACTTTCTGGCTGGTAGCCCTAGTGTGTGCCCTAGCCATCCTGAGATC 660

rMRP1  TAAGATCATCTCTGCCTTAAAAAAGGATGCTCAAGTGGACATGTTTCGAGATTCTGCATT 524
mMRP1  TAAGATCATCTCTGCCTTAAAAAAGGATGCTCATGTGGACGTGTTTCGAGATTCCACGTT 524
hMRP1  CAAAATTATGACAGCCTTAAAAGAGGATGCCCACGTGGACCTGTTTCGTGACATCACTTT 720

rMRP1  CTATCTCTACTTCACCCTCGTGTTCATTCAGCTTGTGCTGTCCTGCTTCTCAGACAGCTC 584
mMRP1  CTATCTGTACTTCACCCTTGTGCTTGTTCAGCTCGTGCTGTCCTGCTTCTCAGACTGCTC 584
hMRP1  CTACGTCTACTTTTCCCTCTTACTCATTCAGCTCGTCTTGTCCTGTTTCTCAGATCGCTC 780

rMRP1  ACCCTTGTTCTCTGAAACTGTCCGTGACCCGAATCCATGTCCAGAATCGAGTGCCTCTTT 644
mMRP1  ACCCCTGTTCTCTGAAACTGTCCATGACCGGAATCCATGCCCAGAATCCAGTGCCTCTTT 644
hMRP1  ACCCCTGTTCTCGGAAACCATCCACGACCCTAATCCCTGCCCAGAGTCCAGCGCTTCCTT 840
```

Figure 1 (continued)

```
rMRP1  TCTTTCCAGGATCACTTTTTGGTGGATTACAGGGATGATGGTGCACGGCTACCGCCAGCC 704
mMRP1  CCTTTCCAGGATTACTTTCTGGTGGATTACAGGGATGATGGTGCACGGCTACCGCCAGCC 704
hMRP1  CCTCTCGAGGATCACCTTCTGGTGGATCACAGGGTTGATTGTCCGGGGCTACCGCCAGCC 900

rMRP1  CCTGAAGAGCAGTGACCTCTGGTCATTGAATAAAGAGGACACGTCAGAACAAGTGGTACC 764
mMRP1  CCTGGAGAGCAGTGACCTCTGGTCATTGAATAAGGAGGACACATCAGAACAAGTGGTACC 764
hMRP1  CCTGGAGGGCAGTGACCTCTGGTCCTTAAACAAGGAGGACACGTCGGAACAAGTCGTGCC 960

rMRP1  TGTGCTGGTGAATAACTGGAAGAAGGAATGTGTTAAGTCGAGGAAGCAGCCTGTACGGAT 824
mMRP1  TGTGCTGGTGAATAACTGGAAGAAGGAATGTGATAAGTCAAGGAAGCAGCCTGTACGGAT 824
hMRP1  TGTTTTGGTAAAGAACTGGAAGAAGGAATGCGCCAAGACTAGGAAGCAGCCGGTGAAGGT 1020

rMRP1  TGTGTATGCCCCTCCCAAAGATCCCACCAAGCCTAAGGGAAGTTCTCAGTTGGATGTGAA 884
mMRP1  TGTGTATGCCCCTCCCAAAGATCCCAGCAAGCCTAAGGGAAGTTCCCAGTTGGATGTGAA 884
hMRP1  TGTGTA--CTCCTCC-AAGGATCCTGCCCAGCCGAAAGAGAGTTCCAAGGTGGATGCGAA 1077

rMRP1  TGAGGAAGTGGAGGCACTGATTGTCAAGTCATCCCACAAGGACCGGGAGCCCTCTCTGTT 944
mMRP1  TGAGGAGGTGGAGGCACTGATTGTCAAGTCACCCCACAAGGATCGGGAGCCCTCTCTGTT 944
hMRP1  TGAGGAGGTGGAGGCTTTGATCGTCAAGTCCCCACAGAAGGAGTGGAACCCCTCTCTGTT 1137

rMRP1  CAAGGTGTTGTACAAGACCTTTGGGCCCTACTTCCTCATGAGCTTCCTGTACAAGGCCCT 1004
mMRP1  CAAGGTGTTATACAAGACTTTTGGTCCCTACTTCCTCATGAGCTTCCTGTACAAGGCCCT 1004
hMRP1  TAAGGTGTTATACAAGACCTTTGGGCCCTACTTCCTCATGAGCTTCTTCTTCAAGGCCAT 1197

rMRP1  TCATGACCTGATGATGTTTGCTGGCCCTGAGATCTTGGAATTGATTATCAACTTCGTGAA 1064
mMRP1  TCATGACCTGATGATGTTTGCCGGCCCCAAGATCTTGGAATTGATTATCAACTTCGTGAA 1064
hMRP1  CCACGACCTGATGATGTTTTCCGGGCCGCAGATCTTAAAGTTGCTCATCAAGTTCGTGAA 1257

rMRP1  TGACAGGGAGGCCCCTGACTGGCAGGGCTACTTGTACACAGCACTGCTGTTTGTCAGTGC 1124
mMRP1  TGACAGGGAGGCTCCCGACTGGCAGGGCTACTTTTACACAGCACTGCTGTTTGTCAGCGC 1124
hMRP1  TGACACGAAGGCCCCAGACTGGCAGGGCTACTTCTACACCGTGCTGCTGTTTGTCACTGC 1317

rMRP1  CTGTCTGCAGACACTGGCACTCCACCAGTACTTTCATATCTGCTTCGTCACCGGCATGCG 1184
mMRP1  CTGTCTGCAGACACTGGCACTCCACCAGTACTTTCATATCTGCTTCGTCAGTGGCATGCG 1184
hMRP1  CTGCCTGCAGACCCTCGTGCTGCACCAGTACTTCCACATCTGCTTCGTCAGTGGCATGAG 1377

rMRP1  CATCAAGACTGCTGTGGTGGGCGCTGTTTACCGCAAGGCTCTTGTGATCACCAATTCAGC 1244
mMRP1  CATCAAGACTGCTGTGGTGGGCGCTGTCTATCGTAAGGCTCTTTTGATCACCAATGCAGC 1244
hMRP1  GATCAAGACCGCTGTCATTGGGGCTGTCTATCGGAAGGCCCTGGTGATCACCAATTCAGC 1437

rMRP1  TAGAAAATCGTCCACAGTTGGAGAGATTGTCAACCTCATGTCCGTGGATGCCCAGCGCTT 1304
mMRP1  TAGAAAATCTTCCACGGTCGGAGAGATTGTCAACCTCATGTCCGTGGATGCTCAGCGCTT 1304
hMRP1  CAGAAAATCCTCCACGGTCGGGGAGATTGTCAACCTCATGTCTGTGGACGCTCAGAGCTT 1497

rMRP1  CATGGACTTGGCCACGTATATTAACATGATCTGGTCAGCCCCTCTGCAAGTCACCCTAGC 1364
mMRP1  CATGGACTTGGCCACGTACATTAACATGATCTGGTCAGCCCCTCTGCAAGTCATCCTAGC 1364
hMRP1  CATGGACTTGGCCACGTACATTAACATGATCTGGTCAGCCCCCCTGCAAGTCATCCTTGC 1557

rMRP1  CCTCTACTTCCTGTGGCTGAACCTGGGCCCTTCTGTGCTGGCTGGGGTGGCTGTTATGAT 1424
mMRP1  CCTCTACTTCCTGTGGCTGAGCCTGGGCCCTTCTGTGCTGGCTGGAGTGGCTGTGATGAT 1424
hMRP1  TCTCTACCTCCTGTGGCTGAATCTGGGCCCTTCCGTCCTGGCTGGAGTGGCGGTGATGGT 1617

rMRP1  CCTCATGGTGCCCTTCAATGCTGTGATGGCCATGAAGACCAAGACTTACCAGGTGGCACA 1484
mMRP1  TCTCATGGTACCCTTAAATGCTGTGATGGCCATGAAGACCAAGACCTACCAGGTGGCACA 1484
hMRP1  CCTCATGGTGCCCGTCAATGCTGTGATGGCGATGAAGACCAAGACGTATCAGGTGGCCCA 1677
```

Figure 1 (continued)

```
rMRP1  CATGAAGAGCAAAGACAACCGAATCAAGCTGATGAACGAGATCCTCAATGGGATCAAAGT 1544
mMRP1  CATGAAGAGCAAAGACAACCGAATCAAGCTGATGAACGAGATCCTCAATGGGATCAAAGT 1544
hMRP1  CATGAAGAGCAAAGACAATCGGATCAAGCTGATGAACGAAATTCTCAATGGGATCAAAGT 1737

rMRP1  ACTCAAATTGTACGCCTGGGAGCTGGCTTTCCAGGACAAAGTTATGAACATCAGGCAGGA 1604
mMRP1  CCTCAAGCTGTACGCCTGGGAGCTGGCCTTCCAGGACAAAGTCATGAGCATCAGGCAGGA 1604
hMRP1  GCTAAAGCTTTATGCCTGGGAGCTGGCATTCAAGGACAAGGTGCTGGCCATCAGGCAGGA 1797

rMRP1  GGAGCTCAAGGTGCTGAAGAAATCCGCCTACCTGGCGGCTGTGGGCACATTCACATGGGT 1664
mMRP1  GGAGCTCAAGGTGCTGAAGAAATCTGCCTACCTGGCAGCTGTAGGCACATTCACGTGGGT 1664
hMRP1  GGAGCTGAAGGTGCTGAAGAAGTCTGCCTACCTGTCAGCCGTGGGCACCTTCACCTGGGT 1857

rMRP1  TTGCACACCTTTCCTGGTGGCTCTGTCAACCTTTGCTGTCTTTGTGACTGTGGACGAGAA 1724
mMRP1  GTGCACACCTTTCCTGGTGGCCCTGTCAACCTTTGCTGTCTTTGTGACTGTGGATGAGAG 1724
hMRP1  CTGCACGCCCTTTCTGGTGGCCTTGTGCACATTTGCCGTCTACGTGACCATTGACGAGAA 1917

rMRP1  GAACATCCTAGATGCAAAGAAAGCCTTTGTATCCCTAGCCCTGTTCAATATCTTGCGCTT 1784
mMRP1  AAATATCCTAGATGCAAAGAAAGCCTTTGTGTCCCTAGCCCTGTTCAATATCTTGCGCTT 1784
hMRP1  CAACATCCTGGATGCCCAGACAGCCTTCGTGTCTTTGGCCTTGTTCAACATCCTCCGGTT 1977

rMRP1  CCCACTCAACATCCTACCCATGGTCATCAGCAGCATTGTGCAGGCCAGCGTGTCCCTCAA 1844
mMRP1  CCCACTCAACATCCTGCCCATGGTTATCAGCAGCATTGTGCAGGCCAGCGTGTCCCTCAA 1844
hMRP1  TCCCCTGAACATTCTCCCCATGGTCATCAGCAGCATCGTGCAGGCGAGTGTCTCCCTCAA 2037

rMRP1  GCGTCTCAGGATCTTTCTGTCTCACGAGGAGCTGGAGCCAGACAGCATCGAGCGATGGTC 1904
mMRP1  GCGTCTCAGGATTTTTCTGTCTCATGAGGAGCTGGAGCCAGACAGCATTGAGCGCAGGTC 1904
hMRP1  ACGCCTGAGGATCTTTCTCTCCCATGAGGAGCTGGAACCTGACAGCATCGAGCGACGGCC 2097

rMRP1  GATCAAGGATGGTGGAGGGATGAATAGCATCACTGTGAAGAATGCAACCTTCACTTGGGC 1964
mMRP1  GATCAAGAGTGGAGAAGG---GAATAGCATCACTGTGAAGAATGCAACCTTCACTTGGGC 1961
hMRP1  TGTCAAAGACGGCGGGGGCACGAACAGCATCACCGTGAGGAATGCCACATTCACCTGGGC 2157

rMRP1  CAGGGATGAACCTCCCACACTGAATGGCATCACCTTCGCCATCCCTGATGGAGCCCTTGT 2024
mMRP1  CAGGGGTGAACCTCCCACACTGAATGGCATCACCTTCTCCATTCCTGAAGGAGCCCTTGT 2021
hMRP1  CAGGAGCGACCCTCCCACACTGAATGGCATCACCTTCTCCATCCCCGAAGGTGCTTTGGT 2217

rMRP1  GGCCGTGGTGGGCCAGGTAGGCTGTGGGAAGTCATCTCTGCTGTCAGCCCTGCTGGCTGA 2084
mMRP1  GGCCGTGGTGGGCCAGGTAGGCTGCGGGAAGTCATCTCTGCTGTCAGCCCTGCTGGCTGA 2081
hMRP1  GGCCGTGGTGGGCCAGGTGGGCTGCGGAAAGTCGTCCCTGCTCTCAGCCCTCTTGGCTGA 2277

rMRP1  GATGGACAAAGTGGAGGGACATGTGACTCTCAAGGGCTCCGTGGCCTATGTGCCCCAGCA 2144
mMRP1  GATGGACAAGGTGGAGGGACATGTGACTCTCAAGGGCTCCGTGGCCTACGTGCCCCAGCA 2141
hMRP1  GATGGACAAAGTGGAGGGGCACGTGGCTATCAAGGGCTCCGTGGCCTATGTGCCACAGCA 2337

rMRP1  GGCCTGGATTCAGAATGACTCTCTCCGAGAGAACATACTGTTTGGGCGCCCCCTGCAGGA 2204
mMRP1  GGCCTGGATTCAGAATGACTCTCTCCGAGAGAACATACTGTTTGGGCACCCCCTGCAGGA 2201
hMRP1  GGCCTGGATTCAGAATGATTCTCTCCGAGAAAACATCCTTTTTGGATGTCAGCTGGAGGA 2397

rMRP1  ACATTGCTACAAGGCGGTGATGGAGGCCTGTGCCCTGCTTCCGGATTTGGAAATCCTTCC 2264
mMRP1  AAATTACTACAAGGCAGTTATGGAAGCCTGTGCCCTTCTTCCAGATTTGGAAATCCTGCC 2261
hMRP1  ACCATATTACAAGGTCCGTGATACAGGCCTGTGCCCTGCTCCCAGACCTGGAAATCCTGCC 2457

rMRP1  CAGTGGGGACCTCACAGAGATTGGTGAGAAGGGTGTGAACCTGTCGGGGGGCCAGAAGCA 2324
mMRP1  CAGTGGGGACCGCACAGAGATCGGTGAGAAGGGTGTGAACCTGTCAGGGGGCCAGAAGCA 2321
hMRP1  CAGTGGGGATCGGACAGAGATTGGCGAGAAGGGCGTGAACCTGTCTGGGGGCCAGAAGCA 2517
```

Figure 1 (continued)

```
rMRP1  GCGTGTGAGCCTGGCTCGGGCTGTGTATTGTAACTCTGACATCTACCTCTTGGACGACCC 2384
mMRP1  GCGTGTGAGCCTGGCCCGGGCTGTGTACTCTAACTCTGACATCTACCTCTTTGATGACCC 2381
hMRP1  GCGCGTGAGCCTGGCCCGGGCCGTGTACTCCAACGCTGACATTTACCTCTTCGATGATCC 2577

rMRP1  CCTCTCGGCTGTGGATGCACATGTTGGGAAGCACATCTTTGAGAAGGTGGTGGGTCCCAT 2444
mMRP1  CCTCTCGGCTGTGGATGCACATGTTGGGAAGCACATCTTTGAGAAGGTGGTTGGTCCCAT 2441
hMRP1  CCTCTCAGCAGTGGATGCCCATGTGGGAAAACACATCTTTGAAAATGTGATTGGCCCCAA 2637

rMRP1  GGGCCTACTGAAGAACAAGACACGGATCCTGGTCACCCATGGTATCAGCTACCTGCCCCA 2504
mMRP1  GGGCCTACTGAAGAACAAGACACGGATCCTGGTCACCCATGGTATCAGCTACCTGCCCCA 2501
hMRP1  GGGGATGCTGAAGAACAAGACGCGGATCTTGGTCACGCACAGCATGAGCTACTTGCCGCA 2697

rMRP1  AGTGGATGTCATCATTGTCATGAGTGGCGGCAAGATCTCAGAGATGGGATCTTATCAGGA 2564
mMRP1  AGTGGATGTCATCATTGTCATGAGTGGCGGCAAGATCTCAGAGATGGGTTCTTATCAGGA 2561
hMRP1  GGTGGACGTCATCATCGTCATGAGTGGCGGCAAGATCTCTGAGATGGGCTCCTACCAGGA 2757

rMRP1  GCTGCTAGACCGGGATGGGGCCTTTGCTGAGTTCGTGCGCACCTATGCCAACACTGAGCA 2624
mMRP1  GCTGCTAGACCGGGATGGGGCCTTCGCTGAGTTCCTGCGCACCTATGCCAACGCTGAGCA 2621
hMRP1  GCTGCTGGCTCGAGACGGCGCCTTCGCTGAGTTCCTGCGTACCTATGCCAGCACAGAGCA 2817

rMRP1  GGACCTGGCTTCAGAGGATGACAGTAAGAATGGTGTCAGTGGTTTAGGGAAGGAGTCAAA 2684
mMRP1  GGACCTGGCCTCGGAGGATGACAGT---------GTCAGTGGTTCAGGGAAGGAGTCAAA 2672
hMRP1  GGAGCAGGATGCAGAGGAGAACGGGGTCACGGCGTCAGCGGTCCAGGGAAGGAAGCAAA 2877

rMRP1  GCCGGTGGAAAATGGCATACTGGTGACAGACGCAGTAGGGAAGCCCCTGCAGAGGCATCT 2744
mMRP1  GCCGGTGGAAAATGGCATGCTGGTGACAGACACCGTAGGAAAGCACCTGCAGAGGCATCT 2732
hMRP1  GCAAATGGAGAATGGCATGCTGGTGACGGACAGTGCAGGGAAGCAACTGCAGAGACAGCT 2937

rMRP1  CAGCAACTCTTCTTCCCACAGTGTGGTTACTAACCAGCAGCACAGCAGCACAAGCCGAGCT 2804
mMRP1  CAGCAACTCGTCTTCCCACAGTGGGGATACCAGCCAGCAACACAGCAGCATAGCCGAACT 2792
hMRP1  CAGCAGCTCCTCCTCCTATAGTGGGGACATCAGCAGGCACCACAACAGCACCGCAGAACT 2997

rMRP1  GCAGAAGTCTGGGGTTAAG---GAGGAGACTTGGAAGCTGATGGAAGCAGACAAGGCCCA 2861
mMRP1  GCAGAAGGCTGGAGCTAAG---GAGGAGACGTGGAAGCTAATGGAAGCAGACAAGGCCCA 2849
hMRP1  GCAGAAAGCTGAGGCCAAGAAGGAGGAGACCTGGAAGCTGATGGAGGCTGACAAGGCGCA 3057

rMRP1  GACAGGGCAGGTGAAGCTTTCCGTGTACTGGAACTACATGAAGGCCATTGGCCTCTCGCAT 2921
mMRP1  GACAGGGCAGGTGCAGCTCTCAGTGTACTGGAACTACATGAAGGCCATTGGCCTCTTCAT 2909
hMRP1  GACAGGGCAGGTCAAGCTTTCCGTGTACTGGGACTACATGAAGGCCATCGGAACTCTTCAT 3117

rMRP1  CTCCTTCTTGAGTATCTTCCTTTTCCTGTGCAATCATGTATCTTGCACTGGCTTCTAACTA 2981
mMRP1  CACCTTCTTGAGTATCTTCCTTTTCCTGTGCAACCATGTATCTTGCACTGGCCTCTAACTA 2969
hMRP1  CTCCTTCCTCAGCATCTTCCTTTTCATGTGTAACCATGTGTCCGCGCTGGCTTCCAACTA 3177

rMRP1  TTGGCTCAGTCTCTGGACAGATGACCGCCCTGCTGTCAATGGGACTCAGGAGAACAGGAA 3041
mMRP1  TTGGCTCAGCCTCTGGACAGATGACCCCCCTGTTGTCAATGGGACTCAGGCGAACAGGAA 3029
hMRP1  TTGGCTCAGCCTCTGGACTGATGACCCC---ATCGTCAACGGGACTCAGGAGCACACGAA 3234

rMRP1  TTTTCGACTAAGTGTCTATGGGGCCCTTGGGCATCTTGCAAGGTGTGCAGTATTTGGCTA 3101
mMRP1  TTTTCGGCTGAGTGTCTATGGGGCCCTTGGGCATCTTGCAAGGTGCAGCAATATTTGGCTA 3089
hMRP1  AGTCCGGCTGAGCGTCTATGGAGCCCTGGGCATTTCACAAGGGATCGCCGTGTTTGGCTA 3294

rMRP1  TTCCATGGCTGTGTCCATTGGGGGCATCTTTGCCTCCCGTCGCCTGCACCTAGACCTGCT 3161
mMRP1  CTCCATGGCTGTGTCCATCGGGGGCATCTTTGCCTCCCGTCGCTTGCACCTGGACCTGCT 3149
hMRP1  CTCCATGGCCGTGTCCATCGGGGGGATCTTGGCTTCCCGCTGTCTGCACGTGGACCTGCT 3354
```

Figure 1 (continued)

```
rMRP1  ACAGAATGTCCTGCGATCACCCATGAGTTTCTTTGAGCGTACACCCAGTGGGAACCTAGT 3221
mMRP1  ATACAATGTTCTTCGATCACCCATGAGTTTCTTCGAGCGTACACCCAGTGGGAACCTAGT 3209
hMRP1  GCACAGCATCCTGCGGTCACCCATGAGCTTCTTTGAGCGGACCCCCAGTGGGAACCTGGT 3414

rMRP1  GAACCGATTCTCCAAGGAGTTGGACACAGTGGACTCCATGATCCCGCAGGTCATCAAGAT 3281
mMRP1  GAACCGATTCTCCAAGGAGCTGGACACAGTGGACTCCATGATCCCGCAGGTCATCAAGAT 3269
hMRP1  GAACCGCTTCTCCAAGGAGCTGGACACAGTGGACTCCATGATCCCGGAGGTCATCAAGAT 3474

rMRP1  GTTCATGGGTTCACTCTTCAGTGTCATTGGAGCTGTCATCATCATCCTACTGGCTACGCC 3341
mMRP1  GTTCATGGGTTCACTCTTCAGTGTCATTGGAGCTGTCATCATCATCCTACTGGCCACGCC 3329
hMRP1  GTTCATGGGCTCCCTGTTCAACGTCATTGGTGCCTGCATCGTTATCCTGCTGGCCACGCC 3534

rMRP1  CATTGCCGCAGTCATCATCCCACCCTTGGGTCTGGTTTACTTCTTTGTGCAGAGGTTCTA 3401
mMRP1  CATTGCCGCAGTCATCATCCCACCCTTGGGTCTGGTTTACTTCTTTGTGCAGAGGTTCTA 3389
hMRP1  CATCGCCGCCATCATCATCCCGCCCCTTGGCCTCATCTACTTCTTCGTCCAGAGGTTCTA 3594

rMRP1  TGTGGCCTCCTCTCGACAGCTGAAGCGCCTGGAGTCTGTCAGTCGTTCCCCTGTGTACTC 3461
mMRP1  TGTGGCTTCCTCAAGACAACTGAAGCGCCTGGAGTCTGTCAGCCGTTCCCCTGTGTACTC 3449
hMRP1  CGTGGCTTCCTCCCGGCAGCTGAAGCGCCTCGAGTCGGTCAGCCGCTCCCCGGTCTATTC 3654

rMRP1  ACACTTCAATGAGACCTTGCTGGGGGTCAGTGTCATCCGTGCCTTTGAGGAACAGGAGCG 3521
mMRP1  ACACTTCAATGAGACCTTGCTGGGAGTCAGTGTCATCCGTGCTTTTGAGGAGCAGGAGCG 3509
hMRP1  CCATTTCAACGAGACCTTGCTGGGGGTCAGCGTCATTCGAGCCTTCGAGGAGCAGGAGCG 3714

rMRP1  CTTCATTCGCCAAAGTGACCTGAAAGTAGATGAGAACCAGAAGGCCTACTACCCCAGCAT 3581
mMRP1  CTTCATTCACCAGAGTGACCTGAAAGTAGATGAGAACCAGAAGGCCTACTACCCCAGCAT 3569
hMRP1  CTTCATCCACCAGAGTGACCTGAAGGTGGACGAGAACCAGAAGGCCTATTACCCCAGCAT 3774

rMRP1  TGTGGCCAACAGGTGGCTTGCTGTGCGCCTGGAGTGTGTGGGCAACTGCATTGTGCTGTT 3641
mMRP1  TGTGGCCAACAGATGGCTTGCTGTGCGCCTTGAGTGTGTGGGCAACTGCATTGTGCTGTT 3629
hMRP1  CGTGGCCAACAGGTGGCTGGCCGTGCGGCTGGAGTGTGTGGGCAACTGCATCGTTCTGTT 3834

rMRP1  TGCTGCCCTTTTCGCAGTCATCTCCCGGCATAGCCTCAGTGCTGGCTTGGTGGGTCTCTC 3701
mMRP1  TGCTGCCCTCTTTGCAGTCATCTCCCGGCACAGCCTCAGTGCTGGCTTGGTGGGCCTCTC 3689
hMRP1  TGCTGCCCTGTTTGCGGTGATCTCCAGGCACAGCCTCAGTGCTGGCTTGGTGGGCCTCTC 3894

rMRP1  TGTGTCTTACTCACTGCAGATAACTGCATACTTGAACTGGCTAGTTCGAATGTCCTCTGA 3761
mMRP1  TGTGTCTTACTCACTGCAGATAACTGCATACTTGAACTGGCTGGTTCGAATGTCCTCGGA 3749
hMRP1  AGTGTCTTACTCATTGCAGGTCACCACGTACTTGAACTGGCTGGTTCGGATGTCATCTGA 3954

rMRP1  GATGGAGACCAACATTGTGGCAGTGGAGAGACTGAAGGAATATTCTGAAACGGAGAAGGA 3821
mMRP1  GATGGAGACCAACATTGTGGCAGTGGAGAGACTGAAGGAGTATTCTGAAACAGAGAAGGA 3809
hMRP1  AATGGAAACCAACATCGTGGCCGTGGAGAGGCTCAAGGAGTATTCAGAGACTGAGAAGGA 3014

rMRP1  GGCTTCTTGGCAAATCCAAGAGACAGCTCCACCCAGCACCTGGCCCCATTCAGGCCGTGT 3881
mMRP1  GGCTCCTTGGCAAATCCAGGAAACAGCTCCACCCAGCACCTGGCCCCATTCAGGCCGTGT 3869
hMRP1  GGCGCCCTGGCAAATCCAGGAGACAGCTCCGCCCAGCAGCTGGCCCCAGGTGGGCCGAGT 4074

rMRP1  AGAGTTCCGGGATTACTGCTTGAGGTATCGAGAAGACTTGGACTTGGTTCTCAAGCACAT 3941
mMRP1  AGAGTTCCGGGATTACTGCCTGAGGTATCGAGAAGACTTGGACTTGGTTCTCAAGCACAT 3929
hMRP1  GGAATTCCGGAACTACTGCCTGCGCTACCGAGAGGACCTGGACTTCGTTCTCAGGCACAT 4134

rMRP1  AAATGTCACCATTGAGGGTGGAGAAAAGGTTGGTATTGTGGGTCGTACAGGAGCTGGGAA 4001
mMRP1  AAATGTCACCATTGAGGGTGGAGAAAAGGTGGGTATTGTAGGTCGTACGGGAGCTGGGAA 3989
hMRP1  CAATGTCACGATCAATGGGGGAGAAAAGGTCGGCATCGTGGGGCGGACGGGAGCTGGGAA 4194
```

Figure 1 (continued)

```
rMRP1  ATCATCTCTCACCCTGGGTTTGTTCCGGATCAATGAGTCTGCAGAAGGGGAGATCATCAT  4061
mMRP1  ATCATCTCTCACCCTGGGTTTGTTCCGGATCAATGAGTCTGCAGAAGGGGAGATCATCAT  4049
hMRP1  GTCGTCCCTGACCCTGGGCTTATTTCGGATCAACGAGTCTGCCGAAGGAGAGATCATCAT  4254

rMRP1  TGATGGCATAAACATTGCTAAGATTGGCCTGCACAACCTGCGCTTCAAGATCACCATCAT  4121
mMRP1  TGATGGGGTCAACATCGCCAAGATCGGCCTGCACAACCTGCGCTTCAAGATCACCATCAT  4109
hMRP1  CGATGGCATCAACATCGCCAAGATCGGCCTGCACGACCTCCGCTTCAAGATCACCATCAT  4314

rMRP1  TCCACAGGATCCTGTTTTGTTCCCGGGTTCCCTCCGCATGAACCTGGACCCTTTCAGTCA  4181
mMRP1  TCCACAGGATCCTGTTTTGTTCTCGGGTTCCCTCCGCATGAACTTGGACCCTTTCAGTCA  4169
hMRP1  CCCCCAGGACCCTGTTTTGTTTTCGGGTTCCCTCCGAATGAACCTGGACCCATTCAGCCA  4374

rMRP1  GTATTCTGATGAAGAAGTCTGGATGGCTCTGGAGCTTGCTCACCTGAAGGGCTTTGTGTC  4241
mMRP1  GTATTCTGATGAAGAAGTCTGGATGGCCCTGGAGCTTGCTCACCTAAAGGGCTTTGTGTC  4229
hMRP1  GTACTCGGATGAAGAAGTCTGGACGTCCCTGGAGCTGGCCCACCTGAAGGACTTCGTGTC  4434

rMRP1  AGCCTTGCCTGACAAGCTGCAACCATGAGTGTGCAGAAGGTGGAGAGAATCTGAGTGTGGG  4301
mMRP1  AGCCTTGCCTGACAAGCTGCAACCATGAGTGTGCAGAAGGTGGAGAGAACCTGAGTGTGGG  4289
hMRP1  AGCCCTTCCTGACAAGCTAGACCATGAATGTGCAGAAGGCGGGGAGAACCTCAGTGTCGG  4494

rMRP1  GCAGCGACAGCTTGTGTGCCTGGCCCGGGCTTTGCTGAGGAAGACAAAGATTCTAGTGTT  4361
mMRP1  GCAGCGACAGCTTGTGTGCCTGGCCCGGGCTCTGCTGAGGAAGACAAAGATTCTAGTGTT  4349
hMRP1  GCAGCGCCAGCTTGTGTGCCTAGCCCGGGCCCTGCTGAGGAAGACGAAGATCCTTGTGTT  4554

rMRP1  GGACGAGGCTACAGCAGCTGTGGATCTGGAGACAGATGACCTTATTCAGTCCACCGTCCG  4421
mMRP1  GGACGAGGCTACCGCAGCTGTGGACCTAGAGACAGATAACCTTATCCAGTCCACCATCCG  4409
hMRP1  GGATGAGGCCACGGCAGCCGTGGACCTGGAAACGGACGACCTCATCCAGTCCACCATCCG  4614

rMRP1  GACGCAGTTTGAAGACAGTACTGTGCTCACTATTGCTCATCGGCTGAATACCATAATGGA  4481
mMRP1  GACGCAGTTTGAAGACTGTACTGTGCTCACGATTGCTCATCGGCTTAACACCATAATGGA  4469
hMRP1  GACACAGTTCGAGGACTGCACCGTCCTCACCATCGCCCACCGGCTCAACACCATCATGGA  4674

rMRP1  CTATACAAGGGTGATTGTCCTGGACAAAGGAGAAATTCGGGAGTGTGGTGCACCCTCTGA  4541
mMRP1  CTACACACGGGTTATTGTCCTGGACAAAGGAGAAGTTCGGGAGTGTGGTGCACCCTCTGA  4529
hMRP1  CTACACAAGGGTGATCGTCTTGGACAAAGGAGAAATCCAGGAGTACGGCGCCCCATCGGA  4734

rMRP1  GCTCCTGCAGCAAAGAGGCGTCTTCTATAGCATGGCCAAGGATGCTGGCTTGGTGTGA--  4599
mMRP1  GCTCCTGCAGCAAAGAGGCATCTTCTACAGCATGGCCAAGGATGCTGGCTTGGTGTGA--  4587
hMRP1  CCTCCTGCAGCAGAGAGGTCTTTTCTACAGCATGGCCAAAGACGCCGGCTTGGTGTGAGC  4794

rMRP1  ------------------------------------------------------------  4599
mMRP1  ------------------------------------------------------------  4587
hMRP1  CCCAGAGCTGGCATATCTGGTCAGAACTGCAGGGCCTATATGCCAGCGCCCAGGGAGGAG  4854

rMRP1  ------------------------------------------------------------  4599
mMRP1  ------------------------------------------------------------  4587
hMRP1  TCAGTACCCCTGGTAAACCAAGCCTCCCACACTGAAACCAAAACATAAAAACCAAACCCA  4914

rMRP1  ------------------------------------------------------------  4599
mMRP1  ------------------------------------------------------------  4587
hMRP1  GACAACCAAAACATATTCAAAGCAGCAGCCACCGCCATCCGGTCCCCTGCCTGGAACTGG  4974

rMRP1  -------------------------------------  4599
mMRP1  -------------------------------------  4587
hMRP1  CTGTGAAGACCCAGGAGAGACAGAGATGCGAACCACC  5011
```

Figure 6

A B C
apical
basolateral

Figure 16

A: Human MDR1 wild-type protein amino acid sequence (SEQ ID NO:4)

```
   1 MDLEGDRNGGAKKKNFFKLNNKSEKDKKEKKPTVSVFSMFRYSNWLDKLYMVVGTLAAII
  61 HGAGLPLMMLVFGEMTDIFANAGNLEDLMSNITNRSDINDTGFFMNLEEDMTRYAYYYSG
 121 IGAGVLVAAYIQVSFWCLAAGRQIHKIRKQFFHAIMRQEIGWFDVHDVGELNTRLTDDVS
 181 KINEVIGDKIGMFFQSMATFFTGFIVGFTRGWKLTLVILAISPVLGLSAAVWAKILSSFT
 241 DKELLAYAKAGAVAEEVLAAIRTVIAFGGQKKELERYNKNLEEAKRIGIKKAITANISIG
 301 AAFLLIYASYALAFWYGTTLVLSGEYSIGQVLTVFFSVLIGAFSVGQASPSIEAFANARG
 361 AAYEIFKIIDNKPSIDSYSKSGHKPDNIKGNLEFRNVHFSYPSRKEVKILKGLNLKVQSG
 421 QTVALVGNSGCGKSTTVQLMQRLYDPTEGMVSVDGQDIRTINVRFLREIIGVVSQEPVLF
 481 ATTIAENIRYGRENVTMDEIEKAVKEANAYDFIMKLPHKFDTLVGERGAQLSGGQKQRIA
 541 IARALVRNPKILLLDEATSALDTESEAVVQVALDKARKGRTTIVIAHRLSTVRNADVIAG
 601 FDDGVIVEKGNHDELMKEKGIYFKLVTMQTAGNEVELENAADESKSEIDALEMSSNDSRS
 661 SLIRKRSTRRSVRGSQAQDRKLSTKEALDESIPPVSFWRIMKLNLTEWPYFVVGVFCAII
 721 NGGLQPAFAIIFSKIIGVFTRIDDPETKRQNSNLFSLLFLALGIISFITFFLQGFTFGKA
 781 GEILTKRLRYMVFRSMLRQDVSWFDDPKNTTGALTTRLANDAAQVKGAIGSRLAVITQNI
 841 ANLGTGIIISFIYGWQLTLLLLAIVPIIAIAGVVEMKMLSGQALKDKKELEGAGKIATEA
 901 IENFRTVVSLTQEQKFEHMYAQSLQVPYRNSLRKAHIFGITFSFTQAMMYFSYAGCFRFG
 961 AYLVAHKLMSFEDVLLVFSAVVFGAMAVGQVSSFAPDYAKAKISAAHIIMIIEKTPLIDS
1021 YSTEGLMPNTLEGNVTFGEVVFNYPTRPDIPVLQGLSLEVKKGQTLALVGSSGCGKSTVV
1081 QLLERFYDPLAGKVLLDGKEIKRLNVQWLRAHLGIVSQEPILFDCSIAENIAYGDNSRVV
1141 SQEEIVRAAKEANIHAFIESLPNKYSTKVGDKGTQLSGGQKQRIAIARALVRQPHILLLD
1201 EATSALDTESEKVVQEALDKAREGRTCIVIAHRLSTIQNADLIVVFQNGRVKEHGTHQQL
1261 LAQKGIYFSMVSVQAGTKRQ
```

B: Human MDR1 wild-type gene nucleotide sequence (cDNA) (SEQ ID NO:5)

```
   1 cctactctat tcagatattc tccagattcc taaagattag agatcatttc tcattctcct
  61 aggagtactc acttcaggaa gcaaccagat aaaagagagg tgcaacggaa gccagaacat
 121 tcctcctgga aattcaacct gtttcgcagt ttctcgagga atcagcattc agtcaatccg
 181 ggccgggagc agtcatctgt ggtgaggctg attggctggg caggaacagc gccggggcgt
 241 gggctgagca cagcgcttcg ctctctttgc cacaggaagc ctgagctcat tcgagtagcg
 301 gctcttccaa gctcaaagaa gcagaggccg ctgttcgttt cctttaggtc tttccactaa
 361 agtcggagta tcttcttcca agatttcacg tcttggtggc cgttccaagg agcgcgaggt
 421 cgggatggat cttgaagggg accgcaatgg aggagcaaag aagaagaact tttttaaact
 481 gaacaataaa agtgaaaaag ataagaagga aaagaaacca actgtcagtg tattttcaat
 541 gtttcgctat tcaaattggc ttgacaagtt gtatatggtg gtgggaactt tggctgccat
 601 catccatggg gctggacttc ctctcatgat gctggtgttt ggagaaatga cagatatctt
 661 tgcaaatgca ggaaatttag aagatctgat gtcaaacatc actaatagaa gtgatatcaa
 721 tgatacaggg ttcttcatga atctggagga agacatgacc aggtatgcct attattacag
 781 tggaattggt gctggggtgc tggttgctgc ttacattcag gtttcatttt ggtgcctggc
 841 agctggaaga caaatacaca aaattagaaa acagtttttt catgctataa tgcgacagga
 901 gataggctgg tttgatgtgc acgatgttgg ggagcttaac acccgactta cagatgatgt
 961 ctctaagatt aatgaagtta ttggtgacaa aattggaatg ttctttcagt caatggcaac
1021 atttttcact gggtttatag taggatttac acgtggttgg aagctaaccc ttgtgatttt
1081 ggccatcagt cctgttcttg gactgtcagc tgctgtctgg gcaaagatac tatcttcatt
1141 tactgataaa gaactcttag cgtatgcaaa agctggagca gtagctgaag aggtcttggc
1201 agcaattaga actgtgattg catttggagg acaaaagaaa gaacttgaaa ggtacaacaa
1261 aaatttagaa gaagctaaaa gaattgggat aaagaaagct attacagcca atatttctat
1321 aggtgctgct ttcctgctga tctatgcatc ttatgctctg gccttctggt atgggaccac
1381 cttggtcctc tcaggggaat attctattgg acaagtactc actgtattct tttctgtatt
```

Figure 16 (continued)

```
1441 aattggggct tttagtgttg gacaggcatc tccaagcatt gaagcatttg caaatgcaag
1501 aggagcagct tatgaaatct tcaagataat tgataataag ccaagtattg acagctattc
1561 gaagagtggg cacaaaccag ataatattaa gggaaatttg gaattcagaa atgttcactt
1621 cagttaccca tctcgaaaag aagttaagat cttgaagggc ctgaacctga aggtgcagag
1681 tgggcagacg gtggccctgg ttggaaacag tggctgtggg aagagcacaa cagtccagct
1741 gatgcagagg ctctatgacc ccacagaggg gatggtcagt gttgatggac aggatattag
1801 gaccataaat gtaaggtttc tacgggaaat cattggtgtg gtgagtcagg aacctgtatt
1861 gtttgccacc acgatagctg aaaacattcg ctatggccgt gaaaatgtca ccatggatga
1921 gattgagaaa gctgtcaagg aagccaatgc ctatgacttt atcatgaaac tgcctcataa
1981 atttgacacc ctggttggag agagaggggc ccagttgagt ggtgggcaga agcagaggat
2041 cgccattgca cgtgccctgg ttcgcaaccc caagatcctc ctgctggatg aggccacgtc
2101 agccttggac acagaaagcg aagcagtggt tcaggtggct ctggataagg ccagaaaagg
2161 tcggaccacc attgtgatag ctcatcgttt gtctacagtt cgtaatgctg acgtcatcgc
2221 tggtttcgat gatggagtca ttgtggagaa aggaaatcat gatgaactca tgaaagagaa
2281 aggcatttac ttcaaacttg tcacaatgca gacagcagga aatgaagttg aattagaaaa
2341 tgcagctgat gaatccaaaa gtgaaattga tgccttggaa atgtcttcaa atgattcaag
2401 atccagtcta ataagaaaaa gatcaactcg taggagtgtc cgtggatcac aagcccaaga
2461 cagaaagctt agtaccaaag aggctctgga tgaaagtata cctccagttt ccttttggag
2521 gattatgaag ctaaatttaa ctgaatggcc ttattttgtt gttggtgtat tttgtgccat
2581 tataaatgga ggcctgcaac cagcatttgc aataatattt tcaaagatta taggggtttt
2641 tacaagaatt gatgatcctg aaacaaaacg acagaatagt aacttgtttt cactattgtt
2701 tctagccctt ggaattattt cttttattac atttttcctt cagggtttca catttggcaa
2761 agctggagag atcctcacca agcggctccg atacatggtt ttccgatcca tgctcagaca
2821 ggatgtgagt tggtttgatg accctaaaaa caccactgga gcattgacta ccaggctcgc
2881 caatgatgct gctcaagtta aaggggctat aggttccagg cttgctgtaa ttacccagaa
2941 tatagcaaat cttgggacag gaataattat atccttcatc tatggttggc aactaacact
3001 gttactctta gcaattgtac ccatcattgc aatagcagga gttgttgaaa tgaaaatgtt
3061 gtctggacaa gcactgaaag ataagaaaga actagaaggt gctgggaaga tcgctactga
3121 agcaatagaa aacttccgaa ccgttgtttc tttgactcag gagcagaagt ttgaacatat
3181 gtatgctcag agtttgcagg taccatacag aaactctttg aggaaagcac acatctttgg
3241 aattacattt tccttcaccc aggcaatgat gtatttttcc tatgctggat gtttccggtt
3301 tggagcctac ttggtggcac ataaactcat gagctttgag gatgttctgt tagtattttc
3361 agctgttgtc tttggtgcca tggccgtggg gcaagtcagt tcatttgctc ctgactatgc
3421 caaagccaaa atatcagcag cccacatcat catgatcatt gaaaaaaccc ctttgattga
3481 cagctacagc acggaaggcc taatgccgaa cacattggaa ggaaatgtca catttggtga
3541 agttgtattc aactatccca cccgaccgga catcccagtg cttcagggac tgagcctgga
3601 ggtgaagaag ggccagacgc tggctctggt gggcagcagt ggctgtggga agagcacagt
3661 ggtccagctc ctggagcggt tctacgaccc cttggcaggg aaagtgctgc ttgatggcaa
3721 agaaataaag cgactgaatg ttcagtggct ccgagcacac ctgggcatcg tgtcccagga
3781 gcccatcctg tttgactgca gcattgctga gaacattgcc tatggagaca acagccgggt
3841 ggtgtcacag gaagagatcg tgagggcagc aaaggaggcc aacatacatg ccttcatcga
3901 gtcactgcct aataaatata gcactaaagt aggagacaaa ggaactcagc tctctggtgg
3961 ccagaaacaa cgcattgcca tagctcgtgc ccttgttaga cagcctcata ttttgctttt
4021 ggatgaagcc acgtcagctc tggatacaga aagtgaaaag gttgtccaag aagccctgga
4081 caaagccaga gaaggccgca cctgcattgt gattgctcac cgcctgtcca ccatccagaa
4141 tgcagactta atagtggtgt ttcagaatgg cagagtcaag gagcatggca cgcatcagca
4201 gctgctggca cagaaaggca tctatttttc aatggtcagt gtccaggctg gaacaaagcg
4261 ccagtgaact ctgactgtat gagatgttaa atacttttta atatttgttt agatatgaca
4321 tttattcaaa gttaaaagca aacacttaca gaattatgaa gaggtatctg tttaacattt
4381 cctcagtcaa gttcagagtc ttcagagact tcgtaattaa aggaacagag tgagagacat
4441 catcaagtgg agagaaatca tagtttaaac tgcattataa attttataac agaattaaag
4501 tagattttaa aagataaaat gtgtaatttt gtttatattt tcccatttgg actgtaactg
4561 actgccttgc taaaagatta tagaagtagc aaaaagtatt gaaatgtttg cataaagtgt
4621 ctataataaa actaaacttt catgtg
```

SEQUENCE VARIANTS OF MULTI-DRUG RESISTANCE GENES, MDR1 AND MRP1, AND METHODS FOR ASSESSMENT OF DRUG PENETRATION AND DISPOSITION

CROSS REFERENCES TO RELATED APPLICATIONS

The present application claims priority to U.S. Provisional Patent Application No. 60/539,362, filed Jan. 26, 2004, the entire disclosure of which is incorporated by reference herein.

STATEMENT AS TO RIGHTS TO INVENTIONS MADE UNDER FEDERALLY SPONSORED RESEARCH AND DEVELOPMENT

This research was supported by National Institutes of Health grants GM 62883, AI-52663, NS39178, AI31854, ES07033 and HL56548 and by NIH Pharmaceutical Sciences Training Grant GM07750.

BACKGROUND OF THE INVENTION

Transporter proteins constitute a significant fraction of membrane-bound proteins, which account for approximately 30% of total proteins found in humans. About half of the membrane-bound transporters reported to date have been discovered within the past 5 years. The role of membrane transporters located in various organs and tissues in drug delivery and their disposition in vivo is just beginning to be appreciated. For example, a major challenge in clinical pharmacology is to elucidate the often observed, wide inter-individual variability in pharmacokinetics. Recently, Greiner et al. (*J. Clin. Invest.* 104:147 (1999)) demonstrated an inter-individual variation in the intestinal expression of the multidrug resistance transporter protein, MDR1 or P-glycoprotein, that resulted in a 7-fold range in the oral bioavailability of a P-glycoprotein (pgp) substrate, digoxin, in healthy human subjects. Therefore, it is important to understand the role of transporters in the disposition of currently available drugs, as well as to develop the capability of predicting the contribution of membrane transporters in the disposition of new molecular entities under development.

There are two well-characterized major ATP-binding cassette (ABC) superfamily members, ABC-B and ABC-C, involved in conferring drug resistance to cancer cells (Higgins, *Annu. Rev. Cell. Biol.* 8:67-113 (1992); Wijnholds, *Novartis Found. Symp.* 243:69-79, discussion 80-2, 180-5 (2002). Within these two families, two protein isoforms, one from each family, play a critical role in drug resistance. They are P-glycoprotein (Pgp or MDk1), which belongs to the ABC-B family (Gottesman and Pastan, *Annu. Rev. Biochem.* 62:385-427 (1993)), and MRP1, which belongs to the ABC-C family (Cole et al., *Cancer Res.* 54(22): 5902-10 (1994)). Pgp is the most extensively studied ATP-binding cassette transporter, functioning as a biological barrier by extruding toxic substances and xenobiotics out of the cells. In the clinical setting, the over-expression of multidrug resistance proteins such as MDR1 or MRP1 is often associated with poor prognosis for cancer patients.

Progress has been made in understanding of the structure-function relationship of some of the major drug transporters in recent years, notably the ABC transporters, and ABCB1 or MDR1 in particular. While certain amino acid residues in the drug and co-substrate (nucleotide) binding domains and those involved in the anchoring of the membrane-spanning polypeptides have been identified through site-directed mutagenesis and single nucleotide polymorphism studies, the actual biophysical mechanism of solute translocation is far from being elucidated.

The human MDR1 gene encodes a 170 kilodalton integral membrane protein that mediates ATP-dependent substrate efflux. The protein product, P-glycoprotein, a member of the ATP-binding cassette (ABC) superfamily of transporters, resides in the plasma membrane and functions as an efflux transporter of a wide variety of natural compounds and lipophilic xenobiotics. While the contribution of P-glycoprotein in multidrug resistance for cancer chemotherapy is well documented, the role of P-glycoprotein in drug disposition is not fully understood and has continued to generate significant debate. P-glycoprotein mediates the energy-dependent efflux of a broad range of xenobiotics in epithelial tissues throughout the human body including the intestinal mucosa, liver canalicular membrane, kidney proximal tubules, blood-brain-barrier, and placenta. (Schinkel, *Semin. Cancer Biol.* 8:161-70 (1997)). Because P-glycoprotein is found in tissues important in drug disposition, variation in expression and function of P-glycoprotein due to genetic polymorphisms of MDR1 may influence pharmacokinetics and, in turn, pharmacodynamics.

Despite some similarities in drug resistance profiles, the MDR1 and MRP1 transporters differ somewhat in substrate selectivity, molecular structure, tissue distribution, and membrane location in cells. At the genetic level, MDR1 and MRP1 are only 15% identical in their amino acid sequences (Kruh et al., *J. Bioenerg. Biomembr.* 33(6): 493-501 (2001)). MRP1 is capable of transporting many lipophilic anions and conjugated substances. The MRP1 substrate includes a variety of structurally diverse anticancer drugs, GSH-conjugates, glucuronides, leukotriene C4 (LTC4), unmodified drugs, and some drugs that are multivalent organic anions, while Pgp substrates are mostly natural or mildly cationic molecules. A few previous studies (Paul et al., *Biochem.* 35(42): 13647-55 (1996); Stride et al., *Mol. Pharmacol.* 52(3): 344-53 (1997); Zh al. *J. Biol. Chem.* 276(16): 13231-9 (2001)) suggest that there are differences in substrate recognition and transport activity between the mouse and human ortholog of MRP1, indicating that significant interspecies differences exist for MRP1.

In rat, only a few reports are available for MRPs. It has been shown that the rat MRP1 expression occurs in almost all tissues, and its over-expression could confer multidrug resistance in cancer cells (Cherrington et al., *J. Pharmacol. Exp. Ther.* 300(1): 97-104 (2002)). Expression of rat MRP1 in the BBB capillary system and placenta has also been reported (Regina et al., *J. Neurochem.* 71(2):705-15 (1998)), suggesting that MRP1 plays certain roles in drug distribution into the central nervous system and in drug exchanges between the mother and fetus.

There are significant challenges in elucidating the functioning of transporters at the cellular and organ levels. Several reviews (Kunta and Sinko, *Curr. Drug Metab.* 5:109-124 (2004); van Montfoort et al., *Curr. Drug Metab.* 4:185-211 (2003)) have emphasized the concerted action of apical and basolateral membrane transporters in the translocation of a solute across epithelial barriers. The directionality of transport often requires carefully controlled studies with a cell barrier model. While cell barrier models for the intestinal and renal tubular epithelia are well-validated (e.g., Caco-2 LLC-PK1 and MDCK) and generally adopted, such models are still not available for the blood-brain barrier, the placenta, and the nasal and bronchial epithelia for direct evaluation of individual transporter proteins of interest such as MDR1 product Pgp and its genetic variants.

Research advances on the pharmacogenetics of human drug-metabolizing enzymes over the past two decades have afforded valuable insights into the clinical pharmacokinetics of a wide range of drugs, which have in turn led to clearer understanding of the metabolic basis of drug interactions and individual susceptibility to drug toxicities. It has had a profound impact on drug development and regulation.

The same impact may be observed as progress is made toward better understanding of the functional impact of genetic variations with polymorphically-expressed drug transporters. The genetic complexity of transporter genes is just beginning to be understood (see, e.g., Woodahl and Ho, *Curr. Drug Metab.* 5:11-19 (2004)). Linking the genetic polymorphism to a clinically discemable phenotype is complicated by linkage disequilibrium among single nucleotide polymorphisms. Improvement in molecular genetic technologies that could validate computational approaches that are currently used to assign and predict haplotypes could make a significant contribution in this area. Beyond the constitutive gene expression are issues related to gene regulation, such as induction and suppression of transporter gene transcription by endo- and xenobiotics, tissue-specific regulation through alternate splicing and post-translational modification, and modulation by diseases or pathophysiology.

Improved knowledge of drug transporters will optimize the delivery of a drug molecule to the target site(s) of interest. Discovery of new genetic variants of MDR1 that may have significant impact on drug penetration to cell and tissues as well as the availability of validated in vitro tools to predict drug availability and potential interactions with drugs that are given concomitantly could provide a significant improvement accelerating drug development and improve drug safety.

SUMMARY OF THE INVENTION

In one aspect, the present invention provides a method for predicting responsiveness to a drug in a subject, where subject has a disease or disorder amenable to treatment with the drug and the drug is a substrate of MDR1. The method generally includes the following steps: (1) isolating a biological sample that includes nucleic acids and/or proteins from the subject; and (2) analyzing the biological sample to determine (a) the nucleotide at position 1199 of the MDR1 gene, and/or (b) the presence or absence of the S400I variant of MDR1 protein; whereby the presence of T at nucleotide position 1199 or the presence of the S400I MDR1 variant is indicative of an increased responsiveness to the drug in the subject relative an individual that is homozygous for a wild-type MDR1 gene. In typical embodiments, the biological sample includes nucleic acids and the analyzing step comprises determining the nucleotide present at position 1199 of the MDR1 gene. A particularly suitable technique for analyzing the nucleic acids in the sample includes hybridization between the nucleic acid sample and a nucleic acid that is either (a) a nucleic acid including about 10 to about 100 contiguous nucleotides of a G1199T variant of the nucleotide sequence set forth in SEQ ID NO:5, where the nucleic acid includes the nucleotide at position 1199 and/or a base adjacent thereto, or (b) a nucleic acid that is fully complementary-to the nucleic acid of (a). In certain variations, the drug is a cytotoxic chemotherapeutic agent such as, e.g., doxorubicin, paclitaxol, vinblastine, and vincristine.

In another aspect, the present invention provides a method for predicting oral bioavailability of an HIV protease inhibitor in a subject, where the HIV protease inhibitor is a substrate of MDR1. The method generally includes the following steps: comprising: (1) isolating a biological sample that includes nucleic acids and/or proteins from the subject; and (2) analyzing the biological sample to determine (a) the nucleotide at position 1199 of the MDR1 gene, and/or (b) the presence or absence of the S400N variant of MDR1 protein, whereby the presence of A at nucleotide position 1199 or the presence of the S400N variant is indicative of a decreased oral bioavailability of the HIV protease inhibitor in the subject relative an individual that is homozygous for a wild-type MDR1 gene. In typical embodiments, the biological sample includes nucleic acids and the analyzing step comprises determining the nucleotide present at position 1199 of the MDR1 gene. A particularly suitable technique for analyzing the nucleic acids in the sample includes hybridization between the nucleic acid sample and a nucleic acid that is either (a) a nucleic acid including about 10 to about 100 contiguous nucleotides of a G1199A variant of the nucleotide sequence set forth in SEQ ID NO:5, where the nucleic acid includes the nucleotide at position 1199 and/or a base adjacent thereto, or (b) a nucleic acid that is fully complementary to the nucleic acid of (a). Exemplary HIV protease inhibitors amenable to prediction of oral biovailability in accordance with the above method include, e.g., amprenavir, indinavir, lopinavir, ritonavir, and saquinavir. In certain variations, the method further includes selecting a mode of administration for the HIV protease inhibitor based on whether a decreased oral bioavailability is indicated.

In certain embodiments of the present invention, the above methods further include determining the MDR1 genotype at nucleotide position 1199 of the MDR1 gene.

In yet another aspect, the present invention provides an isolated nucleic acid that is (a) a nucleic acid that includes at least 15 contiguous nucleotides of a variant of the nucleotide sequence set forth in SEQ ID NO:5, where (i) the variant is A163C and the nucleic acid includes the nucleotide at position 163; (ii) the variant is A886C and the nucleic acid includes the nucleotide at position 886; (iii) the variant is G1199T and the nucleic acid includes the nucleotide at position 1199; (iv) the variant is G1292T/T1293G and the nucleic acid includes at least one of the nucleotide at position 1292 and the nucleotide at position 1293; (v) the variant is T2814G and the nucleic acid includes the nucleotide at position 2814; (vi) the variant is C3258T and the nucleic acid includes the nucleotide at position 3258; or (vii) the variant is G3271C and the nucleic acid includes the nucleotide at position 3271; or (b) a nucleic acid that is fully complementary to the nucleic acid of (a). In certain embodiments, the nucleic acid encodes the corresponding variant MDR1 protein or a fragment thereof having MDR1 activity. The present invention also provides an expression vector that includes any one of the above nucleic acids.

In still another aspect, the present invention provides an isolated MDR1 protein that is a variant of the wild-type MDR1 protein having the amino acid sequence set forth in SEQ ID NO:4, in which the MDR1 variant has at least one of the following amino acid substitutions: T55P, N296H, S400I, C431L, F938L, and A1091P. In one specific embodiment, the isolated MDR1 has the S400I amino acid substitution.

Also provided is an isolated cell line expressing an MDR1 protein as set forth above. In certain embodiments, the isolated cell line is a stable recombinant cell line (such as, e.g., a stably transformed epithelial cell line) that comprises the expression vector that includes a nucleic acid as set forth above. In specific variation, the cell line expresses an MDR1 variant having the S400I amino acid substitution.

In another aspect, the present invention provides a method for evaluating the influence of a MDR1 polymorphism on MDR1 mediated efflux, uptake, or transcellular transport, the method including the following steps: (1) contacting a first cell with a therapeutic agent, where the first cell expresses an MDR1 variant having at least one amino acid substitution selected from T55P, N296H, S400I, C431L, F938L, and A1091P; (2) contacting a control cell with the therapeutic agent, where the control cell expresses the wild type MDR1 protein; (3) culturing the first cell and control cell; (4) determining for each of the first cell and control cell at least one of the uptake, efflux, or transcellular transport of the therapeutic agent; and (5) comparing the level of uptake, efflux, or transcellular transport of the therapeutic agent in the first cell with that of the control cell.

In yet another aspect, the present invention provides a stably transformed cell line capable of transcellular transport and comprising a non-viral vector encoding and expressing a recombinant mammalian MRP1 or MDR1 protein, or a homolog thereof. In certain embodiments, the cell line is an epithelial cell line such as, e.g., a renal or intestinal epithelial cell line. In specific variations, the cell line is LLC-PK1, MDCKII, or Caco-2.

Still further, the present invention provides methods for using the foregoing cell line. For example, in one embodiment, a method for evaluating the contribution of an MRP1 or MDR1 protein to the disposition or penetration of an agent is provided that includes contacting the cell line (capable of transcellular transport and comprising a non-viral vector encoding and expressing a recombinant mammalian MRP1 or MDR1 protein, or a homolog thereof) with the agent; culturing the contacted cell line; and determining at least one of the uptake, efflux, or transcellular transport of the agent. In another embodiment, a method for evaluating the influence of a MDR1 or MRP1 polymnorphism on MDR1- or MRP1-mediated efflux, uptake, or transcellular transport, is provided that includes the following steps: (1) contacting a first cell (capable of transcellular transport and comprising a non-viral vector encoding and expressing a recombinant mammalian MRP1 or MDR1 protein, or a homolog thereof) with a therapeutic agent, where the recombinant MRP1 or MDR1 protein expressed in the first cell is an allelic variant of a wild-type MRP1 or MDR1 protein; (2) contacting a control cell with the therapeutic agent, where the control cell expresses the wild type MRP1 or MDR1 protein corresponding to the allelic variant; (3) culturing the first cell and control cell; (4) determining for each of the first cell and control cell at least one of the uptake, efflux, or transcellular transport of the therapeutic agent; and (5) comparing the level of uptake, efflux, and/or transcellular transport of the therapeutic agent in the first cell with that of the control cell.

DEFINITIONS

Unless defined otherwise, all technical and scientific terms used herein have the same meaning as commonly understood by one of ordinary skill in the art to which this invention belongs. Although any methods and materials similar to those described herein can be used in the practice or testing of the present invention, only exemplary methods and materials are described. For purposes of the present invention, the following terms are defined below.

The terms "a," "an," and "the" include plural referents unless the context clearly dictates otherwise.

An "agent" refers to any molecule with a potential to structurally interact with biomolecules, particularly proteins, through non-covalent interactions, such as, for example, through hydrogen bonds, ionic bonds, van der Waals attractions, or hydrophobic interactions. Agents include, for example, small molecules, nucleic acids, peptides, peptidomimetics, synthetic compounds, and/or natural compounds. Agents include drugs or pharmaceutical agents. A "drug," "pharmaceutical agent," or "therapeutic agent" means any substance used in the prevention, diagnosis, alleviation, treatment or cure of a disease, or which is in development for such use, including drugs undergoing testing in animal studies or clinical trials in humans.

"Amenable to treatment" with a drug means that a disorder or disease is either predicted or determined to be a disorder or disease that can be treated by administration of the drug (for example, through clinical testing such as by, e.g., clinical trials conducted to obtain governmental approval of a drug).

As used herein, the term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. The term "nucleic acid" encompasses the terms "oligonucleotide" and "polynucleotide." The term "oligonucleotide" refers to at least one molecule of between about 3 and about 100 bases in length. The term "polynucleotide" refers to at least one molecule of greater than about 100 bases in length. Unless otherwise indicated, a particular nucleic acid sequence includes the complementary sequence thereof.

As used herein, the term "promoter" refers to a control sequence that controls the initiation and rate of transcription. A promoter can contain genetic elements at which regulatory proteins and molecules bind, such as RNA polymerase and other transcription factors, to initiate the specific transcription of a nucleic acid sequence. A promoter can also include an enhancer. The phrases "operatively positioned," "operatively linked," and "operatively associated" mean that a promoter is in a correct functional location and/or orientation in relation to a nucleic acid sequence to control transcriptional initiation and/or expression of a downstream sequence.

As used herein, "wild-type gene" refers to a sequence of nucleic acid, at a genetic locus in the genome of an organism, that encodes a gene product that performs the normal function of the gene product encoded by a naturally occurring nucleotide sequence corresponding to the genetic locus. A genetic locus can have more than one sequence or allele in a population of individuals, and the term "wild-type" encompasses all such naturally-occurring alleles that encode a gene product performing the normal function. "Wild-type" also encompasses gene sequences that are not necessarily naturally occurring, but that still encode a gene product with normal function (e.g., genes having silent mutations or encoding proteins with conservative substitutions).

The term "wild-type" with reference to an MDR1 polypeptide or peptide means an MDR1 polypeptide or peptide encoded by a wild-type MDR1 gene. A genetic locus can have more than one sequence or allele in a population of individuals, and the term "wild-type" encompasses all such naturally-occurring alleles that encode a gene product performing the normal function. In addition to naturally-occurring amino acid sequence variants having normal function, wild-type MDR1 polypeptides include derivatives altered by substitution, addition or deletion of one or more amino acid residues that provide for molecules having normal MDR1 function.

As used herein, the terms "polypeptide," "peptide" and "protein" are used interchangeably herein to refer to polymer of amino acid residues of varying lengths. A "fragment" of a protein typically comprises or consists of at least 8-10 contiguous amino acids. In other embodiments, the fragment comprises at least 20 or at least 50 contiguous amino acids. In other embodiments, the fragments are not larger than 35, 100, or 200 amino acids. A derivative is a polypeptide having conservative amino acid substitutions, as compared with another sequence. Derivatives further include, for example, glycosylations, acetylations, phosphorylations, and the like. Further included within the definition of "polypeptide" are, for example, polypeptides containing one or more analogs of an amino acid (e.g., unnatural or "non-classical" amino acids, and the like), polypeptides with substituted linkages as well as other modifications known in the art, both naturally and non-naturally occurring.

As used herein, the term "polymorphic" means that multiple variants exists (i.e., two or more alleles exist) at a genetic locus in the individuals of a population. A "polymorphism" refers to a mutation present in 1% or more of alleles of the general population.

As used herein, a "homolog" of a first gene refers to a second, different gene that is substantially identical to the first gene, or that encodes a gene product that is substantially identical to the gene product encoded by the first gene. An "ortholog" of a first gene refers to a second gene from a different organism that is substantially identical to the first gene, or that encodes a gene product that is substantially identical or substantially identical to the gene product encoded by the first gene.

The term "isolated" refers to nucleic acid, protein, polypeptide or fragment thereof that has been removed from its natural cellular environment.

The term "cell line," as used herein, refers to individual cells, harvested cells, and cultures containing the cells (e.g., in vitro), so long as they are derived from cells of the cell line referred to. A cell line is said to be "continuous," "immortal," or "stable" if the line remains viable over a prolonged time, typically at least about six months. To be considered a cell line, as used herein, the cells typically remains viable for at least 50 passages. A "primary cell line," or "normal cell line," in contrast, refers to cells that do not remain viable over a prolonged time in culture.

BRIEF DESCRIPTION OF THE DRAWINGS

FIG. 1: Novel cDNA sequence encoding rat MRP1. Rat (SEQ ID NO: 1), mouse (SEQ ID NO:2), and human (SEQ ID NO:3) MRP1 cDNA sequence alignment.

FIG. 6: Confirmation of apical membrane expression of P-glycoprotein by deconvolution immunofluorescent microscopy in recombinant $MDR1_{wt}$ and $MDR1_{1199}$ cells. LLC-PK1 control cells (panel A), $MDR1_{wt}$ cells (panel B), and $MDR1_{1199}$ cells (panel C) plated on glass slides. The cells are orientated such that the apical membrane is on top and the basolateral membrane is on bottom.

FIG. 3: Cells were seeded at 1E4 cells per well on Day-1 in a 96 well plate. Doxorubicin or Ivermectin were added at varying concentrations on Day 0. After 72 hours, the MTS assay was performed and values were % growth compared to no drug control. (HEK •; WT○; G1199A▼; G1199T■)

Figure 14:
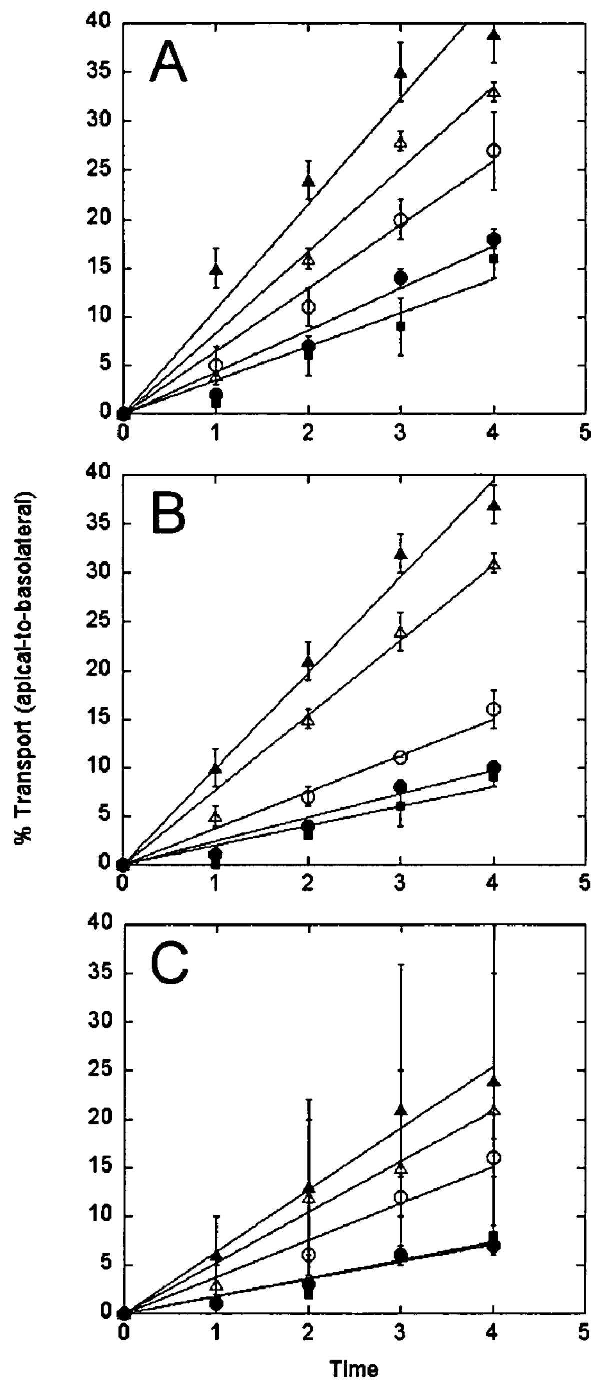

FIG. 14: Apical-to-basolateral efflux transport of HIV protease inhibitors in the presence of GF120918. Transepithelial permeability was evaluated as the percent transport of protease inhibitors across an epithelial monolayer; LLC-PK1 control cells (panel A); $MDR1_{wt}$ cells (panel B); and $MDR1_{1199}$ cells (panel C). Transport of amprenavir (▲), indinavir (●), lopinavir (Δ), ritonavir (○), and saquinavir (■).

Figure 15:
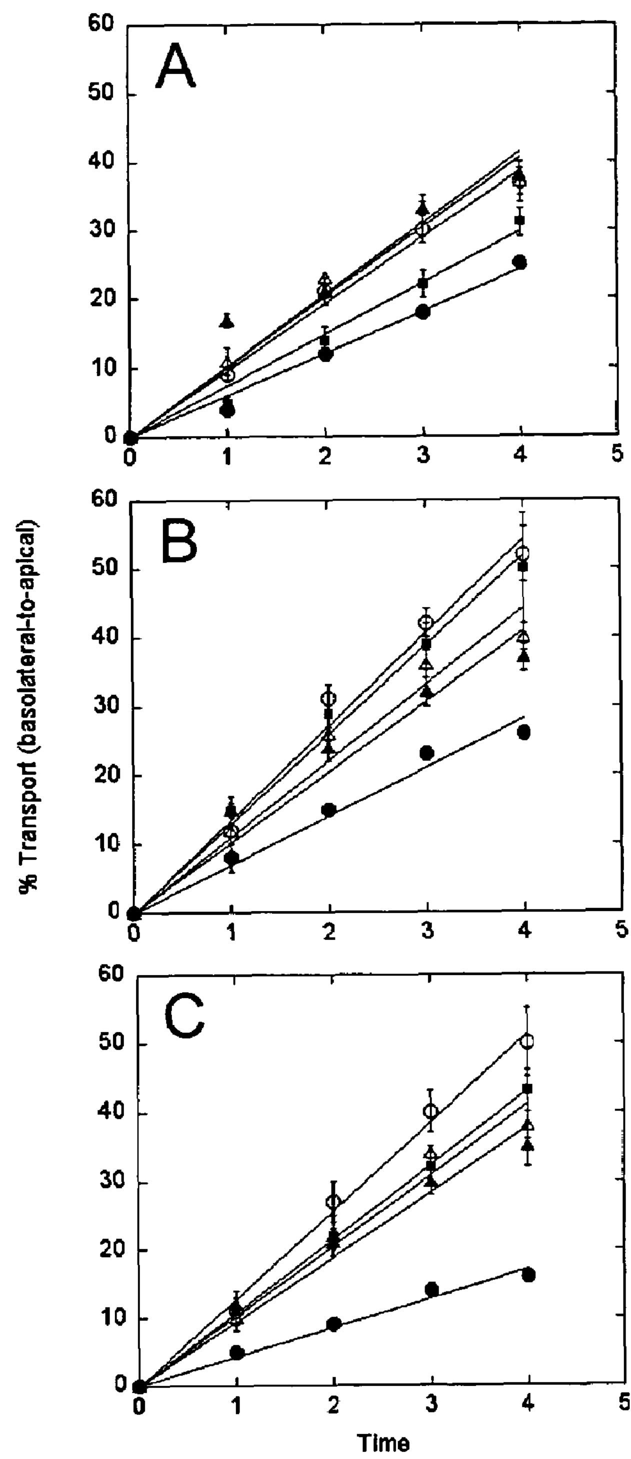

FIG. 15: Basolateral-to-apical efflux transport of HIV protease inhibitors in the presence of GF120918. Transepithelial permeability was evaluated as the percent transport of protease inhibitors across an epithelial monolayer; LLC-PK1 control cells (panel A); $MDR1_{wt}$ cells (panel B); and $MDR1_{1199}$ cells (panel C). Transport of amprenavir (▲), indinavir (●), lopinavir (Δ), ritonavir (○), and saquinavir (■).

FIG. 16: (A) Human MDR1 wild-type protein amino acid sequence (SEQ ID NO:4). (B) Human MDR1 wild-type gene nucleotide sequence (cDNA) (SEQ ID NO:5).

DETAILED DESCRIPTION OF THE INVENTION

In one aspect, the present invention relates to a collection of MDR1 transcript sequence variations (or referred to as alleles or polymorphisms, as the context may indicate). Analysis of MDR1 transcripts in leukemia patients has led to discovery of MDR1 genetic variants that influence Pgp (MDR1 protein) functions. Without intending to be bound by any particular theory, these genetic variants may alter effectiveness of drug therapies by at least two well-described mechanisms. (1) Locally, expression of Pgp at cell surface could impact the ability of drug substrates to remain in the therapeutic target cells due to a genetic variation that impact protein function, and (2) globally, expression of Pgp and variants in epithelial cells found in tissues controlling drug penetration and disposition such as gut, liver, kidney and blood-brain barrier can reduce overall drug availability in target tissues.

The MDR1 variants described can be used to identify individuals carrying MDR1 variants by standard genotyping methods to prevent adverse drug reactions and/or ineffective therapeutic effects due to drug interactions as well as altered drug dispositions. An individual having, or suspected of having, an MDR1 allele can be screened by genotyping methods to confirm or determine the presence of the MDR1 allele or polymorphism. Detection of polymorphisms in the MDR1 gene is useful in designing and performing diagnostic assays for evaluation of an individual's susceptibility to MDR1-mediated efflux, uptake, and/or transport of a drug. Such assessment is useful, for example, in the design of patient-specific treatment regimens, including selection of drug dosing and/or routes of administration.

In other aspects of the present invention, these and other genetic variants can be expressed in cell lines (e.g., stable recombinant epithelial cells) to allow systematic in vitro evaluation of drug candidates with respect to their ability to successfully penetrate the absorption barriers. In parallel, with a similar technology, continuous cell lines that express multidrug resistance associated protein-1 (MRP1) transporter protein are provided. The availability of recombinant continuous cell-lines that express functional MDR1 or MRP1 protein, and its genetic variants, permit detailed evaluation of drug candidates in cell culture to predict potential drug interactions and variations in drug efficacy. These recombinant cells expressing Pgp and/or MRP1 drug efflux transporter will accelerate pre-clinical assessment of the role of this drug efflux transporter in modulating drug levels in tissues such as brain, and in therapeutic target cells.

Detection of MDR1 Polymorphisms

The present invention includes nucleic acid molecules that are oligonucleotides capable of hybridizing, under stringent hybridization conditions, with complementary regions of a the MDR1 gene containing a polymorphism of the present invention. A nucleic acid can be DNA or RNA, and single-or double-stranded. Oligonucleotides can be naturally occurring or synthetic, but are typically prepared by synthetic means. Preferred oligonucleotides of the invention include segments of DNA, or their complements, that are polymorphic variants of the wild-type MDR1 sequence shown in SEQ ID NO:5 having any one of the polymorphic sites shown in Table 1. The segments are usually between 5 and 100 contiguous bases, and often range from 5, 10, 12, 15, 20, or 25 nucleotides to 10, 15, 30, 25, 20, 50 or 100 nucleotides. Nucleic acids between 5-10, 5- 20, 10-20, 12-30, 15-30, 10-50, 20-50, 10-100, or 20-100 bases are common. The polymorphic site can occur within any position of the segment. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. The present invention includes oligonucleotides that can be used as, for example, probes to identify nucleic acid molecules or primers to produce nucleic acid molecules. Also provided are oligonucleotides that can be used as primers to amplify DNA. Preferred oligonucleotide probes or primers include a single base change of a polymorphism of the present invention or the wild-type nucleotide that is located at the same position. Preferably the nucleotide of interest occupies a central position of a probe. Preferably the nucleotide of interest occupies a 3' position of a primer.

TABLE 1

Genetic variants that encode for human multidrug resistance (MDR1) protein

| Sequence variation[a] (Confirmed) | Amino acid variation[b] | Functional region of interest[c] | Estimated Frequency[a] | Comments |
|---|---|---|---|---|
| A→C at 163 | $Thr^{55}$→$Pro^{55}$ | Transmembrane domain (TM)1 | 0.04 | |
| A→C At 886 | $Asn^{296}$→$His^{296}$ | | 0.07 | |
| G→A at 1199 | $Ser^{400}$→$Asn^{400}$ | Cytoplasmic region in proximity to | 0.04 | G→A was described in Cascorbi et al., |

TABLE 1-continued

Genetic variants that encode for human multidrug resistance (MDR1) protein

| Sequence variation[a] (Confirmed) | Amino acid variation[b] | Functional region of interest[c] | Estimated Frequency[a] | Comments |
|---|---|---|---|---|
| | | nucleotide (NT) binding domain 1 | | Clin Pharmaco Ther 2001; 69: 169–74; |
| G→T at 1199 | $Ser^{400}$→$Ile^{400}$ | | 0.02 | |
| GT→TG at 1292-3 | $Cys^{431}$→$Leu^{431}$ | NT binding domain 1 | 0.04 | |
| T→G at 2814 | $Phe^{938}$→$Leu^{938}$ | TM 12 regions | 0.02 | |
| C→T at 3258 | $Phe^{1087}$→ $Phe^{1087}$ (no change in aa) | Hinge regions between TM 12 and NT binding domain 2 | 0.06 | |
| G→C at 3271 | $Ala^{1091}$→$Pro^{1091}$ | Hinge regions between TM 12 and NT binding domain 2 | 0.04 | |

[a]The MDR1 RNA transcripts were reverse-transcribed into complementary DNA and the entire RNA coding for MDR1 product, Pgp protein was analyzed based on wild-type data found in the Genbank data (accession # GI; 187468). Samples from a total to 44 leukemia patients were collected to date and 44 of them have been sequenced for the entire coding regions of MDR1. Estimated frequency of sequence variations in leukemia patients were estimated based on 44 subjects.
[b]Amino acid sequences were predicted based on the nucleotide sequences.
[c]Functional region of interest is predicted based on data available in NCBI database Polymorphisms are detected in a target nucleic acid from an individual being analyzed. For assay of genomic DNA, virtually any biological sample (other than pure red blood cells) is suitable. Tissue means any sample taken from any subject, preferably a human. For example, convenient tissue samples include whole blood, semen, saliva, tears, urine, fecal material, sweat, buccal epithelium, skin and hair. For assay of cDNA or mRNA, the tissue sample must be obtained from an organ in which the target nucleic acid is expressed.

In particular variations of the methods described herein, a biological sample from a subject is analyzed to determine the MDR1 genotype at one or more polymorphic sites of the MDR1 gene.

Many of the methods described below require amplification of DNA from target samples. This can be accomplished by e.g., PCR. See generally *PCR Technology: Principles and Applications for DNA Amplification* (ed. H. A. Erlich, Freeman Press, N.Y., N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert et al., *PCR Methods and Applications* 1:17 (1991); PCR (eds. McPherson et al., IRL Press, Oxford); and U.S. Pat. No. 4,683,202, each incorporated by reference herein.

Other suitable amplification methods include the ligase chain reaction (LCR) (see, e.g., Wu and Wallace, *Genomics* 4, 560 (1989), Landegren et al., *Science* 241:1077 (1988), each incorporated by reference herein), transcription amplification (see, e.g., Kwoh et al., *Proc. Natl. Acad. Sci. USA* 86:1173 (1989), incorporated by reference herein), self-sustained sequence replication (see, e.g., Guatelli et al., *Proc. Nat. Acad. Sci. USA* 87:1874 (1990), incorporated by reference herein) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The identity of bases occupying the polymorphic sites shown in Table 1 can be determined in an individual (e.g., a patient being analyzed) by several methods, which are described as follows:

Single Base Extension Methods

Single base extension methods are described by e.g., U.S. Pat. No. 5,846,710, U.S. Pat. No. 6,004,744, U.S. Pat. No. 5,888,819 and U.S. Pat. No. 5,856,092, each incorporated by reference herein. In brief, the methods work by hybridizing a primer that is complementary to a target sequence such that the 3' end of the primer is immediately adjacent to, but does not span a site of, potential variation in the target sequence. That is, the primer comprises a subsequence from the complement of a target polynucleotide terminating at the base that is immediately adjacent and 5' to the polymorphic site. The term primer refers to a single-stranded oligonucleotide capable of acting as a point of initiation of template-directed DNA synthesis under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer but typically ranges from 15 to 40 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified. Hybridization probes are capable of binding in a base-specific manner to a complementary strand of nucleic acid.

Such probes include nucleic acids and peptide nucleic acids as described in Nielsen et al., *Science* 254:1497-1500 (1991), incorporated by reference herein. A probe primer can be labeled, if desired, by incorporating a label detectable by spectroscopic, photochemical, biochemical, immunochemical, or chemical means. For example, useful labels include $^{32}P$, fluorescent dyes, electron dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support. The hybridization is performed in the presence of one or more labeled nucleotides complementary to base(s) that may occupy the site of potential variation. For example, for biallelic polymorphisms, two differentially labeled nucleotides can be used. For tetraallelic polymorphisms, four differentially-labeled nucleotides can be used. In some methods, particularly methods employing multiple differentially labeled nucleotides, the nucleotides are dideoxynucleotides. Hybridization is performed under conditions permitting primer extension if a nucleotide complementary to a base occupying the site of variation if the target sequence is present. Extension incorporates a labeled nucleotide thereby generating a labeled extended primer. If multiple differentially-labeled nucleotides are used and the target is heterozygous then multiple differentially-labeled extended primers can be obtained. Extended primers are detected providing an indication of which base(s) occupy the site of variation in the target polynucleotide.

Allele-Specific Probes

The design and use of allele-specific probes for analyzing polymorphisms is described by e.g., Saiki et al., *Nature* 324, 163-166 (1986); Dattagupta, EP 235,726; and Saiki, WO 89/11548, each incorporated by reference herein. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent such that there is a significant difference in hybridization intensity between alleles, and preferably an essentially binary response, whereby a probe hybridizes to only one of the alleles. Hybridizations are usually performed under stringent conditions that allow for specific binding between an oligonucleotide and a target DNA containing one of the polymorphic sites shown in Table 1. Stringent conditions are defined as any suitable buffer concentrations and temperatures that allow specific hybridization of the oligonucleotide to highly homologous sequences spanning at least one of the polymorphic sites shown in Table 1 and any washing conditions that remove non-specific binding of the oligonucleotide. For example, conditions of 5× SSPE (750 mM NaCl, 50 mM Na Phosphate,5 mM EDTA, pH 7.4) and a temperature of 230 C. are suitable for allele-specific probe hybridizations. The washing conditions usually range from room temperature to 60° C. Some probes are designed to hybridize to a segment of target DNA such that the polymorphic site aligns with a central position (e.g., in a 15 mer at the 7 position; in a 16 mer, at either the 8 or 9 position) of the probe. This probe design achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence. The polymorphisms can also be identified by hybridization to nucleic acid arrays, some examples of which are described by WO 95/11995, incorporated by reference herein.

Allele-Specific Amplification Methods

An allele-specific primer hybridizes to a site on target DNA overlapping a polymorphism and only primes amplification of an allelic form to which the primer exhibits perfect complementarily. See, e.g., Gibbs, *Nucleic Acid Res.* 17:2427-2448 (1989), incorporated by reference herein. This primer is used in conjunction with a second primer that hybridizes at a distal site. Amplification proceeds from the two primers leading to a detectable product signifying that the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. In some methods, the mismatch is included in the 3'-most position of the oligonucleotide aligned with the polymorphism because this position is most destabilizing to elongation from the primer. See, e.g., WO 93/22456, incorporated by reference herein. In other methods, a double-base mismatch is used in which the first mismatch is included in the 3'-most position of the oligonucleotide aligned with the polymorphism and a second mismatch is positioned at the immediately adjacent base (the pen-ultimate 3' position). This double mismatch further prevents amplification in instances in which there is no match between the 3' position of the primer and the polymorphism.

Direct-Sequencing

The direct analysis of the sequence of polymorphisms of the present invention can be accomplished using either the dideoxy-chain termination method or the Maxam Gilbert method (see Sambrook et al., *Molecular Cloning, A Laboratory Manual* (2nd ed., CSHP, New York 1989); Zyskind et al., *Recombinant DNA Laboratory Manual,* (Acad. Press, 1988), each incorporated by reference herein).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification* (W. H. Freeman and Co, New York, 1992), Chapter 7, incorporated by reference herein.

Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86:2766-2770 (1989), incorporated by reference herein. Amplified PCR products can be generated as described above, and heated or otherwise denatured, to form single stranded amplification products.

Single-stranded nucleic acids may refold or form secondary structures that are partially dependent upon the base sequence. The different electrophoretic mobilities of singlestranded amplification products can be related to base-sequence differences between alleles of target sequences.

Detection of Variant MDR1 Proteins

In certain embodiments, a biological sample that includes cellular proteins from a tissue that expresses the MDR1 gene is analyzed for the presence of a polymorphic variant of MDR1. The MDR1 protein in the sample is analyzed for the presence of one or more of the amino acid substitutions resulting from the polymorphism as set forth in Table 1. For example, the determination of the presence in a sample of the an MDR1 variant can be carried out as an immunoassay in which the sample is contacted with an antibody capable of binding the MDR1 protein. Antibodies (e.g., monoclonal antibodies) can be raised that specifically distinguish between wild-type MDR1 and an MDR1 variant as set forth in Table 1. Methods for making antibodies are well-known in the art and are described in, e.g., Harlow and Lane, *Antibodies: A Laboratory Manual* (Cold Spring Harbor Laboratory, Cold Spring Harbor, N.Y. 1988), incorporated by reference herein.

Methods of Using MDR1 Polymorphisms

After determining polymorphic form(s) present in an individual at one or more polymorphic sites, this information can be used in a number of methods.

For example, detection of MDR1 polymorphisms is useful for conducting clinical trials of drug candidates. Such trials may be performed on treated or control populations having similar or identical polymorphic profiles at a defined collection of polymorphic sites. Use of genetically matched populations eliminates or reduces variation in treatment outcome due to genetic factors, leading to a more accurate assessment of the efficacy of a potential drug.

Furthermore, the detection of MDR1 polymorphisms may be used after the completion of a clinical trial to elucidate differences in response to a given treatment. For example, the methods described herein may be used to identify subsets of patients with similar polymorphic profiles who have unusual (high or low) response to treatment or who do not respond at all (non-responders). In this way, information about the underlying genetic factors influencing response to treatment can be used in many aspects of the development of treatments (these range from the identification of new targets, through the design of new trials to product labeling and patient targeting). Additionally, the methods may be used to identify the genetic factors involved in adverse response to treatment (adverse events). For example, patients who show an adverse response may have a higher incidence of the absence of a particular MDR1 polymorphism than observed in the general population. This would allow the early identification and exclusion of such individuals from treatment. It would also provide information that might be used to understand the biological causes of adverse events and to modify the treatment to avoid such outcomes.

As with other human polymorphisms, the polymorphisms of the invention also have more general applications, such as forensic, paternity testing, linkage analysis and positional cloning.

In particular variations of the present invention, a biological sample from a subject is analyzed to determine the presence or absence of one or more MDR1 polymorphisms (e.g., as set forth in Table 1) to predict responsiveness to the drug in the subject, or to predict one or more aspects of drug disposition or penetration in vivo (e.g., absorption for oral bioavailability, blood-brain barrier penetration, or systemic clearance via secretion and elimination by kidney and liver). For example, as described further hereinbelow (see Example 2), recombinant cells expressing G1199T variant of MDR1 ($MDR1_{G1199T}$) show an increased sensitivity to drugs that are substrates of MDR1 relative to cells expressing only wild-type MDR1. Subjects having a disease or disorder which is amenable to treatment with a drug that is an MDR1 substrate and expressing the $MDR1_{G1199T}$ allele are predicted to demonstrate increased responsiveness to the drug (increased drug efficacy) relative to an individual that is homozygous for the wild-type MDR1 gene.

Accordingly, in certain variations of the present invention, a method for predicting efficacy a drug in a subject in need thereof, where the drug is a substrate of MDR1, includes (1) isolating a biological sample from the subject, the biological sample comprising nucleic acids and/or proteins; and (2) analyzing the biological sample to determine at least one of (a) the nucleotide at position 1199 of the MDR1 gene, and (b) the presence or absence of the S400I variant of MDR1 protein, where the presence of T at nucleotide position 1199 or the presence of the S400I variant is indicative of an increased efficacy of the drug in the subject relative an individual that is homozygous for a wild-type MDR1 gene. A particularly suitable technique for analysis of the MDR1 gene at position 1199 includes hybridization between a nucleic acid sample isolated from the subject and (a) a nucleic acid comprising about 10 to about 100 contiguous nucleotides of a G1199T variant of the nucleotide sequence set forth in SEQ ID NO:5, where the nucleic acid includes at least one of the nucleotide at position 1199 and a base adjacent thereto; or (b) a nucleic acid that is fully complementary to the nucleic acid of (a). In certain variations, the method further includes determining the MDR1 genotype at nucleotide position 1199 of the MDR1 gene. Drugs which are substrates of MDR1 and are amenable to prediction of drug efficacy in subjects in accordance with the above method include cytotoxic chemotherapeutic agents (e.g., doxorubicin, paclitaxol, vinblastine, and vincristine).

It has been demonstrated that the G1199A MDR1 variant ($MDR1_{G1199A}$) exhibits decreased apical to basolateral transport of HIV protease inhibitors in recombinant epithelial cells, relative to wild-type MDR1 (see Example 3). This effect would have a significant impact on, e.g., transcellular transport when the HIV protease inhibitor is exposed to the apical membrane of epithelial cells (e.g., absorption in the intestine). Determination of the presence or absence of the $MDR1_{G1199A}$ variant can therefore be used to predict the oral bioavailability of HIV protease inhibitors in a subject, and/or penetration of an HIV protease inhibitor into cells and tissues of the lymphoid and central nervous systems of a subject, relative to an individual that is homozygous for the wild-type MDR1 gene.

Accordingly, in yet other variations of the present invention, a method for predicting oral bioavailability and or blood-brain barrier penetration of an HIV protease inhibitor in a subject in need thereof is provided that includes (1) isolating a biological sample from the subject, the biological sample comprising nucleic acids and/or proteins; and (2) analyzing the biological sample to determine at least one of (a) the nucleotide at position 1199 of the MDR1 gene, and (b) the presence or absence of the S400N variant of MDR1 protein; where the presence of A at nucleotide position 1199 or the presence of the S400N variant is indicative of a decreased oral bioavailability or blood-brain barrier penetration of the HIV protease inhibitor in the subject relative an individual that is homozygous for a wild-type MDR1 gene. As indicated above, a particularly suitable technique for analysis of the MDR1 gene at position 1199 includes hybridization between a nucleic acid sample isolated from the subject and (a) a nucleic acid comprising about 10 to about 100 contiguous nucleotides of a G1199A variant of the nucleotide sequence set forth in SEQ ID NO:5, where the nucleic acid includes at least one of the nucleotide at position 1199 and a base adjacent thereto; or (b) a nucleic acid that is fully complementary to the nucleic acid of (a). In certain variations, the method further includes determining the MDR1 genotype at nucleotide position 1199 of the MDR1 gene. HIV protease inhibitors particularly amenable to prediction of oral bioavailability in subjects in accordance with the above method include, for example, amprenavir, indinavir, lopinavir, ritonavir, and saquinavir.

The above methods for predicting responsiveness to a drug or oral bioavailability of an HIV protease inhibitor can further include designing a patient-specific treatment regimen based on the information obtained from using the method. In certain embodiments, a mode of administration for the HIV protease inhibitor can be selected based the information obtained. For example, where a decreased oral bioavailability is indicated for the subject, a clinician may choose, for example, intravenous administration of the HIV protease inhibitor to deliver the drug directly into the bloodstream. Also, a clinician can select an HIV protease inhibitor that is not a substrate for the MDR1. Similarly, where a decreased drug responsiveness is indicated by presence of the $MDR1_{G1199T}$ allele, dosage of the drug can be increased, or a different drug that is not an MDR1 substrate selected for administration.

It has also been demonstrated that cells expressing the G1199A MDR1 polymorphic variant exhibit increased resistance to vinblastine and vincristine relative to cells expressing wild-type MDR1. Accordingly, in other embodiments, a method for predicting the efficacy of vinblastine or vincristine in a subject in need thereof is provided that includes (1) isolating a biological sample from the subject, the biological sample comprising nucleic acids and/or proteins; and (2) analyzing the biological sample to determine at least one of (a) the nucleotide at position 1199 of the MDR1 gene, and (b) the presence or absence of the S400N variant of MDR1 protein; where the presence of A at nucleotide position 1199 or the presence of the S400N variant is indicative of a decreased efficacy of vinblastine or vincristine in the subject relative an individual that is homozygous for a wild-type MDR1 gene. Again, a particularly suitable technique for analysis of the MDR1 gene at position 1199 includes hybridization between a nucleic acid sample isolated from the subject and (a) a nucleic acid comprising about 10 to about 100 contiguous nucleotides of a G1199A variant of the nucleotide sequence set forth in SEQ ID NO:5, where the nucleic acid includes at least one of the nucleotide at position 1199 and a base adjacent thereto; or (b) a nucleic acid that is fully complementary to the nucleic acid of (a). In certain variations, the method further includes determining the MDR1 genotype at nucleotide position 1199 of the MDR1 gene. In still further embodiments, the method further comprises selecting a cytotoxic chemotherapeutic drug for administration to the subject, or determining an appropriate dosage of a chemotherapeutic agent, based on the presence or absence the G1199A MDR1 polymorphism or S400N MDR1 variant (e.g., if the G1199A polymorphism is present, a chemotherapeutic agent which is not vinblastine or vincristine; or selecting an increased dosage of vinblastine or vincristine relative to a subject that does not express the G1199A MDR1 variant).

MDR1 Nucleic Acids, Polypeptides, Recombinant Cells, and Methods of Use

In another aspect, nucleic acids encoding a variant of the MDR1 protein of SEQ ID NO:5, or a fragment thereof, are also provided. In certain embodiments, the MDR1 nucleic acids comprise at least 15, typically at least 17, at least 20, or at least 25, and more typically at least 30, at least 50, or at least 100 or more nucleotides of a variant of the nucleotide sequence set forth in SEQ ID NO:5, where the variant MDR1 nucleic acid includes the nucleotide at least one of the following nucleotide positions: 163, 886, 1199, 1292, 1293, 2814, 3258, and 3271; and where the variant nucleic acid contains a sequence variation (i.e., variant from wild-type) at least one of the foregoing positions. In particular embodiments, the variant MDR1 nucleic acid includes at least one of the following sequence variations: A163C, A886C, G1199T, G1292T, T1293G, T2814G, C3258T, and G3271C. Typically, an MDR1 variant having either the G1292T or T1293G nucleotide substitution will have these substitutions at both positions (herein also referred to as GT1292-3TG or 1292-3TG). Further, in some embodiments in which the MDR1 variant includes a sequence variation at any one or more of positions 163, 886, 1292, 1293, 2814, 3258, and 3271, the variant further includes the GI 199A polymorphism.

In some embodiments, the MDR1 variant includes either only one sequence variation at nucleotide position 163, 886, 1199, 2814, 3258, or 3271; or a sequence variation at positions 1292-93 (e.g., the particular sequence variations set forth in Table 1); in yet other embodiments, the MDR1 variant comprises two, three, or more of the foregoing sequence variations. An MDR1 variant of the present invention optionally includes one or more additional sequence variations corresponding to other identified MDR1 polymorphisms (e.g., the particular sequence variations listed in Table 2).

The variant MDR1 nucleic acid can, for example, encode a full-length variant MDR1 protein, or a functional fragment thereof. In yet other embodiments, the MDR1 nucleic acid is a probe or a primer such as, e.g., described above for use in detection of an MDR1 polymorphism in a biological sample.

MDR1 nucleic acids of the present invention further include derivatives encoding other possible codon choices for the same amino acid, or encoding conservative amino acid substitutions thereof. Due to the degeneracy of nucleotide coding sequences, other DNA sequences which encode substantially the same amino acid sequence as a variant MDR1 nucleic acid can be used in the practice of the present invention. These include, but are not limited to, nucleotide sequences comprising all or portions of a variant MDR1 nucleic acid which is altered by the substitution of different codons that encode the same or a functionally equivalent amino acid residue (e.g., a conservative substitution) within the sequence, thus producing a silent change.

MDR1 nucleic acids of the present invention further include those nucleic acids specifically hybridizable or complementary to the foregoing sequences. Hybridizable nucleic acids can comprise sequences complementary to at least 10, 15, 17, 20, 25, 50, 100, 200, or 250 nucleotides or more of a MDR1 gene, including full-length complements of an MDR1 nucleic acid. Nucleic acids are specifically hybridizable to an MDR1 nucleic acid, or to a nucleic acid encoding a MDR1 derivative, under stringent conditions. Stringent conditions are well-known to those of skill in the art and vary predictably depending on conditions such as salt concentrations, temperature, and the base composition of the particular nucleic acid sequence. (See generally Sambrook and Russell, *Molecular Cloning, A Laboratory Manual* (3rd ed. 2001); Ausubel et al. (eds.), *Current Protocols in Molecular Biology* (1994); Sambrook et al., *Molecular Cloning, A Laboratory Manual* (2nd ed. 1989), each incorporated by reference herein.)

Various recombinant DNA methods known in the art can be used to prepare the MDR1 nucleic acids described hereinabove. For example, expression cloning, genomic cloning, and PCR (see, e.g., Russell et al., supra; Sambrook et al., supra; Ausubel et al., supra.) can be used to obtain MDR1 polynucleotides which can be used for further manipulation. Nucleic acid sequences can also be produced by synthesis using standard methods (e.g., by use of a commercially available automated DNA synthesizer) (typically for shorter nucleic acids). Nucleic acids can be further manipulated as desired using routine techniques. (See generally, e.g., Russell et al., supra; Sambrook et al., supra; Ausubel et al., supra.) For example, known MDR1 sequences can be modified to prepare sequences encoding MDR1 variants polypeptides of the present invention using, e.g., standard in vitro site-directed mutagenesis (see, e.g., Hutchison et al., *J. Biol. Chem.* 253: 6551-60 (1978), incorporated by reference herein), the use of TAB® linkers (Pharmacia), PCR mutagenesis methods, and the like.

The MDR1-encoding nucleic acids can be inserted into an appropriate expression vector (i.e., a vector which contains the necessary elements for the transcription and translation of the inserted polypeptide-coding sequence). A variety of host-vector systems can be utilized to express an MDR1 polypeptide-coding sequence. These include, for example, mammalian cell systems transfected with plasmid vectors or infected with virus (e.g., vaccinia virus, adenovirus, parvoviruses (e.g. AAV), sindbis virus, Venezuelan equine encephalitis (VEE) virus, and the like), insect cell systems infected with virus (e.g., baculovirus), microorganisms such as yeast containing yeast vectors, or bacteria transformed with bacteriophage DNA, plasmid DNA, or cosmid DNA. The expression elements of vectors vary in their strengths and specificities. Depending on the host-vector system utilized, any one of a number of suitable transcription and translation elements can be used. In specific embodiments, the MDR1 polypeptide is expressed in human cells, rat cells, other mammalian cells, yeast or bacteria.

Any suitable method can be used for insertion of MDR1 nucleic acids into an expression vector. Suitable expression vectors typically include appropriate transcriptional and translational control signals. Suitable methods include in vitro recombinant DNA and synthetic techniques and in vivo recombination techniques (genetic recombination). Expression of nucleic acid sequences can be regulated by a second nucleic acid sequence so that the encoded nucleic acid is expressed in a host transformed with the recombinant DNA molecule. For example, expression of an MDR1 polypeptide can be controlled by any suitable promoter/enhancer element known in the art. Suitable promoters include, for example, the SV40 early promoter region (Benoist and Chambon, *Nature* 290:304-10 (1981)), the promoter contained in the 3' long terminal repeat of *Rous sarcoma* virus (Yamamoto et al., *Cell* 22:787-97 (1980)), the herpes thymidine kinase promoter (Wagner et al., *Proc. Natl. Acad. Sci. USA* 78:1441-45 (1981)), the cytomegalovirus promoter, the translational elongation factor EF-1 promoter, the regulatory sequences of the metallothionein gene (Brinster et al., *Nature* 296:39-42 (1982)), prokaryotic promoters such as, for example, the lactamase promoter (Villa-Komaroff et al., *Proc. Natl. Acad. Sci. USA* 75:3727-31 (1978)) or the tac promoter (deBoer et al., *Proc. Natl. Acad. Sci. USA* 80:21-25 (1983)), plant expression vectors including the cauliflower mosaic virus 35S RNA promoter (Gardner et al., *Nucl. Acids Res.* 9:2871-88 (1981)), and the promoter of the photosynthetic enzyme ribulose biphosphate carboxylase (Herrera-Estrella et al., *Nature* 310: 115-20 (1984)), promoter elements from yeast or other fungi such as the GAL7 and GAL4 promoters, the ADH (alcohol dehydrogenase) promoter, the PGK (phosphoglycerol kinase) promoter, the alkaline phosphatase promoter, and the like.

Other mammalian promoters include, for example, the following animal transcriptional control regions, which exhibit tissue specificity: the elastase I gene control region which is active in pancreatic acinar cells (Swift et al., *Cell* 38:639-46 (1984); Omitz et al., *Cold Spring Harbor Symp. Quant. Biol.* 50:399-409 (1986); MacDonald, *Hepatology* 7(1 Suppl.): 42S-51S (1987); the insulin gene control region which is active in pancreatic beta cells (Hanahan, *Nature* 315:115-22 (1985)), the immunoglobulin gene control region which is active in lymphoid cells (Grosschedl et al., *Cell* 38:647-58 (1984); Adams et al., *Nature* 318:533-38 (1985); Alexander et al., *Mol. Cell. Biol.* 7:1436-44 (1987)), the mouse mammary tumor virus control region which is active in testicular, breast, lymphoid and mast cells (Leder et al., *Cell* 45:485-95 (1986)), the albumin gene control region which is active in liver (Pinkert et al., *Genes Dev.* 1:268-76 (1987)), the alpha-fetoprotein gene control region which is active in liver (Krumlauf et al., *Mol. Cell. Biol.* 5:1639-48 (1985); Hammer et al., *Science* 235:53-58 (1987); the alpha 1-antitrypsin gene control region which is active in the liver (Kelsey et al., *Genes and Devel.* 1:161-71 (1987)); the beta-globin gene control region which is active in myeloid cells (Magram et al., *Nature* 315:338-40 (1985); Kollias et al., *Cell* 46:89-94 (1986); the myelin basic protein gene control region which is active in oligodendrocyte cells in the brain (Readhead et al., *Cell* 48:703-12 (1987)); the myosin light chain-2 gene control region which is active in skeletal muscle (Shani, *Nature* 314:283-86 (1985)); and the gonadotropic releasing hormone gene control region which is active in the hypothalamus (Mason et al., *Science* 234:1372-78 (1986)).

In certain embodiments, a vector is used that comprises, in operative combination, a transcription promoter, the MDR1-encoding nucleic acid, a transcription terminator, and one or more origins of replication. In other embodiments, the vector includes one or more selectable markers (e.g., an antibiotic resistance gene). Suitable selectable markers include, for example, those conferring resistance to ampicillin, tetracycline, neomycin, G418, and the like.

Once a suitable expression vector host system and growth conditions are established, methods that are known in the art can be used to propagate it. In addition, host cells can be chosen that modulate the expression of the inserted nucleic acid sequences, or that modify or process the gene product in the specific fashion desired. Expression from certain promoters can be elevated in the presence of certain inducers; thus, expression of the MDR1 sequence can be controlled. Furthermore, different host cells having characteristic and specific mechanisms for the translational and post-translational processing and modification (e.g., glycosylation or phosphorylation) of polypeptides can be used. Appropriate cell lines or host systems can be chosen to ensure the desired modification and processing of the expressed polypeptide. For example, expression in a bacterial system can be used to produce an unglycosylated polypeptide.

The invention further relates to the MDR1 polypeptides encoded by the foregoing MDR1 nucleic acids, including derivatives and analogs. The production and use of MDR1 polypeptides, and derivatives and analogs thereof, are also within the scope of the present invention. MDR1 variant proteins are useful, for example, in studies relating to elucidation of molecular mechanisms of MDR1 function, including, e.g., mechanisms leading to reduction of drug resistance. Such studies can be conducted, for example, using purified and crystallized proteins alone or complexed with particular MDR1 substrates.

Accordingly, in one aspect, the present invention provides an isolated MDR1 protein which is a variant of the wild-type MDR1 protein having the amino acid sequence set forth in SEQ ID NO:4 and having at least one of the following amino acid substitutions: T55P, N296H, S400I, C431L, F938L, and A1091P. In certain variations, the MDR1 protein includes only one amino acid substitution selected from T55P, N296H, S400I, C431L, F938L, and A1091P; in other embodiments, the MDR1 protein includes two or more of the foregoing substitutions. The variant MDR1 proteins of the present invention can optionally include one or more amino acid substitutions corresponding to other known MDR1 polymorphic variants, such as, for example, those set forth in Table 2.

Derivatives of variant MDR1 polypeptides include those altered by substitution, addition, or deletion of one or more amino acid residues that provide for functionally active molecules. MDR1 polypeptide derivatives include, e.g., those containing as a primary amino acid sequence all or part of the amino acid sequence of an MDR1 polypeptide including altered sequences in which one or more functionally equivalent amino acid residues (e.g., a conservative substitution) are substituted for residues within the sequence. In certain embodiments, the MDR1 poly eptide derivative is a functional fragments of a full-length MDR1 variant as described herein having one or more biological activities associated with full-length MDR1 protein.

In a specific embodiment, the MDR1 derivative is a chimeric, or fusion, protein comprising a variant MDR1 polypeptide joined at its amino- or carboxy-terminus via a peptide bond to an amino acid sequence of a different protein. In one embodiment, such a chimeric protein is produced by recombinant expression of a nucleic acid encoding the protein. The chimeric product can be made by ligating the appropriate nucleic acid sequence, encoding the desired amino acid sequences, to each other in the proper coding frame and expressing the chimeric product by methods commonly known in the art. Alternatively, the chimeric product can be made by protein synthetic techniques (e.g., by use of an automated peptide synthesizer).

MDR1 polypeptides can be produced by recombinant DNA techniques, by chemical synthetic methods, or by purification of native polypeptides. MDR1 polypeptides can be isolated and purified by standard methods including chromatography (e.g., ion exchange, affinity, sizing column chromatography, high pressure liquid chromatography), centrifugation, differential solubility, or by any other standard technique for the purification of proteins.

Functional properties of variant MDR1 polypeptides may be evaluated, for example, in vitro in a recombinant cell line expressing the MDR1 variant. Cell lines expressing recombinantly produced MDR1 variants as described herein are also within the scope of the present invention. In typical embodiments, the expression system utilizes a cell type which is amenable to evaluation of transcellular permeability such as, e.g., a polarized epithelial cell line (e.g., LLC-PK1, MDCKII, or Caco-2). In a preferred embodiment, the cell line is stably transformed with a non-viral expression vector (e.g., a pCR3.1 TA vector (Invitrogen, Carlsbad, Calif.) containing cytomegalovirus (CMV) and T7 promoters capable of transcription). A particularly suitable recombinant expression system for expression of functional MDR1 protein is further described hereinbelow (see Examples). In specific embodiments, the recombinant cell line is a recombinant LLC-PK1 cell line expressing MDR1 protein and its variants as set forth in Table 3, infra. Functional properties of MDR1 that can be evaluated using recombinant MDR1-expressing cells include, for example, efflux, uptake, and transcellular transport of agents, including, e.g., pharmaceutical agents.

The recombinant cell lines of the present invention are useful in methods for determining the impact of a MDR1 polymorphism on drug penetration and/or disposition. MDR1-mediated efflux, uptake, or transcellular transport. For example, in certain embodiments, a method is provided for evaluating the influence of a MDR1 polymorphism, or a particular MDR1 haplotype comprising two or more MDR1 polymorphisms, on MDR1-mediated efflux, uptake, or transcellular transport. The method includes (1) contacting a first cell with a therapeutic agent, where the first cell expresses an MDR1 variant having at least one of the following amino acid substitutions: T55P, N296H, S400I, C431L, F938L, and A1091P; (2) contacting a control cell with the therapeutic agent, where the control cell expresses a wild-type MDR1 protein; (3) culturing the first cell and the control cell; (4) determining for each of the first cell and control cell the uptake, efflux, and/or transcellular transport of the therapeutic agent; and (4) comparing the level of uptake, efflux, or transcellular transport of the therapeutic agent in the first cell with that of the control cell. Assays for measuring the uptake, efflux, and/or transcellular transport of an agent in a cell are well-known in the art; exemplary assays are described further infra (see Examples).

In certain variations of the above method for evaluating the influence of one or more MDR1 polymorphisms, the MDR1 protein variant expressed by the first recombinant cell includes only one amino acid substitution selected from T55P, N296H, S400I, C431L, F938L, and A1091P; in other embodiments, the MDR1 protein includes two or more of the foregoing substitutions. The variant MDR1 protein expressed by the first recombinant cell can optionally include one or more amino acid substitutions corresponding to other known MDR1 polymorphic variants, such as, for example, those set forth in Table 2.

Compositions Relating to Rat MRP1

The present invention also provides compositions relating to the rat MRP1 cDNA and protein, polymorphisms within that gene and methods relating to the use of the rat MRP1 for the expression of rat MRP1, and for clinically applicable strategies to identify and adjust the management of medications in patients with exceptional genetic traits, disease conditions, or risk of drug-drug interactions, based on the presence of certain MRP1 polymorphisms. In one aspect, the sequence of the rat MRP1 cDNA is provided. In a related aspect, the sequence of the rat MRP1 protein and nucleic acid sequences encoding that protein are provided.

The rat MRP1 cDNA has been closed and sequenced. (See FIG. 1.) The rat MRP1 sequence exhibits 94.3% and 83.0% nucleotide sequence homology to that of mice and human, respectively (See FIG. 1). The isolated rat MRP1 cDNA, or nucleic acids encoding the rat MRP1 protein or a functional fragment thereof, are also provided.

In certain embodiments, a isolated rat MRP1 nucleic acid is at least 90%, at least 95%, or at least 99% identical to the rat MRP1 sequence of FIG. 1. The terms "identical" or "percent identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region, as measured using one of the following sequence comparison algorithms or by manual alignment and visual inspection. Such sequences are then said to be "substantially identical." This definition also refers to the complement of a test sequence. Optionally, the identity exists over a region that is at least about 30 amino acids or nucleotides in length, typically over a region that is 50, 75 or 150 amino acids or nucleotides. In one embodiment, the sequences are substantially identical over the entire length of the coding regions.

The terms "similarity," or "percent similarity," in the context of two or more polypeptide sequences, refer to two or more sequences or subsequences that have a specified percentage of amino acid residues that are either the same or similar as defined in the conservative amino acid substitutions defined above (i.e., at least 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 25 amino acids in length, or more preferably over a region that is at least about 50, 75 or 100 amino acids in length.

For sequence comparison, typically one sequence acts as a reference sequence to which test sequences are compared. When using a sequence comparison algorithm, test and reference sequences are typically input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (*Adv. Appl. Math.* 2:482 (1981)), by the homology alignment algorithm of Needleman and Wunsch (*J. Mol. Biol.* 48:443 (1970)), by the search for identity method of Pearson and Lipman (*Proc. Natl. Acad. Sci. USA* 85:2444 (1988)), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see, generally Ausubel et al., *Current Protocols in Molecular Biology,* John Wiley and Sons, New York (1996)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351-60 (1987)). The method used is similar to the CLUSTAL method described by Higgins and Sharp (*Gene* 73:237-44 (1988); *CABIOS* 5:151-53 (1989)). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al. (*J. Mol. Biol.* 215:403-10 (1990)). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin and Altschul, *Proc. Natl. Acad. Sci. USA* 90:5873-87 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is typically between about 0.35 and about 0.1. Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments, such as Southern and northern hybridizations, are sequence-dependent, and are different under different environmental parameters. Longer sequences hybridize specifically at higher temperatures. An extensive guide to the hybridization of nucleic acids is found in Tijssen, *Laboratory Techniques in Biochemistry and Molecular Biol-*

*ogy—Hybridization with Nucleic Acid Probes,* part I, chapter 2 "Overview of principles of hybridization and the strategy of nucleic acid probe assays," Elsevier, N.Y. (1993). Generally, highly stringent hybridization and wash conditions are selected to be about 5° C. lower than the thermal melting point (Tm) for the specific sequence at a defined ionic strength and pH. Typically, under "stringent conditions," a probe will hybridize to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on a filter in a Southern or northern blot is 50% formamide in 4-6× SSC or SSPE at 42° C., or 65-68° C. in aqueous solution containing 4-6 SSC or SSPE. An example of highly stringent wash conditions is 0.15 M NaCl at 72° C. for about 15 minutes. An example of stringent wash conditions is a 0.2× SSC wash at 65° C. for 15 minutes. (See generally Sambrook et al., *Molecular Cloning, A Laboratory Manual,* 2nd ed., Cold Spring Harbor Publish., Cold Spring Harbor, N.Y. (1989)). Often, a high stringency wash is preceded by a low stringency wash to remove background probe signal.

In another aspect, the rat MRP1 cDNA or nucleic acid is used to develop a cell line expressing recombinant rMRP1. A rat MRP1-expressing cell line is typically a stable cell line or a stable epithelial cell line. Cell lines expressing recombinant rMRP1 protein can be used for trans-epithelial transport studies of drugs, prodrugs and other substances. With a parallel human MRP1 continuous cell line developed, the role of rMPR1 and human MRP1 in mediating resistance to and modifying the drug disposition profile of commonly prescribed anti-tumor drugs can be elucidated.

Cell Lines Expressing MRP1 or MDR1 and Related Methods

In yet another aspect of the present invention, a mammalian MPR1 or MDR1 nucleic acid is used to develop a cell line expressing a recombinant MRP1 or MDR1 protein. The MRP1 or MDR1 nucleic acid can be rat, human, or other mammal. Methods for expression of a recombinant protein in host cells generally known in the art. Exemplary methods that may be used for expression of recombinant MRP1 or MDR1 are described supra with respect to MDR1 protein variants. Particularly suitable cell lines are those which are capable of transcellular transport, typically, for example, a polarized cell line or cell line capable of differentiation to a polarized phenotype (e.g., an epithelial cell line). In a preferred embodiment, the cell line stably expresses the recombinant protein. In exemplary embodiments, the cell line is a stable epithelial cell line such as, for example, an intestinal or renal epithelial cell line (e.g., LLC-PK1, MDCKII, or Caco-2). As used herein, a "stable" cell line contains and expresses the recombinant nucleic over many generations. In typical variations, a non-viral vector comprising the MRP1 or MDR1 nucleic acid is used to develop the MRP1 or MDR1-expressing cell line. In one exemplary embodiment, the non-viral vector is a pCR3.1 TA vector (Invitrogen, Carlsbad, Calif.) containing cytomegalovirus (CMV) and T7 promoters capable of transcription (see, e.g., Yang et al., *Biotechniques* 33:196, 8, 200 passim. (2002)). The use of a non-viral vector facilitates long-term expression of the MRP1 or MDR1 recombinant protein without the co-expression of viral elements, which may influence MRP1 or MDR1 function and may therefore, for example, influence the ability to detect functional variability due to MRP1 or MDR1 polymorphisms.

The MRP1- and MDR1-expressing cell lines of the present invention are useful, for example, for evaluating the influence of an MRP1 or MDR1 protein to the disposition of an agent in cells, and/or penetration of an agent across absorption barriers. For example, in certain embodiments, a method for evaluating the contribution of an MRP1 or MDR1 protein to the disposition or penetration of an agent is provided that includes contacting the cell line expressing the MRP1 or MDR1 protein with the agent; culturing the contacted cell line; and determining at least one of the uptake, efflux, or transcellular transport of the agent. The study of disposition or penetration of agents in vitro using the cell lines and methods described herein is useful for predicting pharmacokinetics in vivo. The screening of candidate therapeutic agents using the cell lines and methods of the present invention can facilitate the development of drugs that can, for example, efficiently penetrate absorption barriers (e.g., intestine and blood-brain barrier) as well as efficiently accumulate in target cells and tissues.

For example, a cell line expressing a recombinant mammalian MRP1 or MDR1 protein can be used to determine a drug disposition profile of commonly prescribed anti-tumor drugs. In particular, a cell line expressing a recombinant mammalian MRP1 or MDR1 protein can be contacted with a therapeutic agent to determine the susceptibility, toxicity, $LD_{50}$, or the like of the therapeutic agent on the cell line. The cell line can express one or more MRP1 and/or MDR1 or other related (i.e., a homolog or ortholog) transporter proteins.

In particular embodiments, the cell lines of the present invention are used to determine the influence of a MDR1 or MRP1 polymorphism, or a particular MDR1 or MRP1 haplotype having a combination of two or more polymorphisms, on MDR1- or MRP1-mediated efflux, uptake, or transcellular transport. In certain embodiments, the method includes (1) contacting a first cell expressing a recombinant MRP1 or MDR1 protein with a therapeutic agent, where the recombinant MRP1 or MDR1 protein expressed in the first cell is an allelic variant of a wild-type MRP1 or MDR1 protein; (2) contacting a control cell with the therapeutic agent, where said control cell expresses the wild type MRP1 or MDR1 protein corresponding to the allelic variant; (3) culturing the first cell and control cell; (4) determining for each of the first cell and control cell at least one of the uptake, efflux, or transcellular transport of the therapeutic agent; and (5) comparing the level of uptake, efflux, or transcellular transport of the therapeutic agent in the first cell with that of the control cell. Cell lines which are particularly suitable for use in the above method include, for example, the recombinant MDR1-expressing cell lines set forth in Table 3, infra.

In exemplary embodiments of the present invention, DNA plasmid vectors capable of expressing MRP1 transcripts in vitro have been constructed. The same set of vectors are designed to allow generation of stable recombinant mammalian cells. Suitable host cells include, for example, LLC-PK1 (a porcine epithelial cells that form tight junctions), MDCK (Madin-Darby canine kidney epithelial cells that form tight junctions), and K562 (human leukemia cell). These stable recombinant cells can be stored in liquid $N_2$ freezers and passaged in culture. A list of these recombinant cell lines expressing genetic variants of Pgp, including wild-type control (Table 2) are listed in Table 3.

TABLE 2

A partial list of MDR1 genetic variants that have been linked, or proposed to modulate Pgp function in vitro or in vivo.

| Nucleotide Position | Location | Effect | Allelic Frequency (%)† | Reference |
|---|---|---|---|---|
| G→A at 1199 | exon 11 | Ser→Asn at 400 | 5.5 | {Cascorbi, 2001 #5; Hoffmeyer, 2000 #6; Kim, 2001 #8} |
| C→ T at 1236 | exon 12 | wobble | 41.0 | {Kioka, 1989 #95; Cascorbi, 2001 #5; Hoffmeyer, 2000 #6; Kim, 2001 #8} |
| G→T at 2677 | exon 21 | Ala→Ser At 893 | 41.6 | {Mickley, 1998 #33; Kioka, 1989 #95; Cascorbi, 2001 #5; Kim, 2001 #8} |
| G→A at 2677 | exon 21 | Ala→Thr At 893 | 1.9 | {Mickley, 1998 #33; Kioka, 1989 #95; Cascorbi, 2001 #5; Kim, 2001 #8} |
| C→T at 3435 | exon 26 | Wobble (proposed to be linked to 1236 and 2677 in producing functional effects) | 53.9 | {Kioka, 1989 #95; Cascorbi, 2001 #5; Hoffmeyer, 2000 #6; Kim, 2001 #8} |

†Allelic frequencies are reported as the frequency of the polymorphism in a Caucasian population.

TABLE 3

A list of novel, stable recombinant-epithelial cell lines expressing Pgp and genetic variants.

| Recombinant LLC-PK1 cell expressing MDR1 protein and it variants | Unique MDR1 coding sequence of Pgp protein expressed: Nucleotide (validated) | Amino acid | Comments |
|---|---|---|---|
| Wild type | None | None | Stable cell lines with MDR1 sequence and function validated |
| MDR1$_{1199A}$ | C→A at 1199 | Ser→Asn at 400 | Reduced substrate transport activity; altered cancer drug resistance |
| MDR1$_{1199T}$ | C→T at 1199 | Ser→Ile at 400 | Altered efflux transport activity of MDR1 and drug resistance |
| MDR1$_{163C}$ | A→C at 163 | Thr→Pro at 55 | |
| MDR1$_{1292-3TG}$ | GT→TG at 1292-3 | Cys→Leu at 431 | |
| MDR1$_{2814G}$ | T→G at 2914 | Phe→Leu at 938 | |
| MDR1$_{3271C}$ | G→C at 3271 | Ala→Pro at 1091 | |
| MDR1$_{2677T}$ | G→T at 2677 | Ala→Ser at 893 | |
| MDR1$_{2677A}$ | G→A at 2677 | Ala→Thr at 893 | |
| MDR1$_{1236T}$ | C→T at 1236 | No aa change at 312 | |
| MDR1$_{3435T}$ | C→T at 3435 | No aa change at 1145 | |
| MDR1$_{1236T/2677T}$ (double variant) | C→T at 1236<br>G→T at 2677 | No aa change at 312<br>Ala→Ser at 893 | |
| MDR1$_{1236T/2677T/3435T}$ (triple variant) | C→T at 1236<br>G→T at 2677<br>C→T at 3435 | No aa change at 312<br>Ala→Ser at 893<br>No aa change at 1145 | |
| MDR1$_{2677T/3435T}$ (double variant) | G→T at 2677<br>C→T at 3435 | Ala→Ser at 893<br>No aa change at 1145 | |
| MDR1$_{3258T}$ | C→T at 3258 | No aa change at 1087 | |

In an exemplary embodiment, to demonstrate utility of recombinant epithelial expressing MDR1 or MRP1, a cell-line that express genetic variant, GI 199A (Tables 1-2) of MDR1 has been constructed. The examples (infra) describe the methods for isolating such a cell line and exemplary data that validated the function of stable recombinant cells and utility in evaluation of drug resistance, as well as in effects of genetic variations in drug transport with LLC-PK1 cell expressing G1199A MDR1 variant (referred to as $MDR1_{1199}$). The efflux transport of Rhodamine-123 in $MDR1_{1199}$ cells was approximately 4.5-fold lower than efflux in $MDR1_{wt}$ (wild-type control) cells. Cytotoxicity studies have shown that MDR1wt and $MDR1_{1199}$ cells exhibited similar resistance to doxorubicin; however, $MDR1_{1199}$ cells were more resistant to vinblastine and vincristine. The apparent transepithelial permeability ratios of R123 in $MDR1_{wt}$ and $MDR1_{1199}$ cells were 3.54±0.94 and 2.02±0.51 ($p<0.05$), respectively. Therefore, the G1199A polymorphism alters the efflux and transepithelial permeability of a fluorescent substrate and sensitivity to select cytotoxic agents, which may influence drug disposition and therapeutic efficacy of some P-glycoprotein substrates.

Employing a similar technology, continuous MRP1 cell lines have been constructed. These recombinant cells were derived from MDCK-II epithelial cells that form tight junctions, suitable for transepithelial transport assessment. Several stable clones of epithelial cells that consistently express rMRP1 were constructed, which could be differentiated to form a polarized monolayer for transepithelial flux studies. These cells were shown express full-length transcript. The cells that consistently over-expressed rMRP1 were expanded from a single cell clone and analyzed for MRP1 function. These MRP1-expressed cells exhibited consistent efflux transport of an MRP1 fluorescence substrate calcein, as evident by 5.2- to 8.7-fold higher efflux activity over 17 weeks in culture. In addition, the efflux transport activity is specifically mediated by MRP1, because addition of MRP1 inhibitors, indomethacin (100 μM) or MK571 (10 μM, an MRP1-specific inhibitor), suppressed efflux transport of calcein back to the control level (See manuscript 1).

Employing the recombinant cells expressing rat or human MRP1, it was demonstrated that rMRP1 has a similar substrate selectivity compared to human MRP1, and could confer drug resistance to cells. The differentiated recombinant rMRP1-MDCK cells exhibit directional transepithelial transport of vinblastine. These stable recombinant cells can be used to evaluate drug candidates that are either MRP1 substrates or inhibitors, as well as further elucidate MRP1 structure and function.

In further embodiments, recombinant cell line are provided based on: (1) other types of epithelial cells to provide closer prediction of tissue barriers controlling the drug penetration, availability and elimination, (2) expression vectors containing more than one genetic variation (allele or polymorphism) of transporter proteins, including the two described herein (MDR1 and MRP1), (3) continuous cell lines expressing multiple transport proteins to estimate the combination effects, and (4) modifications of plasmid sequences to enhance expression, localization and function.

Based on the sequence variations described herein, therapeutic strategies such as single chain inhibitory RNA or DNA sequences, antisense RNA or DNA sequences, and sequence specific ribozymes designed to interfere with drug resistance and transport function of MDR1 and MRP1 can be constructed. Also, these sequences can be used to identify individuals carrying these traits to manage therapeutic efficacy and potential toxicity due to altered drug delivery and disposition. The plasmid vectors, containing for example the polymorphisms described in Tables 1-3, can also be used to produce RNA standards to estimate the number of RNA transcripts in tumor cells or other surrogate cells. The availability of RNA standards allows a quantitative estimate of transcript copy number, instead of the highly variable semi-quantitative numbers, based on so called house keeping gene expression. House keeping gene expression can be variable for the same subject as well as among human subjects.

While there is currently no FDA regulatory guidance in place that require in vitro assessment of susceptibility to drug transporters for filing a new drug application, many pharmaceutical companies anticipate that such data would be required in a near future. At present, there are no validated continuous cell lines that consistently express MRP1 and MDR1. Drug transport studies are often done with epithelial cells such as Caco-2, colon epithelial cells as a part of general, membrane permeability studies. Such studies only provide very limited information on the role of MRP1 and MDR1, due to the data only available from inhibitory effects. Details such as velocity and rate constant of new drug candidates and their derivatives require availability of recombinant cells such as those described here. The continuous cell lines according to the present invention can provide a standard for routine evaluation of new compounds to identify new drug candidates with most desirable pharmaceutical qualities. These drug qualities include high degree of tissue penetration, oral absorption, low metabolism and toxicity.

To manage potential drug interactions, the US FDA now requires data on the drug candidate's susceptibility to CYP450 enzymes as a part of preclinical characterization. The FDA guidance was a culmination of (1) availability of purified enzymes, (2) well-characterized in vitro methods, and (3) establishment of in vitro and in vitro correlates of key enzymes such as cytochrome P450 isozymes (e.g., CYP2D6, CYP3A, CYP2C9, CYP2C19). As cells that over expressed MDR1 and MRP1 become widely available for drug screening, evaluation of this membrane bound transporter function is expected to be standardized. The cell lines described in this invention provide such standards to accelerate identification of new compounds with desirable pharmaceutical properties and serve as a tool to predict drug penetration, absorption, distribution, elimination and bioavailability.

Another clinical use of the current invention is to develop immunodiagnostic assays for MRP2 and MDR1. Specific antibodies to these proteins can be prepared using as immunogens either the intact proteins themselves or specific peptide sequences therefrom. Such assays can be used by clinicians to assess, for example, the likelihood that a particular chemotherapeutic agent or drug regimen would be effective against the tumor. An assay would be performed by taking a biopsy from the target tumor, incubating it in vitro with labeled anti-MRP2 and/or anti-MDR1 and evaluating the immunohistochemical results.

The following examples are provided merely as illustrative of various aspects of the invention and shall not be construed to limit the invention in any way.

EXAMPLE 1

Impact of G1199A on Pgp-mediated Efflux Transport Activity

In this example, the significance of the MDR1 G1199A polymorphism, resulting in a Ser400Asn modification in P-glycoprotein is elucidated. Stable recombinant LLC-PK1 epithelial cells expressing either $MDR1_{wt}$ or $MDR1_{1199}$ have been developed to evaluate functional consequences of G1199A. Comparable expression of mRNA and protein in the MDR1-expressed cells and correct localization of P-glycoprotein in the apical membrane of recombinant cells was verified. The efflux transport of Rhodamine-123 in $MDR1_{1199}$ cells was approximately 4.5-fold lower than efflux in $MDR1_{wt}$ cells. Cytotoxicity studies have shown that $MDR1_{wt}$ and $MDR1_{1199}$ cells exhibited similar resistance to doxorubicin; however, $MDR1_{1199}$ cells were more resistant to vinblastine and vincristine. The apparent transepithelial permeability ratios of R123 in $MDR1_{wt}$ and $MDR1_{1199}$ cells were 3.54±0.94 and 2.02±0.51 ($p<0.05$), respectively. Therefore, the G1199A polymorphism alters the efflux and transepithelial permeability of a fluorescent substrate and sensitivity to select cytotoxic agents, which may influence drug disposition and therapeutic efficacy of some P-glycoprotein substrates.

Introduction

The human multidrug resistance gene (MDR1) encodes a 170 kilodalton integral membrane protein that mediates ATP-dependent substrate efflux. The protein product, P-glycoprotein, a member of the ATP-binding cassette (ABC) superfamily of transporters, resides in the plasma membrane and functions as an efflux transporter of a wide variety of natural compounds and lipophilic xenobiotics (reviewed in Lin et al., *Adv. Drug. Deliv. Rev.* 55:53-81 (2003)). While the contribution of P-glycoprotein in multidrug resistance for cancer chemotherapy is well documented, the role of P-glycoprotein in drug disposition is not fully understood and has continued to generate significant debate. P-glycoprotein mediates the energy-dependent efflux of a broad range of xenobiotics in epithelial tissues throughout the human body including the intestinal mucosa, liver canalicular membrane, kidney proximal tubules, blood-brain-barrier, and placenta (Schinkel, *Semin. Cancer Biol.* 8:161-70 (1997)). P-glycoprotein efflux may, therefore, act to decrease intestinal absorption, enhance biliary excretion and renal tubular secretion, and limit drug distribution to the fetus and brain. Because P-glycoprotein is found in tissues important in drug disposition, variation in expression and function of P-glycoprotein due to genetic polymorphisms of MDR1 may influence pharmacokinetics and, in turn, pharmacodynamics.

Recent progress has been made in identifying genetic polymorphisms in the MDR1 gene in normal human tissues. The first major screen of the MDR1 gene in 188 healthy Caucasian subjects, identified 15 single nucleotide polymorphisms; however, only one, a C→T transition at nucleotide position 3435 (C3435T), was shown to correlate with decreased intestinal P-glycoprotein expression and digoxin exposure in vivo (Hoffineyer et al., *Proc. Natl. Acad. Sci. USA* 97(7):3473-8 (2000)). As the C3435T polymorphism in exon 26 is a synonymous polymorphism that does not modify the amino acid sequence of P-glycoprotein, several investigators have searched for clues to the significance of C3435T. Another study reported that C3435T is linked to a non-synonymous G2677T polymorphism, resulting in an alanine to serine transition at amino acid 893, and another synonymous SNP, C1236T (Kim et al., *Clin. Pharmacol. Ther.* 70(2): 189-99 (2001)). Several other studies have attempted to link MDR1 polymorphisms, particularly C3435T, to changes in P-glycoprotein expression and function, and subsequent changes in drug disposition profiles. However, much of the data has been contradictory and inconclusive as to the influence of MDR1 SNPs and haplotypes on P-glycoprotein expression and in vivo drug disposition. A systematic study, designed to address genetic variants at the cellular and molecular level, is needed to define the functional significance of and the linkage between genetic polymorphisms of MDR1 and their impact on clinical pharmacokinetics.

Therefore, a recombinant expression system in epithelial cells capable of expressing P-glycoprotein variants in a reproducible manner to systematically study the influence of genetic polymorphisms in MDR1 has been developed. Thus far, in vitro studies in the literature to evaluate the influence of MDR1 polymorphisms on P-glycoprotein efflux have produced variable results. Discrepancies exist in the reported influence of G2677T and C3435T on P-glycoprotein activity in various vector and expression systems (Kim et al., *Clin. Pharmacol. Ther.* 70(2): 189-99 (2001); Kimchi-Sarfaty et al., *Mol. Pharmacol.* 62:1-6 (2002); Morita et al., *Biochem. Pharmacol.* 65:1843-52 (2003)). In addition, some transient expression systems used to evaluate changes in activity cannot be used to evaluate transepithelial transport, which is important in assessing drug uptake and permeability. Because linkage to C1236T and G2677T complicates the influence of C3435T, the functional role of the G1199A polymorphism has been evaluated as a model for recombinant P-glycoprotein expression system. MDR1 G1199A, which results in a serine to asparagine transition at amino acid 400 in a cytoplasmic domain of P-glycoprotein, has a reported allelic frequency of approximately 5.5% in Caucasians (Hoffineyer et al., *Proc. Natl. Acad. Sci. USA* 97(7):3473-8 (2000); Kim et al., *Clin. Pharmacol. Ther.* 70(2): 189-99 (2001); Cascorbi et al., *Clin. Pharmacol. Ther.* 69(3):169-74 (2001)). Thus far, G1199A has not been shown to be linked to other SNPs. The goal of this study was to develop a recombinant MDR1 expression system to evaluate the functional significance of G1199A in epithelial cells. The G1199A polymorphism was found to alter efflux and transepithelial transport as well as altering the sensitivity profiles of cells to cytotoxic drugs.

Methods

Cell Culture

LLC-PK1 control and transfected cells were grown in complete media consisting of RPM1 medium 1640 (Invitrogen, Carlsbad, Calif.) supplemented with 10% (v/v) fetal calf serum and 1% (v/v) antibiotic-antimycotic and grown at 37° C. in the presence of 5% $CO_2$. For deconvolution immunofluorescent microscopy and transepithelial transport studies, cells were grown in Medium 199 (Invitrogen) supplemented with L-glutamine, 10% (v/v) fetal calf serum, and 1% (v/v) antibiotic-antimycotic and grown at 37° C. in the presence of 5% $CO_2$.

Generation of $MDR1_{wt}$ and $MDR1_{1199}$ Plasmids

Total RNA was extracted from the MDR1-overexpressing cell line, MES-SA-DX5 and full-length MDR1 cDNA was generated using the high-fidelity protocol developed previously (Yang et al., *Biotechniques* 33:196, 8, 200 passim. (2002)). The isolated MDR1 cDNA was cloned into a linearized pCR3.1 TA vector (Invitrogen, Carlsbad, Calif.) containing cytomegalovirus (CMV) and T7 promoters capable of transcription also described previously (Yang et al., supra). The plasmid stock was designated as $MDR1_{wild\text{-}type}$ ($MDR1_{wt}$).

The plasmid containing the G1199A polymorphism was generated by subcloning a fragment containing the polymorphism into the $MDR1_{wt}$ plasmid utilizing the restriction enzyme, HindIII. This strategy employed two PCR steps to insert the 1199A variant and is further detailed in FIG. 1 Two pairs of primers were created. The first pair overlapped the G1199A region with the 1199A variation in the middle of the oligonucleotide: 5'CAGAAATGTTCACTTCAATTACCCATCTCGAAAAG 3' (residues 1182-1216; forward primer) (SEQ ID NO:6) and 5' TTTCGAGATGGGTAAT-TGAAGTG AACATTTCTG 3' (residues 1182-1214; reverse primer) (SEQ ID NO:7). The other set of primers overlapped the restriction enzyme sites for HindIII, one recognition site in the pCR3.1 vector, 5' GTTTAACTTAAGCTTGGTACC 3' (residues-697-674; forward primer) (SEQ ID NO:8), and one site in MDR1 cDNA, 5' GGTACTAAGCTTTCTGTCTT GG 3' (residues 2031-2052; reverse primer) (SEQ ID NO:9). The first PCR step generated two fragments containing 1199A at one end of the fragment and the HindIII site at the other end. The two fragments were annealed together and amplified using the HindIII primers. The amplified PCR fragment and the pCR3.1-hMDR1 plasmid were digested with HindIII and annealed together. Clones were screened by restriction enzyme mapping with PstI and EcoRI and the sequence was verified using Big-Dye 3.0 chemistry (Applied Biosystems, Foster City, Calif.) and an ABI Prism 377 DNA Sequencer (Applied Biosystems). The variant plasmid stock was designated $MDR1_{1199}$.

Isolation of Stable Recombinant Cells Expressing $MDR1_{wt}$ or $MDR1_{1199}$ The $MDR1_{wt}$ and $MDR1_{1199}$ plasmids were transfected into the porcine kidney epithelial cell line, LLC-PK1. Ten million cells were resuspended in complete media and transferred to a 0.4 cm electroporation cuvette (Bio-Rad Laboratories, Hercules, Calif.) with 10 μg of plasmid DNA (either $MDR1_{wt}$ or $MDR1_{1199}$). Electroporation was performed at 230 V and 975 μF in a Gene Pulser® II (Bio-Rad Laboratories). Cells were placed on ice for 10 min and cultured in complete media for selection. Transfected LLC-PK1 cells with the highest level of P-ilycoprotein expression were selected to generate stable cell lines expressing $MDR1_{wt}$ or $MDR1_{1199}$. Cells were treated for 3 days with 300 μg/mL G418, a neomycin derivative (Calbiochem, San Diego, Calif.). A fraction of the cells were briefly exposed for another 3 days to 5 μM doxorubicin (VHA PLUS®, Irving, Tex.), a cytotoxic P-glycoprotein substrate, and continued selection by G418 pressure. The cells expressing high levels of P-glycoprotein were further expanded and verified to have stable expression allowing for functional evaluation. Characterization of P-glycoprotein Expression Absolute quantitation of MDR1 mRNA transcripts in cellular samples was performed using the ABI Prism 7900HT Sequence Detection System (Applied Biosystems). An MDR1 RNA standard was generated by the method described previously, and concentration was measured by absorbance at 260 nm and converted to the number of copies of MDR1 RNA by the molecular weight (Yang et al., *Biotechniques* 33:196, 8, 200 passim. (2002)). A dilution series of the MDR1 RNA standard was used to generate a standard curve of the number of copies of MDR1 mRNA vs. $C_T$ value. Following RNA isolation, 100 ng of total RNA of each cellular sample was analyzed in triplicate to obtain a $C_T$ value and estimation of the number of copies of MDR1 mRNA.

Immunoblot analysis was used to detect protein expression; briefly, $2\times10^6$ cells were pelleted and lysed in a lysis buffer containing SDS and β-mercaptoethanol. Protein concentration was measured by a microplate assay protocol (Bio-Rad Laboratories). Electrophoresis and transfer was run according to instructions for Mini-PROTEAN® II Electrophoresis Cell and Mini Trans-Blot® Electrophoretic Transfer Cell (Bio-Rad Laboratories). Nitrocellulose blots were blocked with 5% evaporated milk in TTBS buffer (0.1% Tween 20; 20 mM Tris-HCl, 0.9% NaCl, pH 7.6). Immunoblotting was performed with the anti-P-glycoprotein monoclonal antibody F4 (Sigma, St. Louis, Mo.) followed by a secondary HRP-conjugated goat anti-mouse IgG. ECL reagents were used as a substrate and blots were exposed to X-ray film for visualization of the protein bands.

For deconvolution immunofluorescent microscopy, $4\times10^5$ cells were plated on glass chamber slides (8-well; Lab-Tek™; Nalge Nunc International, Rochester, N.Y.) and grown for 4 days. Cells were fixed with 2% paraformaldehyde in phosphate buffered saline (PBS) (pH 7.4) and permeabilized with 0.2% Triton X-100. Blocking was performed with 2% goat serum in PBS containing 1% BSA (PBS/BSA). Slides were immunostained with anti-P-glycoprotein monoclonal antibodies F4 (Sigma) and C219 (Calbiochem) followed by goat anti-mouse secondary antibody, Alexa-594 (Molecular Probes, Eugene, Oreg.). Slides were mounted with Fluoromount-G (Southern Biotechnology, Birmingham, Ala.) and images were collected with a Zeiss Axiovert 200 MAT deconvolution microscope (Carl Zeiss, Oberkochen, Baden-Wuerttemberg, Germany) with a 63× oil immersion objective lens, and analysis was performed with SlideBook 3.0® software (Intelligent Imaging Innovation, Denver, Colo.).

Intracellular Accumulation Assay

One million cells per well were plated overnight on 6-well plates (Corning, Corning, N.Y.). Cells were washed with PBS and incubated for 90 min in 5 μM Rhodamine-123 (R123) (Sigma) in serum-free RPM1 medium 1640. Cells were again washed with PBS and then allowed to efflux for 60 min in complete media. After efflux, cells were trypsinized, washed, and resuspended in 1% paraformaldehyde. Cells were analyzed with a FACScan flow cytometer (Becton Dickinson, Franklin Lakes, N.J.) using CellQuest software (Becton Dickinson). Ten thousand cells from each sample were analyzed for forward scatter, side scatter, and R123 accumulation. Inhibition was performed at 1 μM GF120918.

Cytotoxic Drug Sensitivity Assay

LLC-PK1 control and MDR1 recombinant cells were plated at a density of $1\times10^4$ cells/well in a 96-well plate in complete media and allowed to attach for 4 hours at 37° C. Varying concentrations of doxorubicin, vinblastine (Bedford Laboratories, Bedford, Ohio), and vincristine (Faulding, Paramus, N.J.) were added to the cells in quadruplicate. Cells were incubated with the cytotoxic drugs for 3 days at 37° C. On the second day of the incubation, 1 μCi of $^3$H-thymidine (specific activity: 81.1 Ci/mmole) was added to each well and incubated overnight. Cells were harvested on day 3 with a cell harvester.

Transepithelial Transport Assay

LLC-PK1 control and recombinant MDR1 cells were plated at a density of $2\times10^6$ cells/24 mm well on permeable supports (Transwell™; 3.0 μm membrane pore size; Corning) and grown for 4 days; media was refreshed after two days in culture. Fresh media was added to the cells one hour before the initiation of the experiment, and transepithelial electrical resistance (TEER) values were measured with a Millicell®-ERS (Millipore, Billerica, Mass.). For transport of R123 across the epithelial cells, 1 μM R123 in Opti-MEM (Invitrogen) was added to either the apical or basolateral compartments with fresh Opti-MEM medium added to the opposite side. Inhibition was performed at 1 μM GF120918. Aliquots of 50 μL were taken from apical and basal compartments at 1, 2, 3, and 4 hours. Fluorescence intensity of R123 was measured with a Gemini XS microplate spectrofluorometer (Molecular Devices, Sunnyvale, Calif.) with SoftMax Pro® software (Molecular Devices); excitation was set at 488 nm and emission at 525 nm. Apparent permeability ($P_{app}$) was calculated in the apical-to-basolateral direction ($P_{app\ A \rightarrow B}$) and in the basolateral-to-apical direction ($P_{app\ B \rightarrow A}$) as described by Polli et al. Briefly, $P_{app}=(1/(A*C_0))*(dQ/dt)$, where A is the surface area of permeable support, $C_0$ is the initial concentration in the donor compartment, and dQ/dt is the rate of transfer of compound into the acceptor compartment. The ratio of $P_{appB \rightarrow A}/P_{appA \rightarrow B}$ was also estimated to evaluate P-glycoprotein-mediated directional efflux.

RESULTS

Generation of Cells Expressing Recombinant $MDR1_{wt}$ or $MDR1_{1199}$

Figure 2:
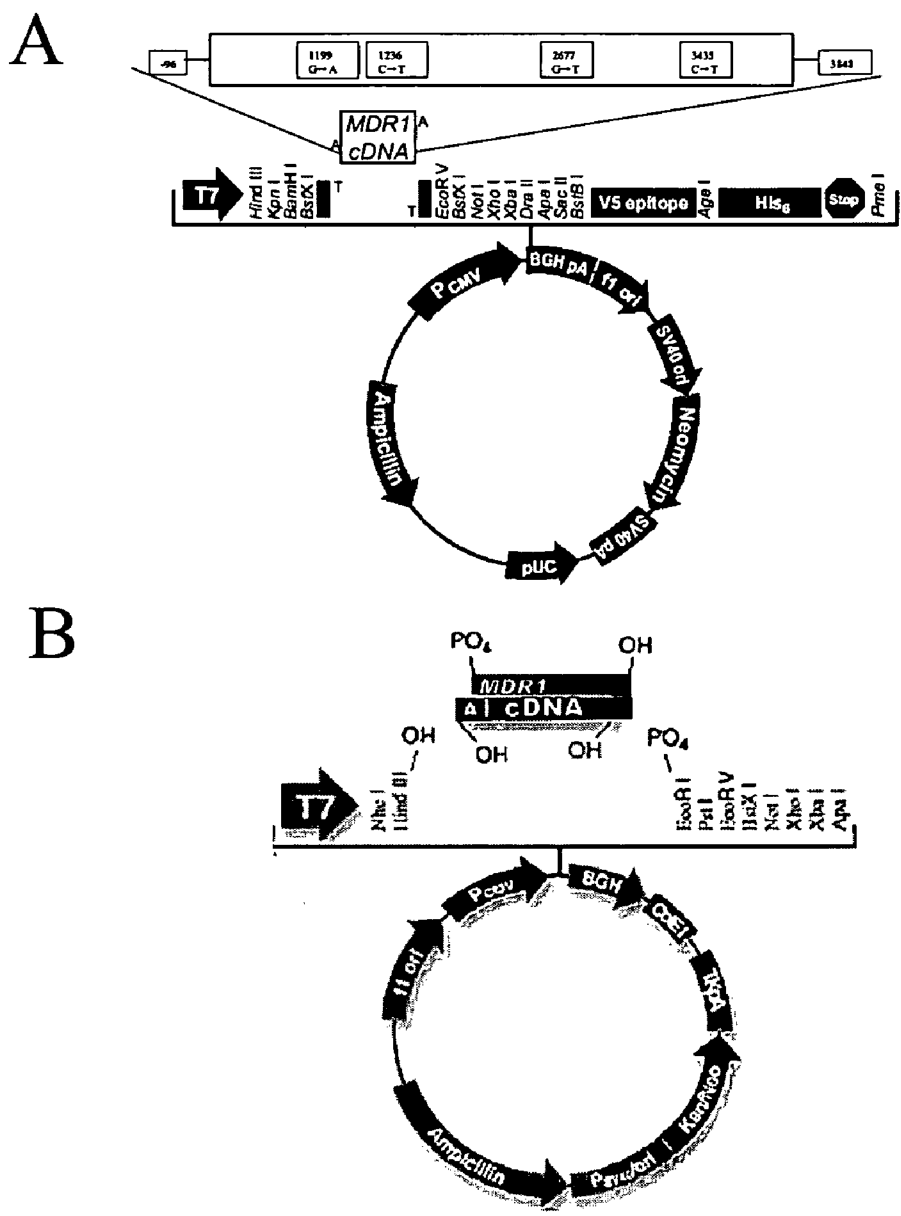
FIG. 2: Typical MDR1 or MRP1 cDNA plasmids designed to express in mammalian cells for generating stable recombinant cell-lines. Plasmid described in Panel A contains poly histidine tail to improve efficiency in isolation of recombinant protein, while the plasmid in Panel B lacks poly histidine tail. Both plasmids (Panel A and B) contain T7 promoter sequences to synthesize RNA standards for measurement of MDR1 (and MRP1) transcript levels in clinical samples. The same set of MDR1 and MRP1 plasmid vehicles could be used as standards for genotype determination.
Figure 3:
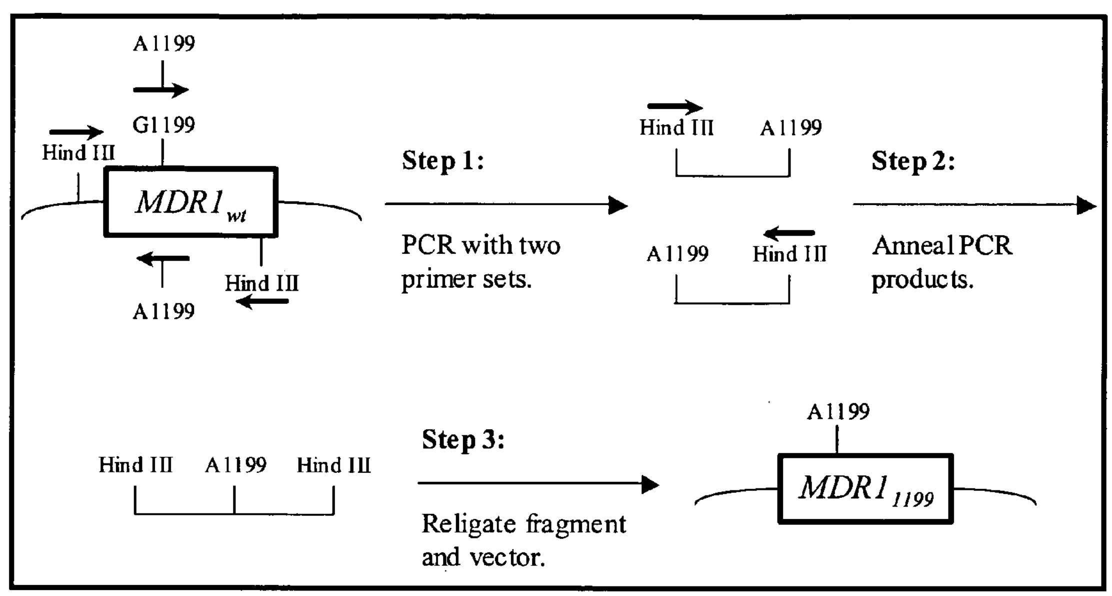
FIG. 3: Schematic representation of the generation of the $MDR1_{1199}$ plasmid. The $MDR1_{1199}$ plasmid was generated by introducing a 1199A variant into the original $MDR1_{wt}$ plasmid. The first step in generating the $MDR1_{1199}$ plasmid utilized the HindIII and 1199A primer sets to generate two fragments each containing 1199A at one end and a HindIII site at the other from the original $MDR1_{wt}$ plasmid. Next, the fragments were annealed and amplified using the HindIII primer set. Finally, the fragment containing 1199A and the pCR3.1-hMDR1 vector were digested with HindIII and relegated. The $MDR1_{1199}$ plasmid was validated by restriction enzyme and sequencing analyses. $MDR1_{wt}$ and $MDR1_{1199}$ plasmids contain T7 and CMV promoters and ampicillin- and neomycin-resistance genes.

MDR1 vectors were successfully constructed for mammalian cell expression containing either the wild-type or variant allele at nucleotide position 1199. The final plasmid constructs were verified by directly sequencing the MDR1 insert. The introduction of the 1199A polymorphism from a wild-type plasmid was based on a restriction enzyme approach, and is described in FIG. 3. These plasmids, referred to as $MDR1_{wt}$ and $MDR1_{1199}$ were used for generating stable recombinant cells for functional studies.

Figure 4:
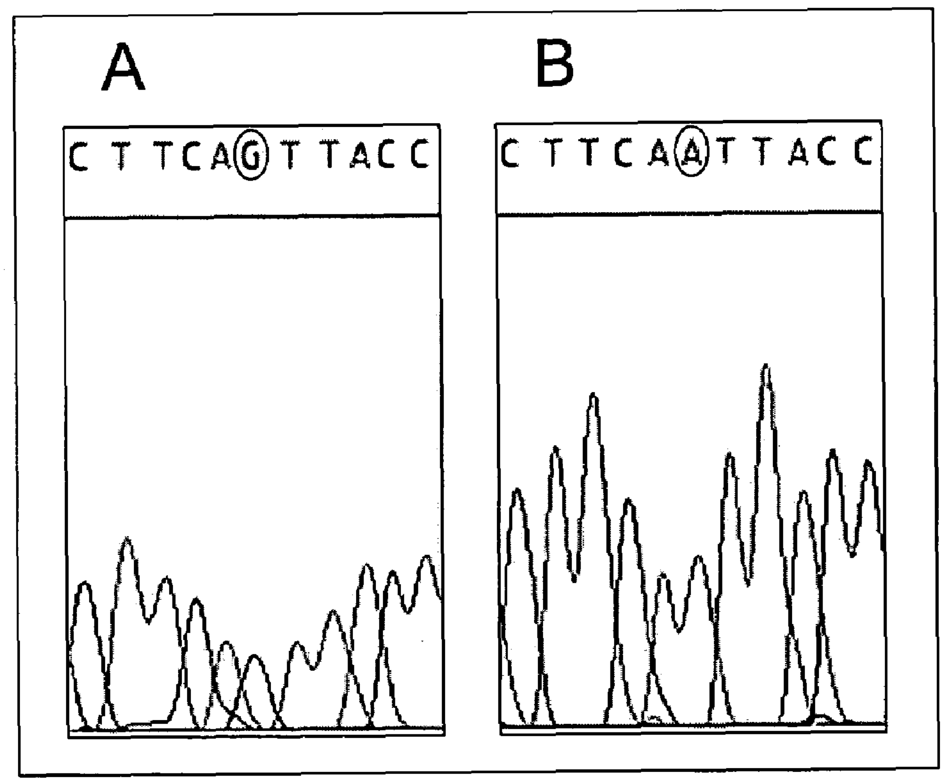
FIG. 4: Sequence verification of LLC-PK1 cells expressing $MDR1_{wt}$ and $MDR1_{1199}$. Recombinant MDR1-expressing LLC-PK1 cells were sequenced at nucleotide position 1199; wild-type allele G and variant allele A. Electropherograms of $MDR1_{wt}$ (panel A) and $MDR1_{1199}$ (panel B) are shown.

LLC-PK1 cells were selected as the host to isolate stable epithelial cells for continuous expression of MDR1. These cells differentiate to form polarized monolayers for transepithelial efflux studies. As mammalian cells, LLC-PK1 should provide proper post-translational modification, which has been demonstrated to play a role in P-glycoprotein function (Loo et al., *J. Biol. Chem.* 268:19965-72 (1993); Loo et al., *J. Biol. Chem.* 268:3143-9 (1993); Loo et al., *J. Biol. Chem.* 269:7243-8 (1994); Loo et al., *Biochem.* 33:14049-57 (1994)). To further reduce the baseline levels of P-glycoprotein-like activity in these cells, a line of LLC-PK1 cells was selected and cloned that was P-glycoprotein negative based on its retention of R123 and sensitivity to the cytotoxic P-glycoprotein substrate doxorubicin. P-glycoprotein-deficient LLC-PK1 cells were transfected with respective plasmids by electroporation, and systematically selected for high levels of P-glycoprotein expression. The recombinant cells expressing $MDR1_{wt}$ or $MDR1_{1199}$ in a stable and consistent manner were cloned and expanded for functional studies. Direct sequencing was performed to verify expression of the correct allele at nucleotide position 1199 (FIG. 4). P-glycoprotein activity was maintained for more than 100 days in culture with greater than 95% of $MDR1_{wt}$ and $MDR1_{1199}$ recombinant cell populations excluding R123, as measured by flow cytometry. These cells also retained P-glycoprotein activity after being frozen in liquid nitrogen and thawed.

Characterization of P-glycoprotein Expression in Recombinant LLC-PK1 Cells

Figure 5:
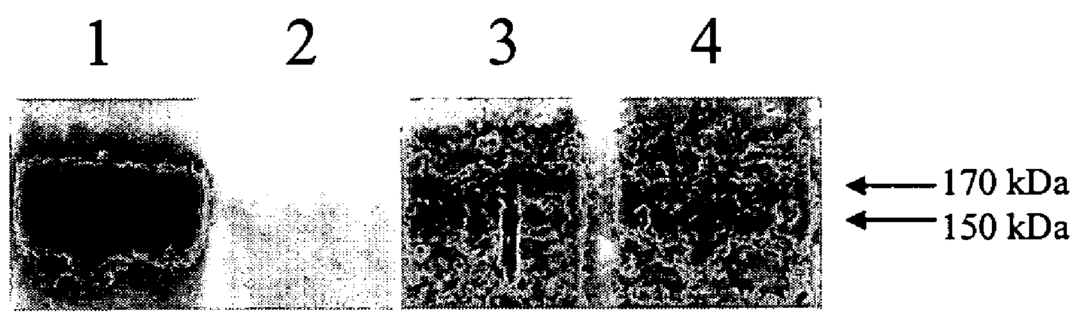
FIG. 5: Immunoblot analysis of LLC-PK1 control and recombinant MDR1 cells. Lane 1: P-glycoprotein positive control isolated from P-glycoprotein over-expressed cell line, MES-SA-DX5; lane 2: LLC-PK1 control cells; lane 3: recombinant $MDR1_{wt}$ cells; lane 4: recombinant $MDR1_{1199}$ cells.
Figure 6:
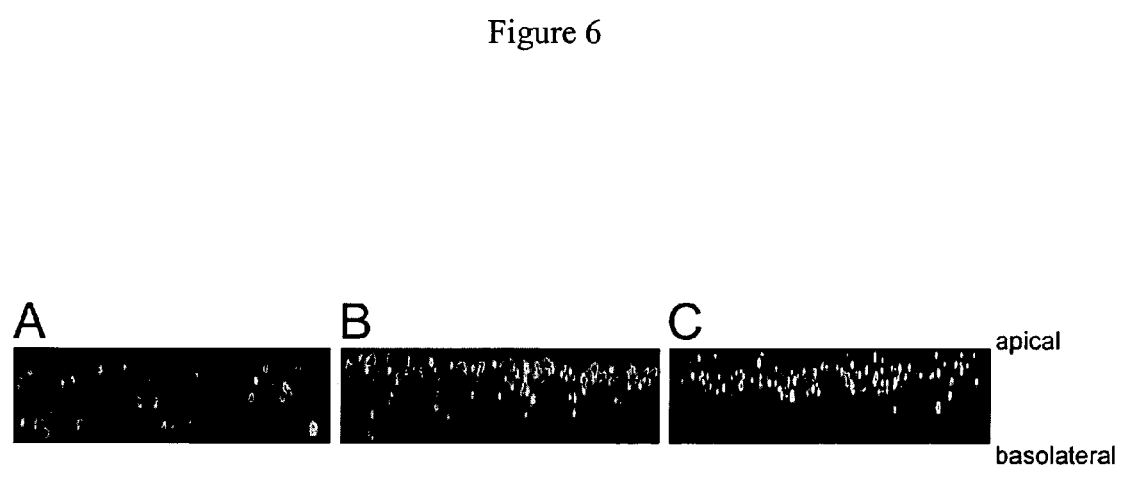

After transfection and selection of control and variant 1199 plasmids, it was important to verify MDR1 mRNA and protein expression. The level of MDR1 mRNA transcripts in MDR1 recombinant cells was assessed using an MDR1 standard that was generated with known copy number. MDR1 copy number values were similar in $MDR1_{wt}$ and $MDR1_{1199}$ recombinant cells with estimations of $2.90\times10^6\pm0.30$ and $3.51\pm10^6\pm0.30$ copies of MDR1 mRNA/100 ng total RNA, respectively. Immunoblot analyses of LLC-PK1 cells, normalized by protein concentration, showed approximately equal expression of 150 and 170 kDa bands of P-glycoprotein in $MDR1_{wt}$ and $MDR1_{1199}$ cells (FIG. 5). Image deconvolution confirmed that $MDR1_{wt}$ and $MDR1_{1199}$ cells express similar amounts of P-glycoprotein and that expression is predominantly on the apical membrane (FIG. 6).

P-glycoprotein-Mediated R123 Efflux

Figure 7:
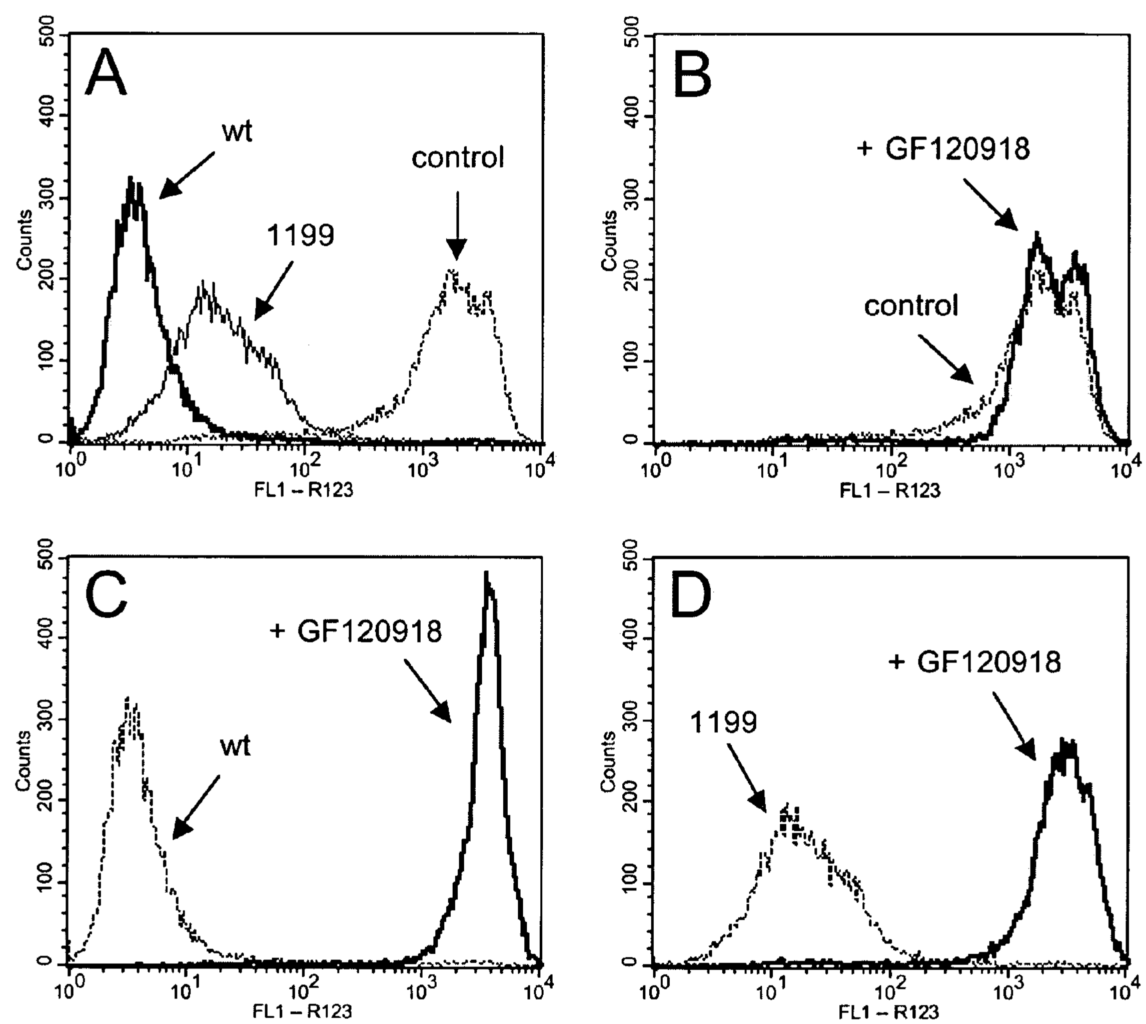
FIG. 7: P-glycoprotein mediated efflux of R123 in LLC-PK1 control and MDR1 recombinant cells. The intensity of intracellular R123 was evaluated by flow cytometry in LLC-PK1 control and MDR1 cells (panel A): control (dashed line), $MDR1_{wt}$ cells (bold line), and $MDR1_{1199}$ cells (solid line). The specificity of R123 efflux was evaluated in the absence (dashed line) and presence (solid line) of 1 μM GF120918; LLC-PK1 control cells (panel B); recombinant $MDR1_{wt}$ cells (panel C); recombinant $MDR1_{1199}$ cells (panel D).

Efflux transport activity of $MDR1_{wt}$ or $MDR1_{1199}$ recombinant cells was evaluated by flow cytometry with a fluorescent P-glycoprotein substrate R123. A fluorescent-activated cell sorter (FACS) was used to evaluate P-glycoprotein activity in a population of cells by measuring intracellular R123 accumulation. Mean intracellular R123 fluorescence for $MDR1_{wt}$ and $MDR1_{1199}$ cells (given in arbitrary units) were $3.91\pm0.11$ and $18.56\pm0.46$ ($p<0.001$), respectively, an approximate 4.75-fold higher accumulation of R123 in $MDR1_{1199}$ cells (FIG. 7A). To verify that the R123 efflux observed was due to P-glycoprotein activity, a specific and potent P-glycoprotein inhibitor GF120918 was used for R123 efflux assessment. Although there was differential efflux observed between cells expressing $MDR1_{wt}$ or $MDR1_{1199}$ R123 efflux activity was completely abolished in both types of cells, reversing cellular R123 accumulation similar to that of control LLC-PK1 cells (FIG. 7B-D). These results demonstrate that recombinant cells expressing $MDR1_{wt}$ or $MDR1_{1199}$ proteins are both capable of mediating P-glycoprotein-specific R123 transport activity, but cells expressing $MDR1_{1199}$ are less efficient than those expressing $MDR1_{wt}$.

TABLE 4

Sensitivities of LLC-PK1 control and recombinant MDR1 cells to cytotoxic P-glycoprotein substrates.

| LLC-PK1 | $EC_{50}$ values in nM (fold-change from control) | | |
|---|---|---|---|
| Cells | DOXORUBICIN | Vinblastine | Vincristine |
| CONTROL | 34.2 ± 3.1 | 0.66 ± 0.22 | 0.37 ± 0.12 |
| $MDR1_{wt}$ | 155 ± 68 (4.53) | 1.41 ± 0.51 (2.14) | 1.18 ± 0.56 (3.19) |
| $MDR1_{1199}$ | 120 ± 32 (3.51) | 15.7 + 4.0 (23.8)** | 3.41 ± 1.47 (9.23)* |

*Sensitivity to vincristine of $MDR1_{1199}$ compared $MDR1_{wt}$ ($p < 0.05$).
**Sensitivity to vinblastine of $MDR1_{1199}$ compared $MDR1_{wt}$ ($p < 0.005$).

Sensitivity to Cytotoxic Agents

To evaluate the impact of differential efficiency in efflux activity of cells expressing $MDR1_{wt}$ or $MDR1_{1199}$, three chemotherapeutic agents were employed that have been shown to exhibit P-glycoprotein-dependent drug resistance. Dose response analysis was performed for doxorubicin, vincristine and vinblastine. Drug sensitivity was expressed as the effective concentration necessary to kill 50% of the cells ($EC_{50}$). $EC_{50}$ values of the cytotoxic drugs in LLC-PK1 control and $MDR1_{wt}$ and $MDR1_{1199}$ cells are presented in Table 4. Recombinant cells expressing $MDR1_{wt}$ or $MDR1_{1199}$, exhibit significantly enhanced resistance to doxorubicin compared to the control cells, but their sensitivity to doxorubicin appears to be similar. A significant degree of resistance toward vinblastine and vincristine was also observed for both $MDR1_{wt}$ and $MDR1_{1199}$ cells; however, cells expressing $MDR1_{1199}$ were found to be more resistant to vinblastine and vincristine (about 11- and 2.9-fold respectively; Table 4) than those expressing $MDR1_{wt}$. Collectively, these data indicate that the P-glycoprotein product derived from $MDR1_{1199}$ exhibits differential sensitivity to vincristine and vinblastine compared to $MDR1_{wt}$ without significantly altering sensitivity to doxorubicin. TRANSEPITHELIAL TRANSPORT Differences in transcellular directional permeability in epithelial cells expressing $MDR1_{wt}$ and $MDR1_{1199}$ were evaluated by growing cells on a filter supports, providing for the establishment of polarized monolayers and tight junctions. P-glycoprotein is a directional transporter expressed on the apical membrane of epithelial cells and effluxes substrates in a basolateral-to-apical direction. TEER values, verifying the integrity of the monolayers and formation of tight junctions before an experiment, were 358±47.8 Ω*cm². The directional efflux transport was evaluated with a fluorescent substrate R123.

TABLE 5

Apparent permeability ratios for Rhodamine-123 transport in LLC-PK1 control and recombinant MDR1 cells.

| | $P_{appB \to A}/P_{appA \to B}$ | |
|---|---|---|
| LLC-PK1 Cells | R123 | R123 + GF120918 |
| CONTROL | 0.903 ± 0.200 | 1.01 ± 0.33 |
| $MDR1_{wt}$ | 3.54 ± 0.94† | 0.961 ± 0.216 |
| $MDR1_{1199}$ | 2.02 ± 0.51*† | 0.561 ± 0.030 |

*Apparent permeability ratio of $MDR1_{1199}$ compared to $MDR1_{wt}$ ($p < 0.05$)
†Apparent permeability ratio of $MDR1_{wt}$ and $MDR1_{1199}$ compared to LLC-PK1 control ($p < 0.01$)

Figure 8:
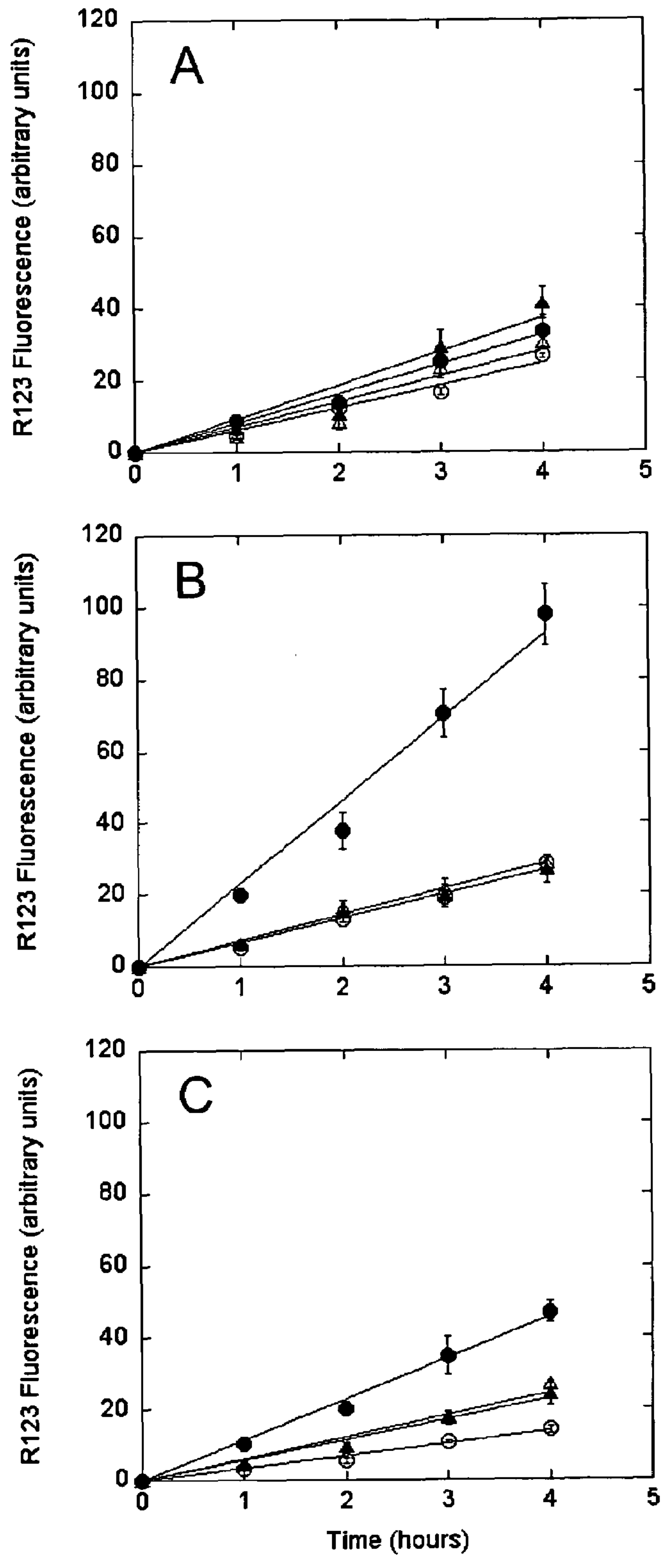
FIG. 8: Transepithelial transport across LLC-PK1 epithelial cells. Transepithelial permeability was evaluated as the amount of R123 transported across an epithelial monolayer from the donor to recipient compartment over a 4 hour time period; LLC-PK1 control cells (panel A); recombinant $MDR1_{wt}$ cells (panel B); recombinant $MDR1_{1199}$ cells (panel C). R123 transport in the basolateral-to-apical direction without inhibitor (•) and with 1 μM GF120918 (○) and in the apical-to-basolateral direction without inhibitor (▲) and with 1 μM GF120918 (Δ).

The permeability ratios ($P_{appB \to A}/P_{appA \to B}$) were calculated for comparison. If cells display directional efflux mediated by P-glycoprotein, a ratio greater than 1.0 is expected, and in the presence of a P-glycoprotein-specific inhibitor, GF120918, the ratio should be reduced to near 1.0. Both $MDR1_{wt}$ and $MDR1_{1199}$ cells show increased basolateral-to-apical efflux and permeability ratios compared to control cells (FIG. 8 and Table 5). However, cells expressing $MDR1_{1199}$ appear to have decreased directional efflux and permeability ratios of R123 compared to $MDR1_{wt}$. In the presence of GF120918, a specific P-glycoprotein inhibitor, directional transport is eliminated, suggesting that the directional efflux is P-glycoprotein mediated (FIG. 8 and Table 5).

Discussion

Due to the broad substrate specificity and localization in tissues, the importance of P-glycoprotein-mediated efflux transport in drug delivery and disposition is becoming increasingly appreciated. Significant progress has been made in the discovery of MDR1 polymorphisms and the assessment of allelic frequencies. The search for key genetic determinants, including MDR1 genetic polymorphisms, which alter the disposition of drugs that are substrates or inhibitors of P-glycoprotein in individuals, has just begun. Toward this end, stable recombinant LLC-PK1 cells expressing either $MDR1_{wt}$ or $MDR1_{1199}$, have been developed for evaluating the significance of the G1199A polymorphism.

Alterations in the efflux transport and chemoresistance of P-glycoprotein due to the G1199A transition have been observed in the recombinant expression systems described herein. Variations in efflux were demonstrated with the fluorescence substrate R123; cells expressing $MDR1_{1199}$ displayed decreased efflux of R123 compared to $MDR1_{wt}$. Regardless of the efficiency of efflux, cells expressing either $MDR1_{wt}$ or $MDR1_{1199}$ were both inhibited to the same degree by a P-glycoprotein-specific inhibitor, GF120918. This indicates that the observed differences were due to the influence of an MDR1 polymorphism on P-glycoprotein function. Variation in chemoresistance due to G1199A polymorphism was also observed (Table 4). Cells expressing $MDR1_{1199}$ appear to be more resistant to vinblastine and vincristine than cells expressing $MDR1_{wt}$; however, $MDR1_{wt}$ and $MDR1_{1199}$ recombinant cells displayed similar resistance to doxorubicin. Site-directed mutagenesis studies have also shown that modifications in the nucleotide sequence of MDR1 alters substrate efflux of some anticancer agents but does not cause a change in efflux of others (Loo et al., *J. Biol. Chem.* 268:19965-72 (1993); Loo et al., *J. Biol. Chem.* 268:3143-9 (1993); Loo et al., *J. Biol. Chem.* 269:7243-8 (1994); Loo et al., *Biochem.* 33:14049-57 (1994)). Multiple binding domains in the drug-binding pocket of P-glycoprotein have been proposed and may account for the drug-specific alteration in P-glycoprotein efflux due to genetic polymorphisms (Martin et al., *Mol. Pharmacol.* 58:624-32 (2000); Loo et al., *J. Biol. Chem.* 268:19965-72 (1993); Loo et al., *J. Biol. Chem.* 268:3143-9 (1993)). The observed differential sensitivity to cytotoxic agents due to G1199A may be important in modulating the efficacy of chemotherapy. The reported results could be used to provide alternate choices of drugs to overcome chemoresistance in some cancer patients. The use of LLC-PK1 epithelial cells as host cells allows for assessment of the role of MDR1 genetic variation in P-glycoprotein-dependent directional transcellular efflux. Permeability and directional efflux transport studies with the epithelial cells demonstrated that $MDR1_{1199}$ recombinant cells exhibited a lower $P_{appB \to A}/P_{appB \to A}$ ratio for R123 (Table 5). Changes in drug permeability may impact absorption, bioavailability, and distribution into target tissues, including the CNS.

The variations in P-glycoprotein activity due to G1199A found in the recombinant expression system are not comparable to those reported on $MDR1_{1199}$ expressed in HeLa cervical adenocancinoma cells using a vaccinia virus-based transient expression system (Kimchi-Sarfaty et al, *Mol. Pharmacol.* 62:1-6(2002)). However, the HeLa cell system cannot evaluate transcellular permeability, which is an especially important component of P-glycoprotein activity, particularly in intestinal absorption and blood-brain-barrier penetration. In this transient expression system, HeLa cells expressing $MDR1_{1199}$ did not exhibit significant differences in efflux of bodipy-FL-verapamil, bodipy-FL-vinblastine, calcein-AM, bodipy-FL-prazosin, bisantrene, and bodipy-FL-forskolin, and daunorubicin (Kimchi-Sarfaty et al, supra.). However, the fluorescent bodipy modification on the P-glycoprotein substrates in this study may influence the ability to detect functional variability due to MDR1 polymorphisms. It is also possible that expression of some vaccinia viral elements and cytolytic viral proteins in these transient expressed HeLa cells contribute to the discordance. The system allows for long-term expression of P-glycoprotein variants without the complication of viral elements.

The role of stable recombinant epithelial cells for expression of P-glycoprotein and variants should not be underestimated. Data in literature contains many contradictory reports of in vitro studies performed to evaluate the influence of MDR1 polymorphisms (primarily G2677T and C3435T) on P-glycoprotein efflux at the cellular level. In vitro retroviral vectors containing MDR1 variants at 2677, designed to express Ala893 or Ser893 in NIH-3T3 mouse embryonic cells, suggested that Ser893-expressing cells exhibited decreased digoxin accumulation than Ala893 cells indicating enhanced P-glycoprotein efflux (Kim et al., *Clin. Pharmacol. Ther.* 70(2):189-99 (2001)). On the other hand, a vaccinia virus-based transient expression system of several MDR1 polymorphisms (A61G, T307C, G1199A, G2677T, and G2995A) in HeLa cells showed no difference in P-glycoprotein expression and efflux of various drugs (Kimchi-Sarfaty et al, *Mol. Pharmacol.* 62:1-6(2002)). Similarly, expression of different combinations of variations at 2677 and 3435 in LLC-PK1 cells (2677G/3435C, 2677G/3435T, 2677A/3435C, 2677A/3435T, 2677T/3435C, 2677T/3435T) were shown to have no apparent difference in transcellular transport and accumulation of verapamil, digoxin, vinblastine, and cyclosporine (Morita et al., *Biochem. Pharmacol.* 65:1843-52 (2003)). At present, the data in the literature provide no consistent information on the influence of MDR1 polymorphisms in vitro.

There are several reasons that can account for the discrepancies observed between the in vitro observations of various groups of researchers. As described earlier, multiple binding domains may exist in P-glycoprotein, and variations in the amino acid sequence of the protein may alter binding and efflux of some drugs but not others. Therefore, the selection of substrates may be important in assessing changes in P-glycoprotein activity and could explain some observed differences. Also, some vectors carry unique membrane components that may influence the activity of P-glycoprotein. The cells used to express the variant MDR1 genes can also have variable intrinsic transporters, many of which contribute to the efflux of P-glycoprotein substrates. The recombinant expression system we have developed to generate cell lines that continuously express MDR1 variants will be useful for study in detailing the complex interactions of MDR1 polymorphisms.

The expression system described herein, including MDR1 mammalian expression vectors and epithelial host cells capable of reproducibly expressing P-glycoprotein variants and differentiating into polarized monolayers. This strategy can be readily adapted to investigate other SNPs and haplotypes of MDR1 and provide insight into the functional significance on the more than 30 SNPs reported in the literature. For instance, the influence of C3435T can be evaluated to determine whether or not this synonymous polymorphism changes expression or activity of P-glycoprotein, with which it has been reported to be associated. In addition, the effect of MDR1 haplotypes can also be evaluated in this system since multiple SNPs can be expressed at once in the same plasmid. Multiple SNPs found on the same chromosome are assigned to a specific haplotype, and some attempts have been made to determine the role of MDR1 haplotypes in P-glycoprotein variability but the data is still inconclusive ((Kim et al., *Clin. Pharmacol. Ther.* 70(2): 189-99 (2001); Johne et al., *Clin. Pharmacol. Ther.* 72:584-94 (2002); Kroetz et al., *Pharmacogenetics* 13:481-94 (2003)). The expression systems can be useful in sorting out the role of MDR1 haplotypes.

Mammalian epithelial host cells similar to LLC-PK1, including MDCKII and Caco-2, can be used for evaluating the significance of MDR1 polymorphisms (Polli et al., *J. Pharmacol. Exp. Ther.* 299:620-8 (2001); Williams et al., *J. Pharm. Sci.* 92:1957-67 (2003); Zhang et al., *Pharm. Res.* 15:1520-4 (1998); Stormer et al., *Drug. Metab. Dispos.* 29:954-6 (2001)). The same MDR1 and variant constructs can be used to generate recombinant expression systems with these cells. The described stable recombinant cells have provided a unique method for evaluating MDR1 genetic polymorphisms. Since LLC-PK1 recombinant cells can be grown continuously in culture for several passages, they can serve as an in vitro tool to detect potential drug-drug interactions in drug development. This continuous system focuses on genetic modifications in the coding region of MDR1 that alter the structure of P-glycoprotein. In addition, other strategies specifically designed to evaluate the effects of promoter and intronic SNPs can be used to address regulation of MDR1 expression.

EXAMPLE 2

Impact of G1199T on Pgp-mediated Drug Resistance

Methods

Cell Culture

Human embryonic kidney cell, HEK293 cells (with or without Pgp expression) were grown at 37° C. in complete media consisting of DMEM medium (Invitrogen, Carlsbad, Calif.) supplemented with 10% (v/v) fetal calf serum and 1% (v/v) antibiotic-antimycotic, 1% non-essential amino acid, and under 5% $CO_2$.

Generation of $MDR1_{wt}$ and $MDR1_{1199}$ Plasmids

Total RNA was extracted from the MDR1-overexpressing cell line, MES-SA-DX5 and full-length MDR1 cDNA was generated using the high-fidelity protocol developed previously (Yang et al., *Biotech.* 33:196, 8, 200 passim. (2002)). The isolated MDR1 cDNA was cloned into a linearized pcDNA-TA vector (Invitrogen, Carlsbad, Calif.) containing cytomegalovirus (CMV) and T7 promoters capable of transcription also described previously (Yang et al., supra.). The plasmid stock was designated as $MDR1_{wild-type}$ ($MDR1_{wt}$).

The mammalian expression plasmid containing the G1199A or G1199T polymorphism was generated by site-directed mutagenesis (Stratagene, la Jolla, Calif.). Details of this expression plasmid designed to express Pgp in mammalian cells have been published (Woodahl et al., 2004). Briefly, for G1199A, the primers used are: Forward 5'-3° CAGAAATGTTCACTTCAATTACCCATCTCGAAAAG (SEQ ID NO:6), and Reverse 5'-3' TTTCGAGATGGGTAATTGAAGTGAACATTTCTG (SEQ ID NO:7). For G1199T, the primers are: forward 5'-3' CAGAAATGTTCACTTCATTTACCCATC TCGAAAAG (SEQ ID NO:10), and reverse 5'-3' TTTCGAGATGGGTAAATGAAGTG AACATTTCTG (SEQ ID NO: 11). Clones were screened by restriction enzyme mapping with EcoRI and Bam HI and the sequence was verified with an automated DNA sequencer based on Big-Dye 3.0 chemistry (Applied Biosystems, Foster City, Calif.). The variant expression plasmids were designated as $MDR1_{1199}$A or $MDR1_{1199T}$.

Isolation of Stable Recombinant Cells Expressing $MDR1_{wt}$ or $MDR1_{1199}$ The $MDR1_{wt}$, $MDR1_{1199A}$, or $MDR1_{1199T}$ plasmids were introduced into the mammalian cell, HEK293 by electroporation. Ten million cells with 10 μg of plasmid DNA (either $MDR1_{wt}$ or $MDR1_{1199}$) were suspended in a 0.4 cm electroporation cuvette containing HBSS. Electroporation was performed at 250 V and 975 μF in a Gene Pulser® II (Bio-Rad Laboratories, Hercules, Calif.). Subsequently, cells were kept at 4° C. for 10 min and before returning to the original cell culture conditions. These cells were initially exposed for 3 days with 300 μg/mL G418, a neomycin derivative (Calbiochem, San Diego, Calif.) to select for cells that express neomycin under the direction of the same plasmid vector. The G418 resistance cells were further expanded and verified to have stable, high levels of P-gp expression. These cells, verified to stably express high levels of Pgp are used subsequently for functional studies.

Characterization of P-gp Expression

Absolute quantitation of MDR1 mRNA transcripts in cellular samples was performed using the ABI Prism 7900HT Sequence Detection System (Applied Biosystems). An MDR1 RNA standard was generated by the method described previously, and concentration was measured by absorbance at 260 nm and converted to the number of copies of MDR1 RNA by the molecular weight (Yang et al., *Biotech.* 33:196, 8, 200 passim. (2002)). A dilution series of the MDR1 RNA standard was used to generate a standard curve of the number of copies of MDR1 mRNA vs. $C_T$ value. Following RNA isolation, 100 ng of total RNA of each cellular sample was analyzed in triplicate to obtain a $C_T$ value and estimation of the number of copies of MDR1 mRNA.

Immunoblot analysis was also used to verify protein expression. Briefly, $2\times10^6$ control and recombinant Pgp expressed cells were pelleted and lysed in a lysis buffer containing SDS and β-mercaptoethanol. Protein concentration was measured by a microplate assay protocol (Bio-Rad Laboratories). Electrophoresis and transfer was run according to instructions for Mini-PROTEAN® II Electrophoresis Cell and Mini Trans-Blot® Electrophoretic Transfer Cell (Bio-Rad Laboratories). Non specific binding sites on the membrane were blocked with 5% evaporated milk in TTBS buffer (0.1% Tween 20; 20 mM Tris-HCl, 0.9% NaCl, pH 7.6). Subsequently the nitrocellulose membrane was incubated with the F4 (Sigma, St. Louis, Mo.), anti-P-gp monoclonal antibody followed by a secondary HRP-conjugated goat anti-mouse IgG. ECL reagents were used as a substrate and blots were exposed to X-ray film to detect anti-Pgp reactive protein bands.

Cell surface expression of P-gp was also analyzed by flow cytometry. Briefly, $5\times10^5$ cells were plated overnight on 6-well plates (Corning, Corning, N.Y.). Cells were fist washed with phosphate buffered saline with 0.5% bovine serum albumin (PBS/BSA) and detached after 10 min incubation with 2 mM EDTA in PBS. They were incubated with either anti-P-gp monoclonal F4 or a control (matched-isotype mouse) antibody for 30 min at 4° C., followed by three washes with cold Hanks' balanced salt solution supplemented with 0.5% BSA and 0.1% $NaN_3$ (HBSS-BSA-$NaN_3$). Cells were then incubated with phycoerythrin (PE)-conjugated goat-anti-mouse IgG (Calbiochem, San Diego, Calif.) for 30 min on ice in the dark, again followed by three washes with HBSS-BSA-$NaN_3$. Cells were resuspended in HBSS-BSA-$NaN_3$ and cell surface fluorescence was analyzed with a FACScan flow cytometer (Becton Dickinson, Franklin Lakes, N.J.) using CellQuest software (Becton Dickinson). Pgp expressed cell distribution was determined after accounting for cells that were reactive to non-specific antibody binding.

For immunofluorescence staining and confocal microscopic studies, $4\times10^5$ cells were plated on glass chamber slides (8-well; Lab-Tek™; Nalge Nunc International, Rochester, N.Y.) and grown for 4 days. Cells were fixed with 2% paraformaldehyde in PBS (pH 7.4) and permeabilized with 0.2% Triton X-100. Blocking was performed with 2% goat serum in PBS containing 1% BSA (PBS/BSA). Slides were immunostained with anti-P-gp monoclonal antibodies F4 (Sigma) and C219 (Calbiochem) followed by goat anti-mouse secondary antibody, Alexa-594 (Molecular Probes, Eugene, Oreg.). Slides were mounted with Fluoromount-G (Southern Biotechnology, Birmingham, Ala.) and images were collected with a Zeiss Axiovert 200 MAT deconvolution microscope (Carl Zeiss, Oberkochen, Baden-Wuerttemberg, Germany) with a 63× oil immersion objective lens, and analysis was performed with SlideBook 3.0® software (Intelligent Imaging Innovation, Denver, Colo.).

Intracellular Accumulation Assay

One million cells per well were plated overnight on 6-well plates (Corning). For Rhodamine-123 (R123) accumulation, cells were washed with PBS and incubated for 90 min in 5 μM R123 (Sigma) in serum-free RPM1 medium 1640 at 37° C. Cells were again washed with PBS and then allowed to efflux for 60 min in complete media. After efflux, cells were washed in ice-cold PBS, trypsinized, and resuspended in 1% paraformaldehyde. Cells were analyzed with a FACScan flow cytometer (Becton Dickinson) using CellQuest software (Becton Dickinson). Ten thousand cells from each sample were analyzed for forward scatter, side scatter, and R123 accumulation.

Inhibition analyses were performed with the specific inhibitor GF120918 [N-(4-[2-(1,2,3,4-tetrahydro-6,7-dimethoxy-2-isoquinolinyl)ethyl]-phenyl)-9,10-dihydro-5-methoxy-9-oxo-4-acridine carboxamide]. Inhibitory potency was evaluated by calculating concentration necessary for 50% inhibition ($IC_{50}$) values as the percent inhibition of R123 efflux in the presence of GF120918 over a concentration range from 2 nM to 2 μM. The $IC_{50}$ values were estimated using a sigmoid Emax model on WinNonlin® software (Pharsight, Mountain View, Calif.). Complete inhibition was performed at 1 μM GF120918.

Doxorubicin accumulation was performed in quadruplicate by incubating cells with 10 μM doxorubicin in PBS with 0, 20, 100, or 1000 nM GF120918 for 1 hour at 37° C. Cells were washed with ice-cold PBS, trypsinized, and lysed in 0.5% deoxycholic acid. To precipitate the proteins tricholoracetic acid was added to 5% and the cell lysates were incubated for 30 min at 4° C. and centrifuged at 20,000 g. The supernatant was removed and fluorescence intensity of doxorubicin was measured with a fluorescence spectrophotometer F-4500 (Hitachi Instruments, San Jose, Calif.); excitation was set at 488 nm and emission at 560 nm.

Cytotoxic Drug Sensitivity Assay

HEK293 control and MDR1 recombinant cells were plated at a density of $1\times10^4$ cells/well in a 96-well plate in complete media and allowed to attach for 4 hours at 37° C. Varying concentrations of doxorubicin, paclitaxol (Sigma Aldrich), vinblastine (Bedford Laboratories, Bedford, Ohio), and vincristine (Faulding, Paramus, N.J.) were added to the cells in triplicate. Cells were incubated with the cytotoxic drugs for 3 days at 37° C. On day 3, the media was removed and replaced with OptiMEM. The MTS cell viability assay was performed and cytotoxicity was measured as the effective concentration necessary for 50% cell growth inhibition ($EC_{50}$) for each drug; $EC_{50}$ values were estimated using a sigmoid Emax model on WinNonlin® software (Pharsight, Mountain View, Calif.).

Results

Identification and validation of G1199T variant in leukemia patients

As a part of an effort to identify MDR1 coding sequence variations, MDR1 RNA from lymphoblast and bone marrow cells of leukemia patients was isolated and the entire 3.8 kb regions of the MDR1 RNA were sequenced. These sequence data were confirmed by comparing the DNA sequence data derived from the forward and reverse sequences derived from positive and negative DNA strands. Based on the MDR1 sequence data collected from 44 leukemia patents, two subjects were found to exhibit a G-to-T transition at 1199 nucleotide sequence, which has not been reported. These two individuals are heterozygote for this single nucleotide variation. A higher number of patients who exhibit a G-to-A variation at the same 1199 nucleotide position were also noted. As shown in Table 6, the novel variant 1199T is found with a estimated frequency of 2.3% and the previously reported variant, 1199A is recorded at 9.1% frequency. The frequency of G1199A in these patients is about 2 fold higher than that reported in healthy Caucasians (ref), and 3 fold higher than the newly discovered G1199T variant Development and Characterization a Recombinant Cell Expression MDR1 and Variants Expression plasmid carrying MDR1 and its variants were constructed as described in Materials and Methods, and they were expressed in a common mammalian host, Human Embryonic Kidney (HEK) cells. The HEK host cells were chosen based on low or minimal levels of MDR1-like functions and high levels of recombinant protein expression. After selection of recombinant cells with high degree of expression, all the recombinant cells expressing MDR1 and 1199 variants were found able to transport Pgp probe substrate R123. As shown in Table 7, these recombinant cells exhibit varying ability to reduce intracellular accumulation of Pgp probe substrate R123.

These cells were expanded and tested initially for their ability to alter the cytotoxicity profile, presented as 50% inhibitory concentration or $EC_{50}$ of viblastine, a Pgp substrate. Stability of the Pgp expression over time was also monitored by retesting the $IC_{50}$ of different variants over a 2 month period, roughly 15-20 passages. As shown in Table 8, the recombinant cells expressing MDR1 and 1199 variants exhibit higher degree of resistance to vinblastine than the control HEK host cells. In addition, the degree of resistance were sustained over 2 month in culture suggesting the stable expression of the MDR1 gene product, Pgp.

Figure 9:
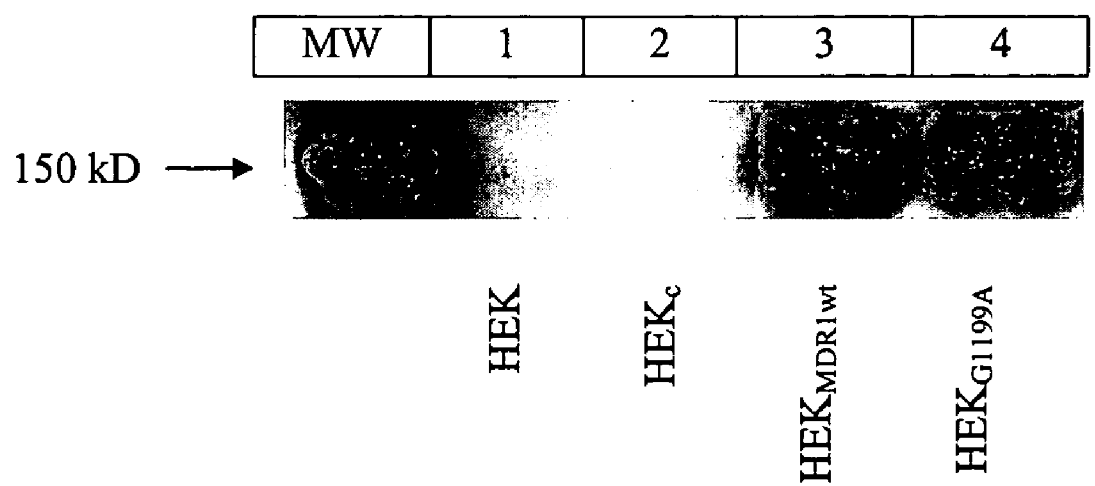
FIG. 9: Immunoblot analysis of MDR1 product, Pgp expression in recombinant HEK cells.
Figure 10:
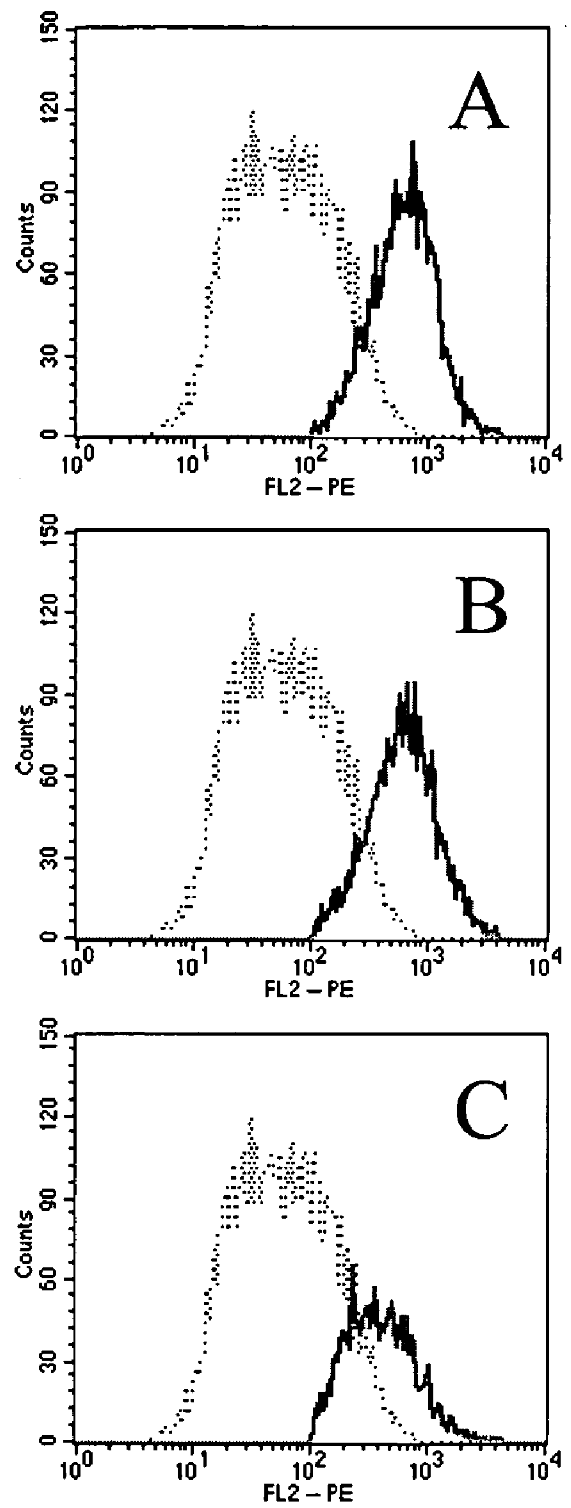
FIG. 10: Cell surface expression of Pgp in recombinant HEK cells expressing MDR1 and G1199 variants. Recombinant HEK cells expressing $MDR1_{wt}$ (Panel A), $MDR1_{G1199A}$ (Panel B), and $MDR1_{G1199T}$ (Panel C) or control plasmid were fluorescently stained with anti-MDR1 antibody (F4) as described in the Materials and Methods. The distribution of antibody positive cells with high fluorescence was analyzed by flow cytometry. Each panel was presented with cell-distribution profile for control cells (dotted lines) as a reference.

The protein product of MDR1, 1199A and 1199T variants expressed in these stable recombinant HEK cells were further characterized by immunoblot to detect the size of the protein and degree of expression. As shown in FIG. 9, the apparent molecular weight of $MDR1_{wt,}$ $MDR1_{1199A}$ and $MDR1_{1199T}$ gene products were similar and recorded to at approximately 170 kD. The recombinant cells were also analyzed by flow cytometery to characterized cell-surface expression of Pgp. As shown in FIG. 10, all the MDR1 expressing HEK recombinant cells exhibit similar degree of surface staining to anti-Pgp antibody suggesting that they express similar levels of surface Pgp, accessible to anti-Pgp antibody.

Collectively, these data suggest that the recombinant HEK cells expressing MDR1 and 1199 variants produced 170 kD product found on cell-surface with similar levels and their expression is stable in culture for at least two months. These cells were used subsequently for determination of variations in drug resistance.

Figure 11:
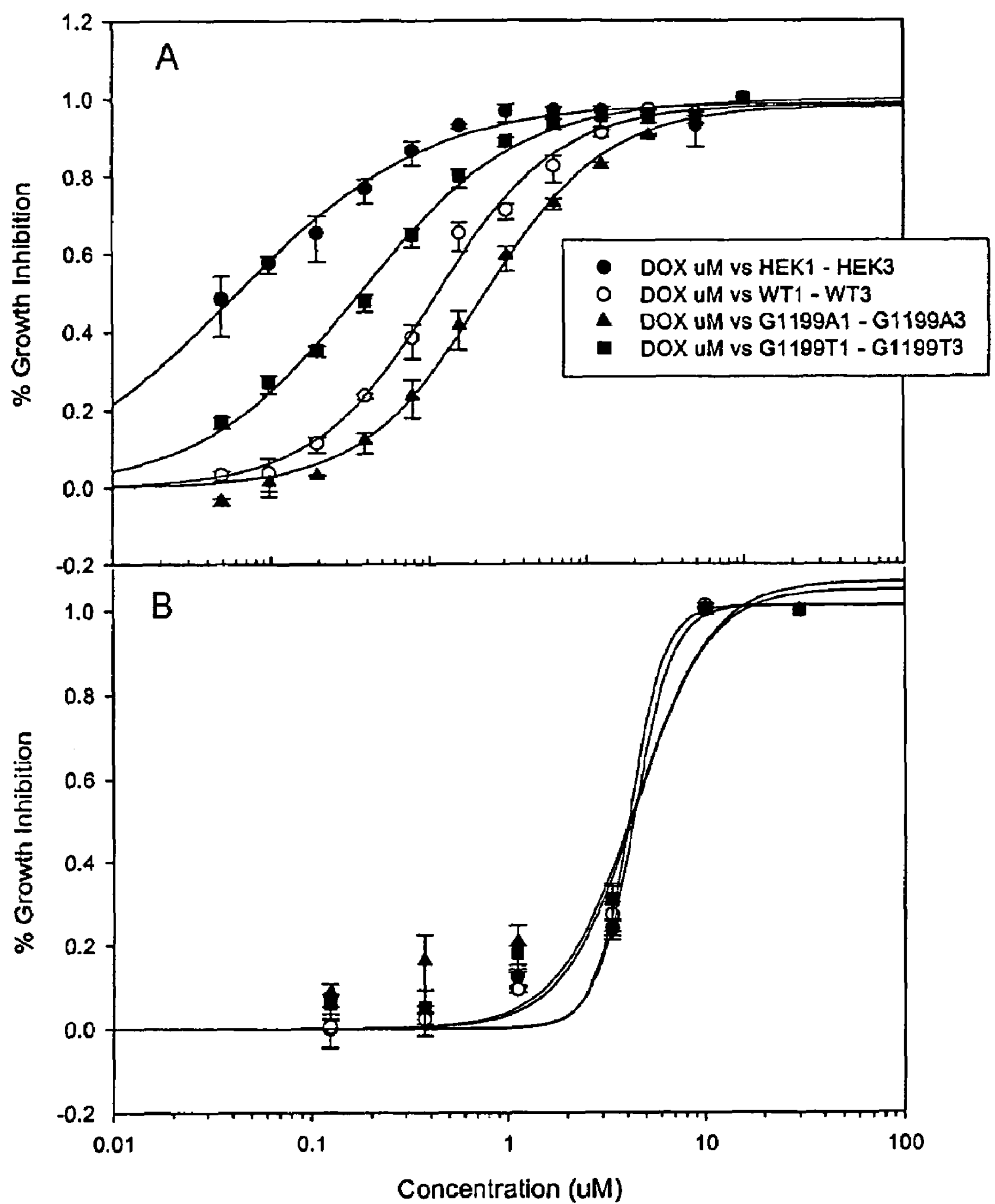
FIG. 11: Percent growth when incubated with varying concentrations of Doxorubicin (A) or Ivermectin (B) for 72 hours.

Evaluation of Functional Impact on G1199T Variant on MDR1-dependent Drug Resistance Previously with recombinant LLC-PK1 cell expressing MDR1 and variants, we have shown that G1199A coding for an Asn at 400 exhibits a functional variant on the transport of vinblastine and vincristine. Both of these drugs showed a significant impact in resistance as determined by variations in $EC_{50}$ values and transepithelial transport across monolayer. However, Doxorubicin had only a slightly higher transport rate in the G1199A. To determine whether G1199T exhibits similar or different intracellular efflux transport activity, a panel of drugs was used to generate dose-response profile of recombinant HEK cells expressing MDR1-wild type, G1199A or G1199T variants. A representative dose-response profile for MDR1 substrate doxorubicin and control substrate ivermectin are presented in FIG. 11. As shown in FIG. 11, expression of MDR1 exhibit right-shift or increasing concentration of doxorubicin needed to inhibit cell growth, and G1199A variant further enhance this effect. In contrast, G1199T variant appeared to reduce drug-resistance effect mediated by MDR1 expression. The MDR1 mediated effect was specific in that control drug substrate, ivermectin (which is a BCRP specific substrate) exhibit similar degree of sensitivity among all cells, including non-MDR1 expressing control cells.

Drug sensitivity profile generated for recombinant cells expressing Pgp and variants were summarized in Table 9 for the common chemotherapeutic agents, vinblastine, vincristine, doxorubicin, paclitaxel and ivermectin. With the exception of non-Pgp substrate, ivermectin, all chemotherapeutic agents exhibit lower sensitivity (higher EC50 value) for recombinant cells expressing MDR1. The cell expressing G1199A exhibit significantly higher degree of resistance to all but ivermectin than those expressing wt counter part. In contrast, the G1199T—newly discovered variant exhibit lower sensitivity than that or wt counter part. These results were replicated in at least three separate experiments to be reproducible with less than 10% error between experiments.

Collectively, dose response studies with a panel of chemotherapeutic agents indicate that the newly discovered G1199T variant is less effective in inducing drug resistance phenotype in recombinant cells expressing MDR1 product Pgp. In contrast, the previously reported G1199A variant of MDR1 produces higher resistance than the wt phenotype.

Differences in Intracellular Drug Substrate Concentrations Among MDR1 and 1199 Variants To determine whether the observed variable increase in drug resistance is due to reduction in intracellular concentrations of Pgp substrates, the time course profile of intracellular concentration of doxorubicin as a model substrate was evaluated. Over a 2 hr time course, a much lower intracellular concentrations of doxorubicin in cells expressing MDR1 was found. While the time to reach maximum intracellular concentrations was similar, the extent of drug accumulation in cells were significantly higher in control cells that lack MDR1, followed by those that express $MDR1_{1199T}$, $MDR1_{wt,}$ or $MDR1_{1199A.}$ Regardless of which MDR1 variant, reduction in intracellular doxorubicin concentration in recombinant cells expressing MDR1 can be reversed with a well-studied Pgp specific inhibitor, GF120918. Taken together, these data suggest that variation in drug resistance in recombinant cells expressing MDR1 and 1199 variants were likely due to alteration in effectiveness in reduction of intracellular drug concentrations.

Dicsussion

Capitalizing on the discovery of a genetic variant, G1199T of multidrug resistance protein MDR1 in patients with leukemia, and available stable recombinant cells for systematic evaluation, the functional impact of this single nucleotide polymorphism was characterized. While details mechanisms remained to be explored, probing of dose-response and intracellular concentration of model drug substrates indicates that G1199T variant is less effective in reducing intracellular drug concentrations and therefore, exhibit lower degree of drug resistance, compared to the $MDR_{wt}$. With $MDR1_{G1199T}$ about 2-3 fold in resistance is found consistently for the for Pgp substrates—oxorubicin, vincristine, vinblastine, and paclitaxel, compared to the $MDR1_{wt}$ (Table 8). In contrast, another variant $MDR1_{G1199A}$ polymorphism, exhibit higher degree of drug resistance than $MDR1_{wt}$ phenotype. Based on these data, it is likely that response rate of patients who are on chemotherapeutic agents that are Pgp substrates, such as paclitaxel, doxorubicin, vincritine, or vinblastine may be significantly different depending on which version of $MDR1_{1199}$ one expresses.

For the discovery of MDR1 variants, we have focused on analyzing the coding regions in leukemia patents to accelerate the identification of sequence variants that my produce amino acid change and more importantly function of the MDR1 proteins or Pgp. In a relatively small pool of AML subjects, we found the frequency of the G1199T variant to be 2.3%, which is about one-fourth frequency to that of G1199A (9.1%) in the same set of subjects. In our study subjects, we found the frequency of G1199A to be about two fold higher than larger population study in healthy volunteers (~5.5% in Caucasians). Whether the age of our AML patients may also contribute to a higher frequency of G1199A is not known and age dependent effects remained to be explored. In addition, whether there is any linkage with this G1199T variant with other genetic variation in the same chromosome—either in exon or intron region—exits is not clear, and warrant further evaluation of this gene which has been estimated to be large and characterized recently to be around 200 kb. Also, the frequency of G1199T in healthy human subjects is yet to be determined.

Regardless of the exact frequency of occurrence for this new single nucleotide variant in humans, it is interesting to note that G1199T have significantly altered the function of MDR1 product, Pgp efflux transporter. The G1199T variant, which gives rise to isoleucine instead of serine at 400 amino acid position, exhibited lower efficiency than the wild-type Pgp in efflux transport of a Pgp substrate doxorubicin. The reduced efficiency in efflux function is also reflected in lower degree of resistance to chemotherapeutic agents in recombinant cells expressing G1199T variant, instead of their wild-type counterpart (Table 8). These findings are contrary to the functional impact of another variant sequenced to identical position, G1199A. We found that G1199A variation, which give rise to aspargine, instead of serine at 400 amino acid position, exhibited higher degree of resistance than the parent Pgp protein to chemotherapeutic agents (Table 8). The drug resistance profile for G1199A is consistent with data collected using recombinant epithelial cells expressing MDR1 and variants. (See, e.g., Woodahl et al., *J. Pharmacol. Exp. Ther.* 310:1199-207, 2004) Nevertheless, it is interesting to note that different single nucleotide substitution at G1199 position of MDR1 produces either enhancement or reduction in Pgp.

While the detailed molecular mechanisms leading to reduction in drug resistance is not clear, the reduction and enhancement in effectiveness to remove Pgp substrate, doxorubicin in cell expressing G1199T and G 1199A variant suggest that 400aa position of Pgp is a critical determinant for efficiency of efflux transport activity of Pgp. Based on sequence analysis and protein topology prediction, the 400aa position is located proximity to nucleotide binding region. While it is possible, whether modification of amino acid from serine to either isoleucine (hydrophobic amino acid) or aspargine (basic amino acid) may have an impact on ATP hydrolysis rate and thereby modifying efficiency of transport is not clear, and this issue is under our current investigation. A more detailed molecular analysis will require purified proteins and obtaining crystallized proteins. The stable recombinant cell system over expressing high levels of MDR1 and variants at consistent levels, such as the one described in this report should accelerate this process.

TABLE 6

Allelic frequency of MDR1 1199 polymorphisms in Leukemia patients

| Sequence/ variation at 1199nt position | Amino Acid variation at 400 position | Estimated allelic Frequency in leukemia patients |
|---|---|---|
| Wild type | Ser | 0.886 |
| G → A | Asn | 0.091 |
| G → T | Ile | 0.023 |

The RNA from 44 leukemia patients were collected and the MDR1 RNA transcrips were reverse-transcribed into complementary DNA. These MDR1 DNA-products were sequenced and analyzed to assign the allele for each individual subject. These data were validated and presented as overall allelic frequencies.

TABLE 7

Intracellular levels of the Rhodamine123 inMDR1 expressed and control HEK cells[a]

| Cell | Intracellular Rhodamine (Unit/mg protein)[b] | % of control[c] |
|---|---|---|
| HEK293 | 4.66 ± 0.14 | 100 |
| $MDR1_{wt}$ | 2.26 ± 0.06 | 220 |
| $MDR1_{G1199A}$ | 1.44 ± 0.12 | 340 |
| $MDR1_{G1199T}$ | 1.82 ± 0.17 | 260 |

[a]HEK293 and MDR1 transfected cells were seeded into 12 well tissue culture plates at 5 × 105, and incubated at 37 C. for 48 hours. Medium was removed and the cells were washed briefly with 2 ml HBSS. One milliliter of serum-free medium containing 0.5 uM Rhodamine123 was added into each well for 30 minutes at 37 C. Medium containingRhodamine was quickly removed, and the plates were washed twice with DPBSG. One milliliter of medium was added to each well and efflux was performed at 37 C. for 30 minute. After extensive washing of the cells with 5 ml DPBSG for 2 times at 4 C., cells were lysed with 1% Triton X-100. The intracellular Rhodamine 123 fluorescence ($\lambda_{ex}$ = 485 nm; $\lambda_{em}$ = 530 nm) was determined and expressed as arbitrary units.
[b]The mean value of Rhodamine fluorescence unit from each well was normalized by total cellular protein contents.
[c]Value was converted to the HEK293 cells

TABLE 8

Stability/reproducibility of EC50 over time for cell growth inhibition by Vincristine. nM ± s.d.

| Time since first assessment | HEK negative control | HEK - MDR1 WT | HEK - MDR1 G1199A | HEK - MDR1 G1199T |
|---|---|---|---|---|
| 0 month | 4.01 ± 1.29 | 494 ± 115 | 683 ± 276 | 246 ± 84 |
| 1 months | 6.68 ± 0.448 | 512 ± 85.1 | 667 ± 87.5 | |
| 2 months | 10.15 ± 1.04 | 710 ± 33.3 | 860 ± 51.8 | |

Cells were seeded at 1 × $10^4$ cells per well on Day −1 in a 96 well plate. Vincristine was added at varying concentrations on Day 0. After 72 hours, the MTS assay was performed on HEK, WT, and G1199A cells. An EC50 value was calculated ± s.d. This was repeated over 1 and 2 months.

TABLE 9

Effects of MDR1 wild-type and G1199 variant expression on sensitivity of HEK cells to chemotherapeutic agents.

| Drug | $EC_{50}$ (Mean ± S.D. in nM) | | | |
|---|---|---|---|---|
| | HEK Control | WT | G1199A | G1199T |
| Vinblastine | 1.45 ± 0.23 | 127 ± 13.0 | 243 ± 15.1*** | 54.7 ± 7.99** |
| Vincristine | 10.2 ± 1.04 | 710 ± 33.3 | 860 ± 51.8* | 246 ± 84.3** |
| Doxorubicin | 45.5 ± 25.1 | 1107 ± 112 | 2179 ± 361* | 383 ± 39.0** |
| Paclitaxel | 2.67 ± 0.13 | 128 ± 50 | ± | 42.7 ± 12.7 |
| Ivermectin | 4101 ± 210 | 3809 ± 27.3 | 4038 ± 77.6 | 3837 ± 306.7 |

The MDR1 wild-type, G1199A or G1199T variants, along with MDR1 negative control HEK host cells were seeded at $1 \times 10^4$ cells per well in a 96 well plate. They were exposed to varying concentration of vincristine, vinblastine, doxorubicin, paclitaxal or ivermectin for 72hours and cell viability was determined with an MTS assay. The dose-responsecurve was fitted as described in Materials and Methods to estimate $EC_{50}$ values. The variations of each fitted value for the quadruplicated samples were expressed as standard deviation (± S.D.). The differences between each treatment group were analyzed with 2-sided t-test compared to WT, and presented as follows:
*$p < 0.05$,
**$p < 0.005$,
***$p < 0.001$

EXAMPLE 3

Impact of MDR1 G1199A Polymorphism on Absorption of HIV Protease Inhibitors Across Epithelial Cells The standard of care for HIV therapy, known as highly active antiretroviral therapy (HAART), utilizes a combination of drugs that attack the virus through different mechanisms of action. HAART combines the use of reverse transcriptase (RT) inhibitors, either nucleoside or nonnucleoside analogues and protease inhibitors, each targeting different mechanisms of the life cycle of HIV. The RT inhibitors, such as AZT, ddC, ddI, d4T, and 3TC, interfere with the reverse transcription of viral RNA. Protease inhibitors, such as amprenavir, indinavir, lopinavir, nelfinavir, ritonavir, and saquinavir, block the HIV protease cleavage of precursor proteins into unites necessary for construction of new mature virions. Clinically, oral HAART decreases plasma viral load to undetectable levels over long-term chronic therapy, indicating it is effective in controlling viral replication (see Hammer et al., *N. Engl. J Med.* 337:725-733 (1997); Vittinghoff et al., *J. Infect. Dis.* 179:717-720 (1999); Palella et al., *N. Engl. J. Med.* 338:853-60 (1998)).

While HAART is effective in containing plasma viral loads, eventual HIV disease progresses to AIDS occurs even in individuals receiving intensive antiretroviral therapy. It is widely believed that viral sanctuary sites, impermeable to drug therapy, exist in the body that ultimately lead to the viral progression. Potential viral sanctuary sites that have been proposed include lymph lodes and lymphoid tissues and the central nervous system (Kinman et al., *J. Acquir. Immune Defic. Syndr.* 34:387-97 (2003); Kinman et al., *AIDS* 18:1363-70 (2004); Cavert et al., *Science* 276:960-4 (1997); Schacker et al., *J. Infect. Dis.* 181:354-7 (2000)).

P-gp, the gene product of MDR1, has been shown to mediate the transport of HIV protease inhibitors in both in vitro and in vivo models (Kim et al., *Clin. Pharmacol. Ther.* 70:189-199 (2003); Lee et al., *Biochemistry* 37(11):3594-601 (1998); Srinivas et al., *Antimicrob. Agents Chemother.* 42:3157-3162 (1998); Williams et al., *J. Pharm. Sci.* 92:1957-67 (2003); Washington et al., *J. Acquir. Immune Defic. Syndr. Hum. Retrovirol.* 19:203-9 (1998)). The oral bioavailability of HIV protease inhibitors in systemic circulation is variable: amprenavir 35-90%, indinavir 70%, nelfinavir 70-80%, ritonavir 60-80%, and saquinavir 4% (van Heeswijk et al., *Antivir. Ther.* 6(4):201-29 (2001)). In addition to the contribution of cytochrome P450 metabolism, the highly efficient active efflux by P-gp of HIV protease inhibitors in the intestine has been proposed to play a major role in limiting their oral bioavailability.

Furthermore, expression of P-gp may play a role in limiting penetration and accumulation of sufficient concentrations of HIV protease inhibitors into viral sanctuary sites. P-gp expression and activity has also been documented in various subtypes of lymphocytes (Laupeze et al., *Hum. Immunol.* 62(10:1073-80 (2001); Meaden et al., *J. Immunol. Methods* 262(1-2): 159-65 (2002); Parasrampuria et al., *Pharm. Res.* 18(1):39-44 (2001)) as well as in endothelial cells at the blood-brain-barrier. The P-gp dependent efflux of HIV protease inhibitors decreases intracellular drug accumulation in lymphocytes (Donahue et al., *Clin. Pharmacol. Ther.* 73(1): 78-86 (2003); Hennessy, *Antivir. Ther.* 9(1):115-22 (2004); Jones, *AIDS* 15(11):1353-8 (2001)). P-gp at barrier limits brain permeability of protease inhibitors (van der Sandt, *AIDS* 15(4):483-91 (2001)). Therefore, P-gp limits HIV protease inhibitor levels in HIV sanctuary sites and may further reduce the effectiveness of antiretroviral therapy in these tissues.

Researchers have evaluated the effect of P-gp expression on HIV disease progression and protease inhibitor drug levels. In HIV patients, data suggests that expression of functionally defective P-gp increases with disease progression (see Andreana et al., *AIDS Res. Hum. Retroviruses* 12:1457-1462 (1996). Overexpression of MDR1 in HIV positive was shown to correlate to decreased systemic trough concentrations nelfinavir, indinavir, amprenavir, ritonavir, and saquinavir as well as decreased accumulation in lymphocytes (see Chaillou et al., *HIV Clin. Trials* 3:493-501 (2002)). Studies have also shown that saquinavir, ritonavir, nelfinavir, indinavir, amprenavir and lopinavir induce the expression of P-gp in human lymphocytes, which could act to further decrease intracellular accumulation of protease inhibitors (see Ford et al., *J. Antimicrob. Chemother.* 52:354-358 (2003); Dupuis et al., *HIV Med.* 4:338-345 (2003)).

Genetic polymorphisms are now known to play a role in P-gp expression and function. In addition, MDR1 polymorphisms, particularly the C→T transition at nucleotide 3435, have been correlated to HIV protease inhibitor levels and response to antiretroviral drug therapy. Homozygous 3435T patients receiving nelfinavir therapy had lower plasma nelfinavir concentrations homozygous 3435C patients Fellay et al., *Lancet:* 359:30-6 (2002)). In addition, 3435T patients had a significantly greater rise in CD4+cell counts and a trend towards lower viral loads than 3435C patients (Fellay et al., supra). Other researchers have also found a strong trend associated with homozygous 3435T patients more effectively responding to protease inhibitor therapy (see Brumme et al., *AIDS* 17:201-208 (2003); Nasi et al., *AIDS* 17:1696-1698 (2003)). However, it is difficult to determine whether the C3435T polymorphism acts directly at the cellular and molecular level because this polymorphism does not code for an amino acid modification. Therefore, it is important to have a tool with which to probe the penetration and uptake of protease inhibitors at the cellular level. To accomplish this, the influence of MDR1 polymorphisms that lead to an amino acid modification must be evaluated by functional studies at the cellular and molecular levels. Toward this end, a recombinant cell expression system expressing MDR1 G1199A has been developed and G1199A expression has been demonstrated to alter anticancer drug resistance and permeability (Woodahl et al., *J. Pharmacol. Exp. Ther.* 310(3):1199-207 (2004)).

Using these recombinant cells, the next objective in elucidating the role of G1199A was to evaluate whether G1199A will also have an influence on the transport and permeability of HIV protease inhibitors. Altered permeability of HIV protease inhibitors across an epithelial barrier due to MDR1 polymorphisms may affect absorption of protease inhibitors from the intestine as well as their penetration into potential HIV sanctuary sites such as lymphoid tissues and the central nervous system (CNS). METHODS Cell Culture LLC-PK1 control and transfected cells were grown in complete media consisting of RPM1 medium 1640 (Invitrogen, Carlsbad, Calif.) supplemented with 10% (v/v) fetal calf serum and 1 % (v/v) antibiotic-antimycotic and grown at 37° C. in the presence of 5% $CO_2$. For deconvolution immunofluorescent microscopy and transepithelial transport studies, cells were grown in Medium 199 (Invitrogen) supplemented with L-glutamine, 10% (v/v) fetal calf serum, and 1% (v/v) antibiotic-antimycotic and grown at 37° C. in the presence of 5% $CO_2$.

Transepithelia Transport Assay

LLC-PK1 control and recombinant MDR1 cells were plated at a density of $2\times10^6$ cells/24 mm well on permeable supports (Transwell™; 3.0 μm membrane pore size; Corning) and grown for 4 days; media was refreshed after two days in culture. Fresh media was added to the cells one hour before the initiation of the experiment, and transepithelial electrical resistance (TEER) values were measured with a Millicell®-ERS (Millipore, Billerica, Mass.). Transepithelial efflux with radiolabeled compounds $^3$H-amprenavir, $^3$H-lopinavir, $^3$H-ritonavir, and $^3$H-saquinavir (Moravek) were performed at concentrations of 5 μM (1 μCi per well) in Opti-MEM medium (Invitrogen). Efflux of indinavir was also performed at 5 μM and aliquots were diluted 1:1 in methanol for analysis with liquid-chromatography coupled mass-spectroscopy (LC/MS) using an Agilent 1100 LC-MSD fitted with an RX-C8 column (2.1 mm×15 cm; Zorbax, Agilent Technologies, Palo Alto, Calif.). A 10 μL sample was injected onto the column and eluted isocratically at a flow rate of 0.25 mL/min with a mobile phase containing acetonitrile/20 mM acetic acid (65:35, vol/vol). The mass spectroscopy was operated in atmospheric pressure ionization-electrospray ionization (API-ESI$^+$) mode, and the analytes were detected using selected-ion monitoring at m/z 614.7-615.7 days to detect indinavir. Inhibition of transport was performed at 1 μM GF120918. Aliquots of 50 μL were taken from apical and basal compartments at 1, 2, 3, and 4 hours for each drug. Percent transport in both directions, apical-to-basolateral and basolateral-to-apical, was calculated at each time point as the amount of drug in the recipient compartment divided by the initial amount in the donor compartment. Apparent permeability ($P_{app}$) was calculated in the apical-to-basolateral direction ($P_{app\ A\rightarrow B}$) and in the basolateral-to-apical direction ($P_{app\ B\rightarrow A}$) as described (Polli et al., *J. Pharmacol. Exp. Ther.* 299:620-8 (2001)). Briefly, $P_{app}$=(1/(A*$C_0$))*(dQ/dt), where A is the surface area of permeable support, $C_0$ is the initial concentration in the donor compartment, and dQ/dt is the rate of transfer of compound into the acceptor compartment. The ratio of $P_{appB\rightarrow A}/P_{appA\rightarrow B}$ was also estimated to evaluate P-gp-mediated directional efflux.

Results

Directional Transepithelia Transport

Evaluating transport of compounds across an epithelial cell barrier provides the ability to predict how drug will move across physiologic cell barriers in the body, including the intestine, kidney, and blood-brain-barrier. For a physiologic comparison, in intestinal epithelial cells, the apical compartment represents the intestine lumen; in kidney epithelial cells, the apical compartment represents the kidney proximal tubules; and in brain endothelial cells, the apical compartment represents blood adjacent to the blood-brain-barrier. In contrast, in intestinal and kidney epithelial cells the basolateral compartments represents the blood and in the brain endothelial cells the basolateral compartment represents the brain. Drugs administered orally will encounter the apical membrane of intestinal epithelial cells and will have to cross this cellular barrier before entering systemic circulation. Intravenously administered drugs will encounter the basolateral membrane leading to their excretion and elimination.

Figure 12:
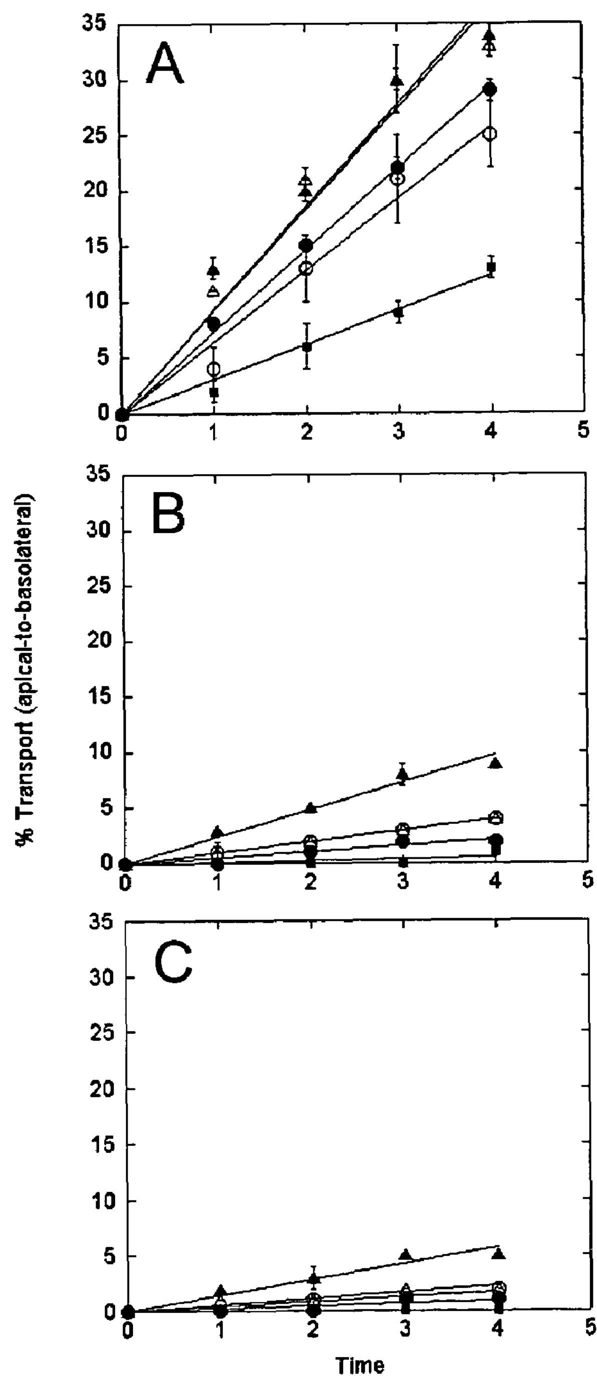
FIG. 12: Apical-to-basolateral efflux transport of HI protease inhibitors in the absence of GF120918. Transepithelial permeability was evaluated as the percent transport of protease inhibitors across an epithelial monolayer; LLC-PK1 control cells (panel A); $MDR1_{wt}$ cells (panel B); and $MDR1_{1199}$ cells (panel C). Transport of amprenavir (▲), indinavir (•), lopinavir (Δ), ritonavir (○), and saquinavir (■).

The transfer of amprenavir, indinavir, lopinavir, ritonavir, and saquinavir over time across an epithelial cell barrier was measured with the drugs alone (apical-to-basolateral: FIG. 12; basolateral-to-apical FIG. 13) and with the specific inhibitor GF120918 (apical-to-basolateral: FIG. 14; basolateral-to-apical FIG. 15). Drug was placed in either the apical or basolateral compartment and percent transport (amount of drug in recipient compartment/initial amount in donor compartment) was estimated for each time point.

Apical-to-basolateral efflux, in the absence of GF120918, was greatly reduced by the expression of either $MDR1_{wt}$ or $MDR1_{1199}$ compared to control cells, indicating expression of functional P-gp (FIG. 12). In control cells, movement of drug across a cell membrane is assumed to be mediated primarily by diffusion; however, all protease inhibitors did not cross the epithelial membrane at the same rate in the apical-to-basolateral direction indicating rates of transfer may be a function of physiochemical properties of protease inhibitors. The rank order of transfer (dQ/dt, presented in Table 10) in control cells was amprenavir=lopinavir>indinavir=ritonavir>saquinavir (a significant difference of dQ/dt between protease inhibitors was defined as $p<0.05$). The rank order of dQ/dt of protease inhibitors was similar between $MDR1_{wt}$ (amprenavir>lopinavir=ritonavir>indinavir>saquinavir; $p<0.05$) and $MDR1_{1199}$ cells (amprenavir>lopinavir>ritonavir>indinavir>saquinavir; $p<0.05$); and corresponded to the control cells.

Figure 13:
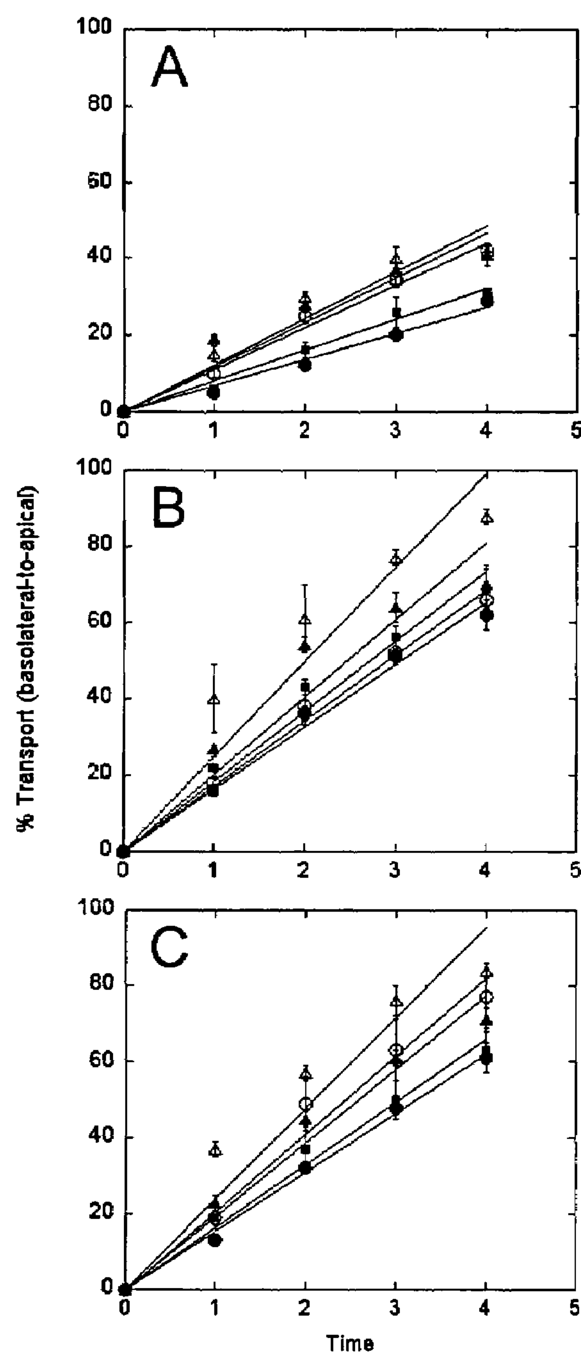
FIG. 13: Basolateral-to-apical efflux transport of HIV protease inhibitors in the absence of GF120918. Transepithelial permeability was evaluated as the percent transport of protease inhibitors across an epithelial monolayer; LLC-PK1 control cells (panel A); $MDR1_{wt}$ cells (panel B); and $MDR1_{1199}$ cells (panel C). Transport of amprenavir (▲), indinavir (●), lopinavir (Δ), ritonavir (○), and saquinavir (■).

Next, basolateral-to-apical efflux was evaluated in the three cell types (FIG. 13). Expression of either $MDR1_{wt}$ or $MDR1_{1199}$ enhanced basolateral-to-apical flux compared to control cells, confirming expression of P-gp. Again, diffusion in the control cells was not equal across the protease inhibitors with the rank order as lopinavir=amprenavir=ritonavir>saquinavir>indinavir ($p<0.05$). The rank order of dQ/dt in $MDR1_{wt}$ (lopinavir>ritonavir=amprenavir=saquinavir=indinavir; $p<0.05$) and $MDR1_{1199}$ (lopinavir>ritonavir=amprenavir>saquinavir=indinavir; $p<0.05$) also corresponded to the control cells Differences in the activity of P-gp between cells expressing $MDR1_{wt}$ or $MDR1_{1199}$ were observed for all five protease inhibitors. The transepithelial data was evaluated in the individual directions (Table 10). A highly significant decrease in apical-to-basolateral flux in $MDR1_{1199}$ cells was observed for all protease inhibitors compared to $MDR1_{wt}$ cells [amprenavir: 1.7-fold ($p<0.0001$); indinavir: 1.9-fold ($p<0.001$); lopinavir: 1.6-fold ($p<0.0001$); ritonavir: 2.3-fold ($p<0.0001$); and saquinavir 2.3-fold ($p<0.0001$)]. These data indicate that P-gp expressed in $MDR1_{wt}$ cells was less efficient at limiting absorption across the epithelial barrier compared to $MDR1_{1199}$ cells. However, no differences were observed between $MDR1_{wt}$ and $MDR1_{1199}$ cells in the basolateral-to-apical direction, with the exception of a modest increase in efflux of ritonavir (1.2-fold; $p<0.05$) in $MDR1_{1199}$ cells compared to $MDR1_{wt}$. Therefore, while a significant amount of drug was secreted across the epithelial cells in the basolateral-to-apical direction in both MDR1 cells, there appears to be no G1199A genotypic differences. And such a significant amount of drug crossed the cell barrier, especially apparent in the case of lopinavir, that the rate of transfer appeared to diminish over time in both cells (FIG. 13); therefore, the system may not have been under sink conditions at the later time points. Therefore, the data suggests that while both $MDR1_{wt}$ and $MDR1_{1199}$ recombinant cells display efficient apical-to-basolateral and basolateral-to-apical efflux of protease inhibitors, the influence of the G1199A polymorphism may have the largest impact on the absorptive apical-to-basolateral direction.

The specific P-gp inhibitor, GF120918, was used in the apical-to-basolateral (FIG. 14) and basolateral-to-apical (FIG. 15) directions to confirm the efflux of protease inhibitors was mediated by P-gp. GF120918 had little effect on the control cells in either direction. Inhibition with GF120918 effectively blocked P-gp activity in both $MDR1_{wt}$ and $MDR1_{1199}$ cells; therefore, enhancing apical-to-basolateral efflux and decreasing basolateral-to-apical efflux for all protease inhibitors. This confirms that the efflux of protease inhibitors in these cells is a P-gp specific effect. In the presence of GF120918, G1199A genotypic differences in apical-to basolateral efflux were eliminated for all protease inhibitors except for indinavir; and a genotypic difference was also observed in the basolateral-to-apical direction for indinavir. Therefore, other transporters besides P-gp may play a role in the efflux of indinavir across an epithelial membrane.

Collectively, these data indicate that P-gp is the primary contributor of protease inhibitor efflux across the recombinant cells system that has been developed. Significant differences in P-gp efflux between $MDR1_{wt}$ and $MDR1_{1199}$ cells were observed for all protease inhibitors in the apical-to-basolateral direction but negligible genotypic differences exist in efflux in the basolateral-to-apical direction. G1199A expression had the largest impact on the apical-to-basolateral efflux of ritonavir and saquinavir, followed by indinavir, then amprenavir, and then lopinavir. This highly significant decrease in apical-to-basolateral efflux in $MDR1_{1199}$ cells was abolished in the presence of GF120918 indicating that the observed G1199A effect was mediated by P-gp.

Apparent Pereability Ratios Across Epithelial Cells

After evaluating P-gp efflux in the individual directions, the next step was to estimate permeability ratios ($P_{appB\rightarrow A}/P_{appA\rightarrow B}$) that represent the net flow of drug across an epithelial membrane. The ratios were calculated for comparison between $MDR1_{wt}$ and $MDR1_{1199}$ cells (Table 11). If cells display directional efflux mediated by P-gp, a permeability ratio greater than 1.0 is expected, and in the presence of a P-gp-specific inhibitor, GF120918, the ratio should be reduced to about unity. As shown in Table 11, both $MDR1_{wt}$ and $MDR1_{1199}$ cells exhibit increased permeability ratios compared to control cells for all protease inhibitors, indicating that P-gp enhanced drug efflux. Cells expressing $MDR1_{1199}$ have significantly increased permeability ratios of all protease inhibitors compared to $MDR1_{wt}$ [amprenavir: 1.7-fold ($p<0.0005$); indinavir: 1.8-fold ($p<0.05$); lopinavir: 1.5-fold ($p<0.0005$); ritonavir: 2.8-fold ($p<0.0005$); and saquinavir 2.1-fold ($p<0.0005$)]. The rank order of permeability was saquinavir>indinavir>lopinavir >ritonavir>amprenavir in $MDR1_{wt}$ cells. The rank order in $MDR1_{1199}$ cells was saquinavir>indinavir>ritonavir>lopinavir>amprenavir. The permeability ratios of saquinavir in both MDR1 cells types were substantially higher than the ratios for other protease inhibitors, indicating that saquinavir is very efficiently effluxed by P-gp. In the presence of GF120918, permeability ratios were dramatically reduced in both $MDR1_{wt}$ and $MDR1_{1199}$ cells, confirmed that efflux was mediated by P-gp. While the permeability ratios are not reduced down to that of the control cells in the presence of GF120918, the numbers are similar between $MDR1_{wt}$ and $MDR1_{1199}$.

DISCUSSION

The recombinant cell expression system is a highly reliable and consistent method with which to evaluate functional changes in P-gp due to MDR1 genetic variation. Using this system, expression of G1199A was shown to result in variable cellular sensitivity and permeability of anti-cancer agents. This system has been extended to study the influence of G1199A in transepithelial permeability of HIV protease inhibitors. The ability of HIV protease inhibitors to cross a cellular barrier is important not only in appreciating their absorption from the intestine but also their penetration into potential HIV sanctuary sites such as lymphoid tissues and the CNS.

The apical-to-basolateral data indicate that MDR1 expression, and therefore P-gp efflux, dramatically reduces absorption of protease inhibitors from the apical to the basolateral compartment, analogous to the effect P-gp has in limiting absorption of protease inhibitors from the intestine after oral administration. The same effect would also be observed at the blood-brain-barrier, limiting brain penetration, where drug is presented to the apical membrane of polarized cells. The basolateral-to-apical data, which represents the contribution of P-gp to systemic clearance where drug is presented to the basolateral cell membrane (i.e. after absorption of orally administered drug or after intravenous administration), shows that MDR1 expression enhances efflux of protease inhibitors to the apical compartment for excretion and elimination.

The rank orders of protease inhibitor transfer in the apical-to-basolateral and basolateral-to-apical directions did not correspond; however the ranks in each direction were similar between the three cell types. This indicates that different membrane components may exist in the apical or basolateral membranes of the polarized cells that aid in passive diffusion. The observed rank orders in the recombinant cell system correspond to previously reported studies. Apparent permeability ratios estimated in MDR1-MDCKII cells was the largest for saquinavir followed by ritonavir and then amprenavir, consistent with the permeability ratios in this study (Polli et al., *J. Pharmacol. Exp. Ther.* 299:620-8 (2001)). Directional transport in MDR1-MDCKII and Caco-2 cells also found that saquinavir had lower apical-to-basolateral transport than ritonavir and that the apparent permeability of saquinavir was greater than ritonavir (Troutman, *Pharm. Res.* 20:1210-24 (2003)). Permeability of saquinavir and indinavir in Caco-2 cells observed that apical-to-basolateral permeability was less for saquinavir than indinavir and that the apparent permeability ratio was greater for saquinavir than indinavir (Balimane, *Eur. J. Pharm. Biopharm.* 58:99-105 (2004)). Therefore, the LLC-PK1 recombinant expression cell system appears to display similar transport characteristics of HIV protease inhibitors as other in vitro cell systems.

Obvious differences in P-gp mediated efflux of protease inhibitors were observed between $MDR1_{wt}$ and $MDR1_{1199}$ cells. Bi-directional permeability ratios were statistically significant for all five protease inhibitors, demonstrating that $MDR1_{1199}$-expressing cells were more efficient at limiting the ability of amprenavir, indinavir, lopinavir, ritonavir, and saquinavir to cross an epithelial membrane. However, this type of net flow analysis with bi-directional permeability ratios makes it difficult to distinguish the exact mechanism by which the G1199A polymorphism alters P-gp activity. Therefore, to further characterize the influence of G1199A on P-gp activity, the effect of G1199A was evaluated independently on either absorptive processes (apical-to-basolateral) or secretory processes (basolateral-to-apical). According to analysis of the rates of transfer of protease inhibitors, the observed changes in permeability ratios were due primarily to changes in apical-to-basolateral efflux between $MDR1_{wt}$ and $MDR1_{1199}$ cells. All drugs displayed decreased apical-to-basolateral efflux in $MDR1_{1199}$ cells compared to $MDR1_{wt}$ cells, with the greatest effect observed in efflux of ritonavir and saquinavir, followed by indinavir, amprenavir, and lopinavir. The basolateral-to-apical efflux of protease inhibitors was similar between $MDR1_{wt}$ and $MDR1_{1199}$ cells, with the exception of a modest increase in basolateral-to-apical efflux of ritonavir in $MDR1_{1199}$ cells. Therefore, the effect of the G1199A polymorphism appears to be most significant when drug is exposed to the apical membrane of epithelial cells (i.e., absorption and penetration of the blood-brain-barrier) than when it is exposed to the basolateral membrane (i.e., secretion and elimination by kidney and liver).

The P-gp mediated efflux of protease inhibitors observed in both directions in $MDR1_{wt}$ and $MDR1_{1199}$ cells was almost completely inhibited in the presence of GF120918 near that of the efflux of control cells. As mentioned earlier, complete inhibition was not observed in the case of indinavir, which suggests that other transporters may be involved in the transepithelial efflux of indinavir. These data indicate that the differential transepithelial efflux of protease inhibitors due to G1199A expression observed in the recombinant cell system was mediated by P-gp.

In this chapter, the stable recombinant expression system has been used to further characterize the influence of G1199A on P-gp activity. The mechanisms by which G1199A alters P-gp activity are not yet known. The G1199A polymorphism causes a serine to asparagine change at amino acid 400, which lies adjacent to the first ATP-binding domain of P-gp and to transmembrane domain 6, one of the transmembrane domains important in substrate binding (REF). However, since a crystal structure is not yet available for P-gp, it is difficult to speculate on the three-dimensional structure of P-gp and where amino acid 400 lies in relation to the substrate-binding regions or ATP-binding domain of P-gp. Therefore, the G1199A polymorphism may affect ATPase activity of P-gp, altering ATP hydrolysis necessary for substrate efflux. Since the impact of G1199A was not equal across the protease inhibitors evaluated, expression of G1199A may also directly affect P-gp drug binding, affinity, or transport. Multiple binding sites of P-gp have been proposed so it is probable that amino acid modification, due to MDR1 polymorphisms, may differentially alter efflux of P-gp substrates (REF).

In summary, the transepithelial efflux and permeability of amprenavir, indinavir, lopinavir, ritonavir, and saquinavir has been evaluated in the stable recombinant cell system, and these drugs have been shown to be excellent substrates of P-gp. Expression of MDR1 in LLC-PK1 cells enhances both apical-to-basolateral and basolateral-to-apical efflux of protease inhibitors, and this effect can be reversed with the specific P-gp inhibitor GF120918. A significant impact of the G1199A polymorphism of efflux and permeability, although the magnitude of a G1199A effect is drug specific and the influence appears to have a more dramatic effect in the apical-to-basolateral direction, was also observed. Therefore, the G1199A polymorphism may impact intestinal absorption of protease inhibitors and penetration into cells and tissues of the lymphoid and central nervous systems.

TABLE 10

Rates of Transfer from Donor to Recipient Compartments (dQ/dt ± s.d.) for HIV Protease Inhibitors in LLC-PK1 Control and Recombinant MDR1 Cells

| | Protease Inhibitor Alone | | Protease Inhibitor + GF120918 | |
|---|---|---|---|---|
| | A → B | B → A | A → B | B → A |
| | Control | | | |
| amprenavir | 9.33 ± 0.46 | 11.6 ± 0.8 | 10.8 ± 0.9 | 10.2 ± 0.4 |
| indinavir | 7.17 ± 0.03 | 6.69 ± 0.21 | 4.26 ± 0.25 | 5.99 ± 0.11 |
| lopinavir | 9.21 ± 0.24 | 12.1 ± 0.7 | 8.48 ± 0.16 | 10.2 ± 0.4 |

TABLE 10-continued

Rates of Transfer from Donor to Recipient Compartments (dQ/dt ± s.d.) for HIV Protease Inhibitors in LLC-PK1 Control and Recombinant MDR1 Cells

| | Protease Inhibitor Alone | | Protease Inhibitor + GF120918 | |
|---|---|---|---|---|
| | A → B | B → A | A → B | B → A |
| ritonavir | 6.46 ± 0.94 | 11.0 ± 0.5 | 6.46 ± 0.69 | 9.60 ± 0.75 |
| saquinavir | 3.02 ± 0.35 | 8.03 ± 0.51 | 3.48 ± 0.57 | 7.36 ± 0.60 |
| | | $MDR1_{wt}$ | | |
| amprenavir | 2.39 ± 0.14 | 20.3 ± 1.0 | 9.90 ± 0.74 | 10.3 ± 0.5 |
| indinavir | 0.515 ± 0.038 | 17.0 ± 0.8 | 2.33 ± 0.09 | 6.91 ± 0.23 |
| lopinavir | 0.968 ± 0.057 | 24.9 ± 1.1 | 7.71 ± 0.35 | 11.1 ± 0.5 |
| ritonavir | 1.04 ± 0.05 | 17.2 ± 0.7 | 3.84 ± 0.28 | 13.6 ± 0.4 |
| saquinavir | 0.124 ± 0.013 | 18.5 ± 1.3 | 2.03 ± 0.25 | 13.0 ± 1.3 |
| | | $MDR1_{1199}$ | | |
| amprenavir | 1.39 ± 0.11*** | 19.4 ± 0.7 | 8.52 ± 1.26 | 9.35 ± 0.68 |
| indinavir | 0.279 ± 0.068** | 15.5 ± 0.8 | 1.65 ± 0.25* | 4.28 ± 0.04*** |
| lopinavir | 0.617 ± 0.020*** | 23.8 ± 0.8 | 6.89 ± 0.69 | 10.3 ± 0.5 |
| ritonavir | 0.451 ± 0.016*** | 20.5 ± 2.1* | 3.68 ± 0.49 | 12.9 ± 0.7 |
| saquinavir | 0.054 ± 0.003*** | 16.5 ± 1.6 | 1.88 ± 0.26 | 10.7 ± 1.1 |

[a]Significant difference between $MDR1_{1199}$ and $MDR1_{wt}$ cells;
*p < 0.05,
**p < 0.001, and
***p < 0.0001.

TABLE 11

Apparent Permeability Ratios for HIV Protease Inhibitors in LLC-PK1 Control and Recombinant MDR1 Cells

| | $P_{APPB \to A}/P_{APPA \to B}$ | | |
|---|---|---|---|
| LLC-PK1 CELLS | CONTROL | $MDR1_{WT}$ | $MDR1_{1199}$ |
| AMPRENAVIR | 1.24 ± 0.10 | 8.48 ± 0.65 | 14.0 ± 1.2*** |
| AMPRENAVIR + | 0.94 ± 0.08 | 1.04 ± 0.09 | 1.10 ± 0.18 |
| INDINAVIR | 0.93 ± 0.03 | 31.6 ± 2.6 | 55.4 ± 13.8* |
| INDINAVIR + GF120918 | 1.41 ± 0.09 | 2.96 ± 0.15 | 2.59 ± 0.39 |
| LOPINAVIR | 1.31 ± 0.08 | 25.7 ± 1.9 | 38.6 ± 1.9*** |
| LOPINAVIR + GF120918 | 1.21 ± 0.05 | 1.44 ± 0.09 | 1.49 ± 0.16 |
| RITONAVIR | 1.70 ± 0.26 | 16.6 ± 1.1 | 45.4 ± 4.9*** |
| RITONAVIR + GF120918 | 1.49 ± 0.20 | 3.54 ± 0.28 | 3.50 ± 0.50 |
| SAQUINAVIR | 2.66 ± 0.35 | 149 ± 19 | 306 ± 35*** |
| SAQUINAVIR + | 2.11 ± 0.39 | 6.40 ± 1.03 | 5.72 ± 0.86 |

[a]Significant difference between $MDR1_{1199}$ and $MDR1_{wt}$ cells;
*p < 0.05,
**p < 0.005, and
***p < 0.0005.

TABLE 12

Summary of effect of MDR1-G-1199-A variation on intracellular uptake of select HIV protease inhibitors-Saquinavir, Ritonavir and Amprenavir: Study in recombinant LLC-PK1 cells expressing MDR1 and variants

| HIV-PI | LLC-PK1 | Vmax (pmole/min*$10^6$ cells) | Km (μM) | Vmax/Km |
|---|---|---|---|---|
| Ritonavir | Control | 0.35 | 0.25 | 1.40 |
| | MDR1-wt | 0.29 | 1.00 | 0.29 |
| | MDR1-1199A | 0.35 | 2.60 | 0.13 |
| Saquinavir | Control | 1.47 | 2.00 | 0.74 |
| | MDR1-wt | 1.13 | 18.00 | 0.06 |
| | MDR1-1199A | 1.00 | 14.5 | 0.07 |
| Amprenavir | Control | 0.048 | 0.25 | 0.192 |
| | MDR1-wt | 0.036 | 10.25 | 0.004 |
| | MDR1-1199A | 0.011 | 1.00 | 0.011 |

The previous examples are provided to illustrate but not to limit the scope of the claimed inventions. Other variants of the inventions will be readily apparent to those of ordinary skill in the art and encompassed by the appended claims. All publications, patents, patent applications and other references cited herein are hereby incorporated by reference.

What is claimed is:

1. A method for predicting efficacy of a drug in a subject, said subject having a disease or disorder amenable to treatment with the drug and wherein said drug is a substrate of multi-drug resistance 1 (MDR1) gene, the method comprising:

isolating a biological sample from the subject, the biological sample comprising nucleic acids and/or proteins; and analyzing the biological sample to determine at least one of (a) the nucleotide T at position 1199 of SEQ ID NO:5, and (b) the presence or absence of the S4001 variant of SEQ ID NO:4;

wherein the presence of T at nucleotide position 1199 of SEQ ID NO:5 or the presence of the S4001 variant of SEQ ID NO:4 is indicative of an increased efficacy of the drug in the subject relative to the efficacy of the drug in an individual that is homozygous for a wild-type MDR1 gene.

2. The method of claim 1, wherein the biological sample comprises nucleic acids and the analyzing step comprises determining the nucleotide present at position 1199 of the multi-drug resistance 1 gene set forth as SEQ ID NO:5.

3. The method of claim 2, wherein the analyzing step comprises hybridization between said nucleic acid sample and a nucleic acid selected from the group consisting of (a) a nucleic acid comprising about 10 to about 100 contiguous nucleotides of a G1199T variant of the nucleotide sequence set forth in SEQ ID NO:5, said nucleic acid comprising at least one of the nucleotide at position 1199 and a base adjacent thereto; and (b) a nucleic acid that is fully complementary to the nucleic acid of (a).

4. The method of claim 2, further comprising determining the genotype at nucleotide position 1199 of the multi-drug resistance 1 gene set forth as SEQ ID NO:5.

5. The method of claim 1, wherein the drug is a cytotoxic chemotherapeutic agent.

6. The method of claim 5, wherein the chemotherapeutic agent is selected from the group consisting of doxorubicin, paclitaxol, vinblastine, and vincristine.

* * * * *

SEQUENCE LISTING

<160> NUMBER OF SEQ ID NOS: 11

<210> SEQ ID NO 1
<211> LENGTH: 4599
<212> TYPE: DNA
<213> ORGANISM: rat

<400> SEQUENCE: 1
atggcgctgc gcagcttctg cagctctgat ggctccgatc cgctctggga ttggaatgtc 60
acatggcaca ccagcaaccc tgactttacc aagtgctttc agaatacggt cctcacatgg 120

-continued

```
gtgccttgtt tctacctctg gtcctgtttc cccctctact tcctctatct ctctcgacat    180
gaccggggct acatccagat gacacacctc aacaaagcca aaactgcctt aggattcttt    240
ctgtggatca tctgctgggc agacctcttc tactctttct gggaaagaag tcagggaatg    300
ctcctagccc cggtgctact ggtcagcccg acactgctag gcatcaccat gctgctcgcc    360
accttttttaa ttcagtttga gcgaaggaaa ggagtccagt cctcagggat aatgcttact    420
ttctggcttg tagccctact ctgcgccctt gccatcttga gatctaagat catctctgcc    480
ttaaaaaagg atgctcaagt ggacatgttt cgagattctg cattctatct ctacttcacc    540
ctcgtgttca ttcagcttgt gctgtcctgc ttctcagaca gctcaccctt gttctctgaa    600
actgtccgtg acccgaatcc atgtccagaa tcgagtgcct cttttctttc caggatcact    660
ttttggtgga ttacagggat gatggtgcag ggctaccgcc agcccctgaa gagcagtgac    720
ctctggtcat tgaataaaga ggacacgtca gaagaagtgg tacctgtgct ggtgaataac    780
tggaagaagg aatgtgttaa gtcgaggaag cagcctgtac ggattgtgta tgcccctccc    840
aaagatccca ccaagcctaa gggaagttct cagttggatg tgaatgagga agtggaggca    900
ctgattgtca agtcatccca caaggaccgg gacccctctc tgttcaaggt gttgtacaag    960
acctttgggc cctacttcct catgagcttc ctgtacaagg cccttcatga cctgatgatg   1020
tttgctggcc ctgagatctt ggaattgatt atcaacttcg tgaatgacag ggaggcccct   1080
gactggcagg gctacttgta cacagcactg ctgtttgtca gtgcctgtct gcagacactg   1140
gcactccacc agtactttca tatctgcttc gtcaccggca tgcgcatcaa gactgctgtg   1200
gtgggcgctg tttaccgcaa ggctcttgtg atcaccaatt cagctagaaa atcgtccaca   1260
gttggagaga ttgtcaacct catgtccgtg gatgcccagc gcttcatgga cttggccacg   1320
tatattaaca tgatctggtc agcccctctg caagtcaccc tagccctcta cttcctgtgg   1380
ctgaacctgg gcccttctgt gctggctggg gtggctgtta tgatcctcat ggtgcccttc   1440
aatgctgtga tggccatgaa gaccaagact taccaggtgg cacacatgaa gagcaaagac   1500
aaccgaatca agctgatgaa cgagatcctc aatgggatca aagtactcaa attgtacgcc   1560
tgggagctgg ctttccagga caaagttatg aacatcaggc aggaggagct gaaggtgctg   1620
aagaaatccg cctacctggc ggctgtgggc acattcacat gggtttgcac acctttcctg   1680
gtggctctgt caacctttgc tgtctttgtg actgtggacg agaagaacat cctagatgca   1740
aagaaagcct ttgtatccct agccctgttc aatatcttgc gcttcccact caacatccta   1800
cccatggtca tcagcagcat tgtgcaggcc agcgtgtccc tcaagcgtct caggatcttt   1860
ctgtctcacg aggagctgga gccagacagc atcgagcgat ggtcgatcaa ggatggtgga   1920
gggatgaata gcatcactgt gaagaatgca accttcactt gggccaggga tgaacctccc   1980
acactgaatg gcatcacctt cgccatccct gatggagccc ttgtggccgt ggtgggccag   2040
gtaggctgtg ggaagtcatc tctgctgtca gccctgctgg ctgagatgga caaagtggag   2100
ggacatgtga ctctcaaggg ctccgtggcc tatgtgcccc agcaggcctg gattcagaat   2160
gactctctcc gagagaacat actgtttggg cgcccccctgc aggaacattg ctacaaggcg   2220
gtgatggagg cctgtgccct ccttccggat ttggaaatcc ttcccagtgg ggacctcaca   2280
gagattggtg agaagggtgt gaacctgtcg gggggccaga agcagcgtgt gagcctggct   2340
cgggctgtgt attgtaactc tgacatctac ctcttggacg accccctctc ggctgtggat   2400
gcacatgttg ggaagcacat ctttgagaag gtggtgggtc ccatgggcct actgaagaac   2460
```

-continued

```
aagacacgga tcctggtcac ccatggtatc agctacctgc cccaagtgga tgtcatcatt   2520

gtcatgagtg gcggcaagat ctcagagatg ggatcttatc aggagctgct agaccgggat   2580

ggggcctttg ctgagttcgt gcgcacctat gccaacactg agcaggacct ggcttcagag   2640

gatgacagta agaatggtgt cagtggttta gggaaggagt caaagccggt ggaaaatggg   2700

atactggtga cagacgcagt agggaagccc ctgcagaggc atctcagcaa ctcttcttcc   2760

cacagtgtgg ttactaacca gcagcacagc agcacagccg agctgcagaa gtctggggtt   2820

aaggaggaga cttggaagct gatggaagca gacaaggccc agacagggca ggtgaagctt   2880

tccgtgtact ggaactacat gaaggccatt ggcctctgca tctccttctt gagtatcttc   2940

cttttcctgt gcaatcatgt atctgcactg gcttctaact attggctgag tctctggaca   3000

gatgaccgcc ctgctgtcaa tgggactcag gagaacagga attttcgact aagtgtctat   3060

ggggccttgg gcatcttgca aggtgtggca gtatttggct attccatggc tgtgtccatt   3120

gggggcatct ttgcctcccg tcgcctgcac ctagacctgc tacagaatgt cctgcgatca   3180

cccatgagtt tctttgagcg tacacccagt gggaacctag tgaaccgatt ctccaaggag   3240

ttggacacag tggactccat gatcccgcag gtcatcaaga tgttcatggg ttcactcttc   3300

agtgtcattg gagctgtcat catcatccta ctggctacgc ccattgccgc agtcatcatc   3360

ccacccttgg gtctggttta cttctttgtg cagaggttct atgtggcctc ctctcgacag   3420

ctgaagcgcc tggagtctgt cagtcgttcc cctgtgtact cacacttcaa tgagaccttg   3480

ctgggggtca gtgtcatccg tgcctttgag gaacaggagc gcttcattcg ccaaagtgac   3540

ctgaaagtag atgagaacca gaaggcctac taccccagca ttgtggccaa caggtggctt   3600

gctgtgcgcc tggagtgtgt gggcaactgc attgtgctgt ttgctgccct tttcgcagtc   3660

atctcccggc atagcctcag tgctggcttg gtgggtctct ctgtgtctta ctcactgcag   3720

ataactgcat acttgaactg gctagttcga atgtcctctg agatggagac caacattgtg   3780

gcagtggaga gactgaagga atattctgaa acggagaagg aggcttcttg gcaaatccaa   3840

gagacagctc cacccagcac ctggccccat tcaggccgtg tagagttccg ggattactgc   3900

ttgaggtatc gagaagactt ggacttggtt ctcaagcaca taaatgtcac cattgagggt   3960

ggagaaaagg ttggtattgt gggtcgtaca ggagctggga aatcatctct caccctgggt   4020

ttgttccgga tcaatgagtc tgcagaaggg gagatcatca ttgatgggat aaacattgct   4080

aagattggcc tgcacaacct gcgcttcaag atcaccatca ttccacagga tcctgttttg   4140

ttcccgggtt ccctccgcat gaacctggac cctttcagtc agtattctga tgaagaagtc   4200

tggatggctc tggagcttgc tcacctgaag ggctttgtgt cagccttgcc tgacaagctg   4260

aaccatgagt gtgcagaagg tggagagaat ctgagtgtgg ggcagcgaca gcttgtgtgc   4320

ctggcccggg ctttgctgag gaagacaaag attctagtgt tggacgaggc tacagcagct   4380

gtggatctgg agacagatga ccttattcag tccaccgtcc ggacgcagtt tgaagacagt   4440

actgtgctca ctattgctca tcggctgaat accataatgg actatacaag ggtgattgtc   4500

ctggacaaag gagaaattcg ggagtgtggt gcaccctctg agctcctgca gcaaagaggc   4560

gtcttctata gcatggccaa ggatgctggc ttggtgtga                          4599
```

```
<210> SEQ ID NO 2
<211> LENGTH: 4587
<212> TYPE: DNA
<213> ORGANISM: mouse

<400> SEQUENCE: 2
```

-continued

```
atggcgctgc gcagcttctg cagcgctgat ggctccgatc cactctggga ctggaatgtc     60
acatggcaca ccagcaaccc cgactttacc aagtgctttc agaacacggt cctcacatgg    120
gtgccttgtt tctacctctg gtcctgtttc cccctctact tcttctatct ctctcgccat    180
gaccggggct acatccagat gacacacctc aacaaaacca aaactgcctt aggattcttt    240
ctgtggatca tctgctgggc agacctcttc tactctttct gggaaagaag tcagggagtg    300
ctccgagccc cggtgttact ggtcagccca acactgctgg gcatcaccat gctgctcgcc    360
acctttttga tacagcttga acggaggaag ggagtccaat cctcgggaat tatgcttact    420
ttctggctcg tagccctact ctgtgccctt gccatcttga gatctaagat catctctgcc    480
ttaaaaaagg atgctcatgt ggacgtgttt cgagattcca cgttctatct gtacttcacc    540
cttgtgcttg ttcagctcgt gctgtcctgc ttctcagact gctcacccct gttctctgaa    600
actgtccatg accggaatcc atgcccagaa tccagtgcct ctttcctttc caggattact    660
ttctggtgga ttacagggat gatggtgcac ggctaccgcc agcccctgga gagcagtgac    720
ctctggtcat tgaataagga ggacacatca gaagaagtgg tacctgtgct ggtgaataac    780
tggaagaagg aatgtgataa gtcaaggaag cagcctgtac ggattgtgta tgcccctccc    840
aaagatccca gcaagcctaa gggaagttcc cagttggatg tgaatgagga ggtggaggca    900
ctgattgtca agtcacccca caaggatcgg gagccctctc tgttcaaggt gttatacaag    960
acttttggtc cctacttcct catgagcttc ctgtacaagg cccttcatga cctgatgatg   1020
tttgccggcc ccaagatctt ggaattgatt atcaacttcg tgaatgacag ggaggctccc   1080
gactggcagg gctactttta cacagcactg ctgtttgtca gcgcctgtct gcagacactg   1140
gcactccacc agtactttca tatctgcttc gtcagtggca tgcgcatcaa gactgctgtg   1200
gtgggcgctg tctatcgtaa ggctcttttg atcaccaatg cagctagaaa atcttccacg   1260
gtcggagaga ttgtcaacct catgtccgtg gatgctcagc gcttcatgga cttggccacg   1320
tacattaaca tgatctggtc agcccctctg caagtcatcc tagccctcta cttcctgtgg   1380
ctgagcctgg gcccttctgt gctggctgga gtggctgtga tgattctcat ggtaccctta   1440
aatgctgtga tggccatgaa gaccaagacc taccaggtgg cacacatgaa gagcaaagac   1500
aaccgaatca agctgatgaa cgagatcctc aatgggatca aagtcctcaa gctgtacgcc   1560
tgggagctgg ccttccagga caaagtcatg agcatcaggc aggaggagct caaggtgctg   1620
aagaaatctg cctacctggc agctgtaggc acattcacgt gggtgtgcac acctttcctg   1680
gtggccctgt caacctttgc tgtctttgtg actgtggatg agagaaatat cctagatgca   1740
aagaaagcct ttgtgtccct agccctgttc aatatcttgc gcttcccact caacatcctg   1800
cccatggtta tcagcagcat tgtgcaggcc agcgtgtccc tcaagcgtct caggattttt   1860
ctgtctcatg aggagctgga gccagacagc attgagcgga ggtcgatcaa gagtggagaa   1920
gggaatagca tcactgtgaa gaatgcaacc ttcacttggg ccaggggtga acctcccaca   1980
ctgaatggca tcaccttctc cattcctgaa ggagcccttg tggccgtggt gggccaggta   2040
ggctgcggga agtcatctct gctgtcagcc ctgctggctg agatggacaa ggtggaggga   2100
catgtgactc tcaagggctc cgtggcctac gtgccccagc aggcctggat tcagaatgac   2160
tctctccgag agaacatact gtttgggcac cccctgcagg aaaattacta caaggcagtt   2220
atggaagcct gtgcccttct tccagatttg gaaatcctgc ccagtgggga ccgcacagag   2280
atcggtgaga agggtgtgaa cctgtcaggg ggccagaagc agcgtgtgag cctggcccgg   2340
```

-continued

```
gctgtgtact ctaactctga catctacctc tttgatgacc ccctctcggc tgtggatgca   2400
catgttggga agcacatctt tgagaaggtg gttggtccca tgggcctact gaagaacaag   2460
acacggatcc tggtcaccca tggtatcagc tacctgcccc aagtggatgt catcattgtc   2520
atgagtggcg gcaagatctc agagatgggt tcttatcagg agctgctaga ccgggatggg   2580
gccttcgctg agttcctgcg cacctatgcc aacgctgagc aggacctggc ctcggaggat   2640
gacagtgtca gtggttcagg gaaggagtca aagccggtgg aaaatgggat gctggtgaca   2700
gacaccgtag gaaagcacct gcagaggcat ctcagcaact cgtcttccca cagtggggat   2760
accagccagc aacacagcag catagccgaa ctgcagaagg ctggagctaa ggaggagacg   2820
tggaagctaa tggaagcaga caaggcccag acagggcagg tgcagctgtc agtgtactgg   2880
aactacatga aggccattgg cctcttcatc accttcttga gtatcttcct tttcctgtgc   2940
aaccatgtat ctgcactggc ctctaactat tggctgagcc tctggacaga tgaccccct    3000
gttgtcaatg ggactcaggc gaacaggaat tttcggctga gtgtctatgg ggccttgggc   3060
atcttgcaag gtgcagcaat atttggctac tccatggctg tgtccatcgg gggcatcttt   3120
gcctcccgtc gcttgcacct ggacctgcta tacaatgttc ttcgatcacc catgagtttc   3180
ttcgagcgta cacccagtgg gaacctagtg aaccgattct ccaaggagct ggacacagtg   3240
gactccatga tcccgcaggt catcaagatg ttcatgggtt cactcttcag tgtcattgga   3300
gctgtcatca tcatcctact ggccacgccc attgccgcag tcatcatccc acccttgggt   3360
ctggtttact tctttgtgca gaggttctat gtggcttcct caagacaact gaagcgcctg   3420
gagtctgtca gccgttcccc tgtgtactca cacttcaatg agaccttgct gggagtcagt   3480
gtcatccgtg cttttgagga gcaggagcgc ttcattcacc agagtgacct gaaagtagat   3540
gagaaccaga aggcctacta ccccagcatt gtggccaaca gatggcttgc tgtgcgcctt   3600
gagtgtgtgg gcaactgcat tgtgctgttt gctgccctct ttgcagtcat ctcccggcac   3660
agcctcagtg ctggcttggt gggcctctct gtgtcttact cactgcagat aactgcatac   3720
ttgaactggc tggttcgaat gtcctcggag atggagacca acattgtggc agtggagaga   3780
ctgaaggagt attctgaaac agagaaggag gctccttggc aaatccagga aacagctcca   3840
cccagcacct ggccccattc aggccgtgta gagttccggg attactgcct gaggtatcga   3900
gaagacttgg acttggttct caagcacata aatgtcacca ttgagggtgg agaaaaggtg   3960
ggtattgtag gtcgtacggg agctgggaaa tcatctctca ccctgggttt gttccggatc   4020
aatgagtctg cagaaggga gatcatcatt gatggggtca acatcgccaa gatcggcctg    4080
cacaacctgc gcttcaagat caccatcatt ccacaggatc ctgttttgtt ctcgggttcc   4140
ctccgcatga acttggaccc tttcagtcag tattctgatg aagaagtctg gatggccctg   4200
gagcttgctc acctaaaggg ctttgtgtca gccttgcctg acaagctgaa ccatgagtgt   4260
gcagaaggtg gagagaacct gagtgtgggg cagcgacagc ttgtgtgcct ggcccgggct   4320
ctgctgagga agacaaagat tctagtgttg gacgaggcta ccgcagctgt ggacctagag   4380
acagataacc ttatccagtc caccatccgg acgcagtttg aagactgtac tgtgctcacg   4440
attgctcatc ggcttaacac cataatggac tacacacggg ttattgtcct ggacaaagga   4500
gaagttcggg agtgtggtgc accctctgag ctcctgcagc aaagaggcat cttctacagc   4560
atggccaagg atgctggctt ggtgtga                                     4587
```

<210> SEQ ID NO 3
<211> LENGTH: 5011

<212> TYPE: DNA
<213> ORGANISM: human

<400> SEQUENCE: 3

```
ccaggcggcg ttgcggcccc ggccccggct ccctgcgccg ccgccgccgc cgccgccgcc      60

gccgccgccg ccgccgccag cgctagcgcc agcagccggg cccgatcacc cgccgcccgg     120

tgcccgccgc cgcccgcgcc agcaaccggg cccgatcacc cgccgcccgg tgcccgccgc     180

cgcccgcgcc accggcatgg cgctccgggg cttctgcagc gccgatggct ccgacccgct     240

ctgggactgg aatgtcacgt ggaataccag caaccccgac ttcaccaagt gctttcagaa     300

cacggtcctc gtgtgggtgc cttgttttta cctctgggcc tgtttcccct tctacttcct     360

ctatctctcc cgacatgacc gaggctacat tcagatgaca cctctcaaca aaaccaaaac     420

tgccttggga tttttgctgt ggatcgtctg ctgggcagac ctcttctact ctttctggga     480

aagaagtcgg ggcatattcc tggccccagt gtttctggtc agcccaactc tcttgggcat     540

caccacgctg cttgctacct ttttaattca gctggagagg aggaagggag ttcagtcttc     600

agggatcatg ctcactttct ggctggtagc cctagtgtgt gccctagcca tcctgagatc     660

caaaattatg acagccttaa aagaggatgc ccaggtggac ctgtttcgtg acatcacttt     720

ctacgtctac ttttccctct tactcattca gctcgtcttg tcctgtttct cagatcgctc     780

acccctgttc tcggaaacca tccacgaccc taatccctgc ccagagtcca gcgcttcctt     840

cctgtcgagg atcaccttct ggtggatcac agggttgatt gtccggggct accgccagcc     900

cctggagggc agtgacctct ggtccttaaa caaggaggac acgtcggaac aagtcgtgcc     960

tgttttggta aagaactgga agaaggaatg cgccaagact aggaagcagc cggtgaaggt    1020

tgtgtactcc tccaaggatc ctgcccagcc gaaagagagt tccaaggtgg atgcgaatga    1080

ggaggtggag gctttgatcg tcaagtcccc acagaaggag tggaacccct ctctgtttaa    1140

ggtgttatac aagacctttg ggccctactt cctcatgagc ttcttcttca aggccatcca    1200

cgacctgatg atgttttccg ggccgcagat cttaaagttg ctcatcaagt tcgtgaatga    1260

cacgaaggcc ccagactggc agggctactt ctacaccgtg ctgctgtttg tcactgcctg    1320

cctgcagacc ctcgtgctgc accagtactt ccacatctgc ttcgtcagtg gcatgaggat    1380

caagaccgct gtcattgggg ctgtctatcg gaaggccctg gtgatcacca attcagccag    1440

aaaatcctcc acggtcgggg agattgtcaa cctcatgtct gtggacgctc agaggttcat    1500

ggacttggcc acgtacatta acatgatctg gtcagccccc ctgcaagtca tccttgctct    1560

ctacctcctg tggctgaatc tgggcccttc cgtcctggct ggagtggcgg tgatggtcct    1620

catggtgccc gtcaatgctg tgatggcgat gaagaccaag acgtatcagg tggcccacat    1680

gaagagcaaa gacaatcgga tcaagctgat gaacgaaatt ctcaatggga tcaaagtgct    1740

aaagctttat gcctgggagc tggcattcaa ggacaaggtg ctggccatca ggcaggagga    1800

gctgaaggtg ctgaagaagt ctgcctacct gtcagccgtg ggcaccttca cctgggtctg    1860

cacgcccttt ctggtggcct tgtgcacatt tgccgtctac gtgaccattg acgagaacaa    1920

catcctggat gcccagacag ccttcgtgtc tttggccttg ttcaacatcc tccggtttcc    1980

cctgaacatt ctccccatgg tcatcagcag catcgtgcag gcgagtgtct ccctcaaacg    2040

cctgaggatc tttctctccc atgaggagct ggaacctgac agcatcgagc gacggcctgt    2100

caaagacggc gggggcacga acagcatcac cgtgaggaat gccacattca cctgggccag    2160

gagcgaccct cccacactga atggcatcac cttctccatc cccgaaggtg ctttggtggc    2220
```

-continued

```
cgtggtgggc caggtgggct gcggaaagtc gtccctgctc tcagccctct tggctgagat   2280
ggacaaagtg gaggggcacg tggctatcaa gggctccgtg gcctatgtgc cacagcaggc   2340
ctggattcag aatgattctc tccgagaaaa catccttttt ggatgtcagc tggaggaacc   2400
atattacagg tccgtgatac aggcctgtgc cctcctccca gacctggaaa tcctgcccag   2460
tggggatcgg acagagattg gcgagaaggg cgtgaacctg tctgggggcc agaagcagcg   2520
cgtgagcctg gcccgggccg tgtactccaa cgctgacatt tacctcttcg atgatcccct   2580
ctcagcagtg gatgcccatg tgggaaaaca catctttgaa aatgtgattg gccccaaggg   2640
gatgctgaag aacaagacgc ggatcttggt cacgcacagc atgagctact tgccgcaggt   2700
ggacgtcatc atcgtcatga gtggcggcaa gatctctgag atgggctcct accaggagct   2760
gctggctcga gacggcgcct tcgctgagtt cctgcgtacc tatgccagca cagagcagga   2820
gcaggatgca gaggagaacg gggtcacggg cgtcagcggt ccagggaagg aagcaaagca   2880
aatggagaat ggcatgctgg tgacggacag tgcagggaag caactgcaga gacagctcag   2940
cagctcctcc tcctatagtg gggacatcag caggcaccac aacagcaccg cagaactgca   3000
gaaagctgag gccaagaagg aggagacctg gaagctgatg gaggctgaca aggcgcagac   3060
agggcaggtc aagctttccg tgtactggga ctacatgaag gccatcggac tcttcatctc   3120
cttcctcagc atcttccttt tcatgtgtaa ccatgtgtcc gcgctggctt ccaactattg   3180
gctcagcctc tggactgatg accccatcgt caacgggact caggagcaca cgaaagtccg   3240
gctgagcgtc tatggagccc tgggcatttc acaagggatc gccgtgtttg gctactccat   3300
ggccgtgtcc atcgggggga tcttggcttc ccgctgtctg cacgtggacc tgctgcacag   3360
catcctgcgg tcacccatga gcttctttga gcggaccccc agtgggaacc tggtgaaccg   3420
cttctccaag gagctggaca cagtggactc catgatcccg gaggtcatca agatgttcat   3480
gggctccctg ttcaacgtca ttggtgcctg catcgttatc ctgctggcca cgcccatcgc   3540
cgccatcatc atcccgcccc ttggcctcat ctacttcttc gtccagaggt tctacgtggc   3600
ttcctcccgg cagctgaagc gcctcgagtc ggtcagccgc tccccggtct attcccattt   3660
caacgagacc ttgctggggg tcagcgtcat tcgagccttc gaggagcagg agcgcttcat   3720
ccaccagagt gacctgaagg tggacgagaa ccagaaggcc tattacccca gcatcgtggc   3780
caacaggtgg ctggccgtgc ggctggagtg tgtgggcaac tgcatcgttc tgtttgctgc   3840
cctgtttgcg gtgatctcca ggcacagcct cagtgctggc ttggtgggcc tctcagtgtc   3900
ttactcattg caggtcacca cgtacttgaa ctggctggtt cggatgtcat ctgaaatgga   3960
aaccaacatc gtggccgtgg agaggctcaa ggagtattca gagactgaga aggaggcgcc   4020
ctggcaaatc caggagacag ctccgcccag cagctggccc caggtgggcc gagtggaatt   4080
ccggaactac tgcctgcgct accgagagga cctggacttc gttctcaggc acatcaatgt   4140
cacgatcaat gggggagaaa aggtcggcat cgtggggcgg acgggagctg ggaagtcgtc   4200
cctgaccctg ggcttatttc ggatcaacga gtctgccgaa ggagagatca tcatcgatgg   4260
catcaacatc gccaagatcg gcctgcacga cctccgcttc aagatcacca tcatccccca   4320
ggaccctgtt ttgttttcgg gttccctccg aatgaacctg gacccattca gccagtactc   4380
ggatgaagaa gtctggacgt ccctggagct ggcccacctg aaggacttcg tgtcagccct   4440
tcctgacaag ctagaccatg aatgtgcaga aggcggggag aacctcagtg tcgggcagcg   4500
ccagcttgtg tgcctagccc gggccctgct gaggaagacg aagatccttg tgttggatga   4560
ggccacggca gccgtggacc tggaaacgga cgacctcatc cagtccacca tccggacaca   4620
```

```
gttcgaggac tgcaccgtcc tcaccatcgc ccaccggctc aacaccatca tggactacac   4680

aagggtgatc gtcttggaca aggagaaat ccaggagtac ggcgccccat cggacctcct   4740

gcagcagaga ggtcttttct acagcatggc caaagacgcc ggcttggtgt gagccccaga   4800

gctggcatat ctggtcagaa ctgcagggcc tatatgccag cgcccaggga ggagtcagta   4860

cccctggtaa accaagcctc ccacactgaa accaaaacat aaaaaccaaa cccagacaac   4920

caaaacatat tcaaagcagc agccaccgcc atccggtccc ctgcctggaa ctggctgtga   4980

agacccagga gagacagaga tgcgaaccac c                                  5011
```

<210> SEQ ID NO 4
<211> LENGTH: 1280
<212> TYPE: PRT
<213> ORGANISM: human MDRI

<400> SEQUENCE: 4

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300
```

-continued

```
Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720
```

-continued

```
Asn Gly Gly Leu Gln Pro Ala Phe Ala Ile Ile Phe Ser Lys Ile Ile
            725                 730                 735

Gly Val Phe Thr Arg Ile Asp Asp Pro Glu Thr Lys Arg Gln Asn Ser
        740                 745                 750

Asn Leu Phe Ser Leu Leu Phe Leu Ala Leu Gly Ile Ile Ser Phe Ile
    755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
            805                 810                 815

Arg Leu Ala Asn Asp Ala Ala Gln Val Lys Gly Ala Ile Gly Ser Arg
        820                 825                 830

Leu Ala Val Ile Thr Gln Asn Ile Ala Asn Leu Gly Thr Gly Ile Ile
    835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
            885                 890                 895

Ala Thr Glu Ala Ile Glu Asn Phe Arg Thr Val Val Ser Leu Thr Gln
        900                 905                 910

Glu Gln Lys Phe Glu His Met Tyr Ala Gln Ser Leu Gln Val Pro Tyr
    915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
            965                 970                 975

Val Phe Ser Ala Val Val Phe Gly Ala Met Ala Val Gly Gln Val Ser
        980                 985                 990

Ser Phe Ala Pro Asp Tyr Ala Lys  Ala Lys Ile Ser Ala  Ala His Ile
    995                 1000                 1005

Ile Met  Ile Ile Glu Lys Thr  Pro Leu Ile Asp Ser  Tyr Ser Thr
    1010                 1015                 1020

Glu Gly  Leu Met Pro Asn Thr  Leu Glu Gly Asn Val  Thr Phe Gly
    1025                 1030                 1035

Glu Val  Val Phe Asn Tyr Pro  Thr Arg Pro Asp Ile  Pro Val Leu
    1040                 1045                 1050

Gln Gly  Leu Ser Leu Glu Val  Lys Lys Gly Gln Thr  Leu Ala Leu
    1055                 1060                 1065

Val Gly  Ser Ser Gly Cys Gly  Lys Ser Thr Val Val  Gln Leu Leu
    1070                 1075                 1080

Glu Arg  Phe Tyr Asp Pro Leu  Ala Gly Lys Val Leu  Leu Asp Gly
    1085                 1090                 1095

Lys Glu  Ile Lys Arg Leu Asn  Val Gln Trp Leu Arg  Ala His Leu
    1100                 1105                 1110

Gly Ile  Val Ser Gln Glu Pro  Ile Leu Phe Asp Cys  Ser Ile Ala
    1115                 1120                 1125

Glu Asn  Ile Ala Tyr Gly Asp  Asn Ser Arg Val Val  Ser Gln Glu
```

-continued

```
    1130                1135                1140

Glu Ile  Val Arg Ala Ala Lys  Glu Ala Asn Ile His  Ala Phe Ile
    1145                1150                1155

Glu Ser  Leu Pro Asn Lys Tyr  Ser Thr Lys Val Gly  Asp Lys Gly
    1160                1165                1170

Thr Gln  Leu Ser Gly Gly Gln  Lys Gln Arg Ile Ala  Ile Ala Arg
    1175                1180                1185

Ala Leu  Val Arg Gln Pro His  Ile Leu Leu Leu Asp  Glu Ala Thr
    1190                1195                1200

Ser Ala  Leu Asp Thr Glu Ser  Glu Lys Val Val Gln  Glu Ala Leu
    1205                1210                1215

Asp Lys  Ala Arg Glu Gly Arg  Thr Cys Ile Val Ile  Ala His Arg
    1220                1225                1230

Leu Ser  Thr Ile Gln Asn Ala  Asp Leu Ile Val Val  Phe Gln Asn
    1235                1240                1245

Gly Arg  Val Lys Glu His Gly  Thr His Gln Gln Leu  Leu Ala Gln
    1250                1255                1260

Lys Gly  Ile Tyr Phe Ser Met  Val Ser Val Gln Ala  Gly Thr Lys
    1265                1270                1275

Arg Gln
    1280


<210> SEQ ID NO 5
<211> LENGTH: 4646
<212> TYPE: DNA
<213> ORGANISM: human MDRI

<400> SEQUENCE: 5

cctactctat tcagatattc tccagattcc taaagattag agatcatttc tcattctcct     60

aggagtactc acttcaggaa gcaaccagat aaaagagagg tgcaacggaa gccagaacat    120

tcctcctgga aattcaacct gtttcgcagt ttctcgagga atcagcattc agtcaatccg    180

ggccgggagc agtcatctgt ggtgaggctg attggctggg caggaacagc gccggggcgt    240

gggctgagca cagcgcttcg ctctctttgc cacaggaagc ctgagctcat tcgagtagcg    300

gctcttccaa gctcaaagaa gcagaggccg ctgttcgttt cctttaggtc tttccactaa    360

agtcggagta tcttcttcca agatttcacg tcttggtggc cgttccaagg agcgcgaggt    420

cgggatggat cttgaagggg accgcaatgg aggagcaaag aagaagaact tttttaaact    480

gaacaataaa agtgaaaaag ataagaagga aaagaaacca actgtcagtg tattttcaat    540

gtttcgctat tcaaattggc ttgacaagtt gtatatggtg gtgggaactt tggctgccat    600

catccatggg gctggacttc ctctcatgat gctggtgttt ggagaaatga cagatatctt    660

tgcaaatgca ggaaatttag aagatctgat gtcaaacatc actaatagaa gtgatatcaa    720

tgatacaggg ttcttcatga atctggagga agacatgacc aggtatgcct attattacag    780

tggaattggt gctggggtgc tggttgctgc ttacattcag gtttcatttt ggtgcctggc    840

agctggaaga caaatacaca aaattagaaa acagtttttt catgctataa tgcgacagga    900

gataggctgg tttgatgtgc acgatgttgg ggagcttaac acccgactta cagatgatgt    960

ctctaagatt aatgaagtta ttggtgacaa aattggaatg ttctttcagt caatggcaac   1020

atttttcact gggtttatag taggatttac acgtggttgg aagctaaccc ttgtgatttt   1080

ggccatcagt cctgttcttg gactgtcagc tgctgtctgg gcaaagatac tatcttcatt   1140

tactgataaa gaactcttag cgtatgcaaa agctggagca gtagctgaag aggtcttggc   1200
```

-continued

```
agcaattaga actgtgattg catttggagg acaaaagaaa gaacttgaaa ggtacaacaa   1260
aaatttagaa gaagctaaaa gaattgggat aaagaaagct attacagcca atatttctat   1320
aggtgctgct ttcctgctga tctatgcatc ttatgctctg gccttctggt atgggaccac   1380
cttggtcctc tcaggggaat attctattgg acaagtactc actgtattct tttctgtatt   1440
aattggggct tttagtgttg gacaggcatc tccaagcatt gaagcatttg caaatgcaag   1500
aggagcagct tatgaaatct tcaagataat tgataataag ccaagtattg acagctattc   1560
gaagagtggg cacaaaccag ataatattaa gggaaatttg gaattcagaa atgttcactt   1620
cagttaccca tctcgaaaag aagttaagat cttgaagggc ctgaacctga aggtgcagag   1680
tgggcagacg gtggccctgg ttggaaacag tggctgtggg aagagcacaa cagtccagct   1740
gatgcagagg ctctatgacc ccacagaggg gatggtcagt gttgatggac aggatattag   1800
gaccataaat gtaaggtttc tacgggaaat cattggtgtg gtgagtcagg aacctgtatt   1860
gtttgccacc acgatagctg aaaacattcg ctatggccgt gaaaatgtca ccatggatga   1920
gattgagaaa gctgtcaagg aagccaatgc ctatgacttt atcatgaaac tgcctcataa   1980
atttgacacc ctggttggag agagaggggc ccagttgagt ggtgggcaga agcagaggat   2040
cgccattgca cgtgccctgg ttcgcaaccc caagatcctc ctgctggatg aggccacgtc   2100
agccttggac acagaaagcg aagcagtggt tcaggtggct ctggataagg ccagaaaagg   2160
tcggaccacc attgtgatag ctcatcgttt gtctacagtt cgtaatgctg acgtcatcgc   2220
tggtttcgat gatggagtca ttgtggagaa aggaaatcat gatgaactca tgaaagagaa   2280
aggcatttac ttcaaacttg tcacaatgca gacagcagga aatgaagttg aattagaaaa   2340
tgcagctgat gaatccaaaa gtgaaattga tgccttggaa atgtcttcaa atgattcaag   2400
atccagtcta ataagaaaaa gatcaactcg taggagtgtc cgtggatcac aagcccaaga   2460
cagaaagctt agtaccaaag aggctctgga tgaaagtata cctccagttt ccttttggag   2520
gattatgaag ctaaatttaa ctgaatggcc ttattttgtt gttggtgtat tttgtgccat   2580
tataaatgga ggcctgcaac cagcatttgc aataatattt tcaaagatta taggggtttt   2640
tacaagaatt gatgatcctg aaacaaaacg acagaatagt aacttgtttt cactattgtt   2700
tctagccctt ggaattattt cttttattac atttttcctt cagggtttca catttggcaa   2760
agctggagag atcctcacca agcggctccg atacatggtt ttccgatcca tgctcagaca   2820
ggatgtgagt tggtttgatg accctaaaaa caccactgga gcattgacta ccaggctcgc   2880
caatgatgct gctcaagtta aaggggctat aggttccagg cttgctgtaa ttacccagaa   2940
tatagcaaat cttgggacag gaataattat atccttcatc tatggttggc aactaacact   3000
gttactctta gcaattgtac ccatcattgc aatagcagga gttgttgaaa tgaaaatgtt   3060
gtctggacaa gcactgaaag ataagaaaga actagaaggt gctgggaaga tcgctactga   3120
agcaatagaa aacttccgaa ccgttgtttc tttgactcag gagcagaagt ttgaacatat   3180
gtatgctcag agtttgcagg taccatacag aaactctttg aggaaagcac acatctttgg   3240
aattacattt tccttcaccc aggcaatgat gtatttttcc tatgctggat gtttccggtt   3300
tggagcctac ttggtggcac ataaactcat gagctttgag gatgttctgt tagtattttc   3360
agctgttgtc tttggtgcca tggccgtggg gcaagtcagt tcatttgctc ctgactatgc   3420
caaagccaaa atatcagcag cccacatcat catgatcatt gaaaaaaccc ctttgattga   3480
cagctacagc acggaaggcc taatgccgaa cacattggaa ggaaatgtca catttggtga   3540
```

-continued

```
agttgtattc aactatccca cccgaccgga catcccagtg cttcagggac tgagcctgga   3600

ggtgaagaag ggccagacgc tggctctggt gggcagcagt ggctgtggga agagcacagt   3660

ggtccagctc ctggagcggt tctacgaccc cttggcaggg aaagtgctgc ttgatggcaa   3720

agaaataaag cgactgaatg ttcagtggct ccgagcacac ctgggcatcg tgtcccagga   3780

gcccatcctg tttgactgca gcattgctga gaacattgcc tatggagaca acagccgggt   3840

ggtgtcacag gaagagatcg tgagggcagc aaaggaggcc aacatacatg ccttcatcga   3900

gtcactgcct aataaatata gcactaaagt aggagacaaa ggaactcagc tctctggtgg   3960

ccagaaacaa cgcattgcca tagctcgtgc ccttgttaga cagcctcata ttttgctttt   4020

ggatgaagcc acgtcagctc tggatacaga aagtgaaaag gttgtccaag aagccctgga   4080

caaagccaga gaaggccgca cctgcattgt gattgctcac cgcctgtcca ccatccagaa   4140

tgcagactta atagtggtgt ttcagaatgg cagagtcaag gagcatggca cgcatcagca   4200

gctgctggca cagaaaggca tctatttttc aatggtcagt gtccaggctg gaacaaagcg   4260

ccagtgaact ctgactgtat gagatgttaa atactttta atatttgttt agatatgaca   4320

tttattcaaa gttaaaagca aacacttaca gaattatgaa gaggtatctg tttaacattt   4380

cctcagtcaa gttcagagtc ttcagagact tcgtaattaa aggaacagag tgagagacat   4440

catcaagtgg agagaaatca tagtttaaac tgcattataa attttataac agaattaaag   4500

tagattttaa aagataaaat gtgtaatttt gtttatattt tcccatttgg actgtaactg   4560

actgccttgc taaaagatta tagaagtagc aaaaagtatt gaaatgtttg cataaagtgt   4620

ctataataaa actaaacttt catgtg                                        4646
```

<210> SEQ ID NO 6
<211> LENGTH: 35
<212> TYPE: DNA
<213> ORGANISM: synthetic primer

<400> SEQUENCE: 6

```
cagaaatgtt cacttcaatt acccatctcg aaaag                               35
```

<210> SEQ ID NO 7
<211> LENGTH: 33
<212> TYPE: DNA
<213> ORGANISM: synthetic primer

<400> SEQUENCE: 7

```
tttcgagatg ggtaattgaa gtgaacattt ctg                                 33
```

<210> SEQ ID NO 8
<211> LENGTH: 21
<212> TYPE: DNA
<213> ORGANISM: synthetic primer

<400> SEQUENCE: 8

```
gtttaactta agcttggtac c                                              21
```

<210> SEQ ID NO 9
<211> LENGTH: 22
<212> TYPE: DNA
<213> ORGANISM: synthetic primer

<400> SEQUENCE: 9

```
ggtactaagc tttctgtctt gg                                             22
```

-continued

```
<210> SEQ ID NO 10
<211> LENGTH: 35
<212> TYPE: DNA
<213> ORGANISM: synthetic primer

<400> SEQUENCE: 10

cagaaatgtt cacttcattt acccatctcg aaaag                          35


<210> SEQ ID NO 11
<211> LENGTH: 33
<212> TYPE: DNA
<213> ORGANISM: synthetic primer

<400> SEQUENCE: 11

tttcgagatg ggtaaatgaa gtgaacattt ctg                            33
```